(12) United States Patent
Pinchuk et al.

(10) Patent No.: US 9,713,698 B2
(45) Date of Patent: Jul. 25, 2017

(54) STRETCH VALVE BALLOON CATHETER AND METHODS FOR PRODUCING AND USING SAME

(71) Applicant: Mayser, LLC, Fort Lauderdale, FL (US)

(72) Inventors: Leonard Pinchuk, Miami, FL (US); Gary A. Kaiser, Winter Park, FL (US); Gregory L. Mayback, Cooper City, FL (US); James Leone, Pittsburgh, PA (US)

(73) Assignee: Mayser, LLC, Fort Lauderdale, FL (US)

( * ) Notice: Subject to any disclaimer, the term of this patent is extended or adjusted under 35 U.S.C. 154(b) by 497 days.

(21) Appl. No.: 14/473,244

(22) Filed: Aug. 29, 2014

(65) Prior Publication Data

US 2014/0371672 A1 Dec. 18, 2014

Related U.S. Application Data

(60) Continuation-in-part of application No. 13/862,163, filed on Apr. 12, 2013, now Pat. No. 9,056,192, (Continued)

(51) Int. Cl.
*A61M 31/00* (2006.01)
*A61M 37/00* (2006.01)
(Continued)

(52) U.S. Cl.
CPC .. *A61M 25/10185* (2013.11); *A61M 25/0017* (2013.01); *A61M 25/04* (2013.01);
(Continued)

(58) Field of Classification Search
CPC ...... A61M 2025/0018; A61M 25/0017; A61M 25/04; A61M 25/10185;
(Continued)

(56) References Cited

U.S. PATENT DOCUMENTS 1,939,413 A 12/1933 Robinson
3,402,718 A 9/1968 Doherty
(Continued)

FOREIGN PATENT DOCUMENTS

GB 2484598 A 4/2012
JP 2002143311 5/2002
(Continued)

OTHER PUBLICATIONS

European Search Report of European Patent App. No. 13861184.3 dated Aug. 19, 2016.
(Continued)

*Primary Examiner* — Rebecca E Eisenberg
(74) *Attorney, Agent, or Firm* — Mayback & Hoffman P.A.; Gregory L. Mayback

(57) ABSTRACT

A safety balloon catheter includes a catheter having a stretch valve, a connector, a balloon inflated with an inflation fluid, a hollow inflation lumen extending through the catheter to the balloon and conveying inflation fluid thereto and therefrom, a hollow second lumen, and a balloon drainage port fluidically connecting the balloon to the second lumen. The stretch valve has a hollow base fixed in the second lumen at a proximal catheter end and shaped to permit a fluid therethrough and a hollow plug slidably positioned in the second lumen at a given distance from the base to, in a steady state, prevent inflation fluid from passing through the drainage port and, when actuated, slide within the second lumen to permit inflation fluid to pass through the drainage port and into the second lumen. The connector connects the base and the plug and has a length greater than the given distance.

20 Claims, 25 Drawing Sheets

Related U.S. Application Data which is a continuation-in-part of application No. 13/707,752, filed on Dec. 7, 2012, now Pat. No. 8,591,497, application No. 14/473,244, which is a continuation-in-part of application No. 13/868,376, filed on Apr. 23, 2013, now Pat. No. 9,586,022, which is a continuation-in-part of application No. 13/707,752, filed on Dec. 7, 2012, now Pat. No. 8,591,497, and a continuation-in-part of application No. 13/862,163, filed on Apr. 12, 2013, now Pat. No. 9,056,192, application No. 14/473,244, which is a continuation-in-part of application No. 14/024,151, filed on Sep. 11, 2013, now Pat. No. 9,272,120, which is a division of application No. 13/707,752, filed on Dec. 7, 2012, now Pat. No. 8,591,497, and a continuation-in-part of application No. 13/713,205, filed on Dec. 13, 2012, now Pat. No. 9,005,165, application No. 14/473,244, which is a continuation-in-part of application No. 14/024,440, filed on Sep. 11, 2013, now Pat. No. 9,044,571, which is a continuation-in-part of application No. 13/707,752, filed on Dec. 7, 2012, now Pat. No. 8,591,497, and a continuation-in-part of application No. 13/862,163, filed on Apr. 12, 2013, now Pat. No. 9,056,192, and a continuation-in-part of application No. 13/868,376, filed on Apr. 23, 2013, now Pat. No. 9,586,022, application No. 14/473,244, which is a continuation-in-part of application No. 14/292,112, filed on May 30, 2014, now Pat. No. 9,669,193, which is a continuation-in-part of application No. 14/024,440, filed on Sep. 11, 2013, now Pat. No. 9,044,571, and a continuation-in-part of application No. 14/024,151, filed on Sep. 11, 2013, now Pat. No. 9,272,120, and a continuation-in-part of application No. 13/868,376, filed on Apr. 23, 2013, now Pat. No. 9,586,022, and a continuation-in-part of application No. 13/862,163, filed on Apr. 12, 2013, now Pat. No. 9,056,192, and a continuation-in-part of application No. 13/713,205, filed on Dec. 13, 2012, now Pat. No. 9,005,165, which is a division of application No. 12/943,453, filed on Nov. 10, 2010, now Pat. No. 8,382,708, application No. 14/473,244, which is a continuation-in-part of application No. 13/713,205, filed on Dec. 13, 2012, now Pat. No. 9,005,165, which is a division of application No. 12/943,453, filed on Nov. 10, 2010, now Pat. No. 8,382,708.

(60) Provisional application No. 61/637,690, filed on Apr. 24, 2012.

(51) Int. Cl.
    *A61M 29/00*     (2006.01)
    *A61M 25/10*     (2013.01)
    *A61M 25/00*     (2006.01)
    *A61M 25/04*     (2006.01)

(52) U.S. Cl.
    CPC .............. *A61M 2025/0018* (2013.01); *A61M 2025/1093* (2013.01)

(58) Field of Classification Search
    CPC .. A61M 2025/1093; A61M 2210/1085; A61M 25/10181; A61M 25/10184; A61M 2025/0175; A61M 25/0026; A61M 25/0032
See application file for complete search history.

(56) References Cited

U.S. PATENT DOCUMENTS

| | | |
|---|---|---|
| 3,482,576 A | 12/1969 | Ericson et al. |
| 3,742,960 A | 7/1973 | Dye et al. |
| 3,860,007 A | 1/1975 | Binard et al. |
| 3,951,153 A | 4/1976 | Leucci |
| 4,116,201 A | 9/1978 | Shah |
| 4,212,192 A | 7/1980 | Taylor |
| 4,248,214 A | 2/1981 | Hannah et al. |
| 4,284,081 A | 8/1981 | Kasper et al. |
| 4,384,584 A | 5/1983 | Chen et al. |
| 4,444,185 A | 4/1984 | Shugar et al. |
| 4,995,863 A | 2/1991 | Nichols et al. |
| 4,998,930 A | 3/1991 | Lundahl et al. |
| 5,066,292 A | 11/1991 | Muller et al. |
| 5,078,681 A | 1/1992 | Kawashima |
| 5,217,434 A | 6/1993 | Arney et al. |
| 5,301,688 A | 4/1994 | Stephen et al. |
| 5,378,238 A | 1/1995 | Peters et al. |
| 5,391,148 A | 2/1995 | Bonis |
| 5,429,620 A | 7/1995 | Davis |
| 5,449,354 A | 9/1995 | Konwitz et al. |
| 5,624,395 A | 4/1997 | Mikhail et al. |
| 5,709,653 A | 1/1998 | Leone et al. |
| 6,013,053 A | 1/2000 | Bower |
| 6,050,973 A | 4/2000 | Duffy |
| 6,086,558 A | 7/2000 | Bower et al. |
| 6,146,409 A | 11/2000 | Overholt |
| 6,375,637 B1 | 4/2002 | Campbell et al. |
| 6,516,216 B1 | 2/2003 | Fontenot et al. |
| 7,186,214 B2 | 3/2007 | Ness |
| 7,413,558 B2 | 8/2008 | Kelley et al. |
| 7,413,564 B2 | 8/2008 | Morris et al. |
| 7,537,580 B2 | 5/2009 | Willard |
| 9,084,868 B2 | 7/2015 | Aaronson et al. |
| 2001/0037085 A1 | 11/2001 | Keith et al. |
| 2002/0010488 A1 | 1/2002 | Crawford et al. |
| 2002/0188204 A1 | 12/2002 | McNamara et al. |
| 2004/0147874 A1 | 7/2004 | Kliem et al. |
| 2005/0080340 A1 | 4/2005 | Stewart et al. |
| 2005/0197668 A1 | 9/2005 | Lim et al. |
| 2005/0273052 A1 | 12/2005 | Jorgensen |
| 2006/0161102 A1 | 7/2006 | Newcomb et al. |
| 2006/0167438 A1 | 7/2006 | Kalser et al. |
| 2006/0276746 A1 | 12/2006 | Burnside |
| 2007/0106320 A1 | 5/2007 | Blix et al. |
| 2007/0255209 A1 | 11/2007 | Crooms |
| 2008/0161748 A1 | 7/2008 | Tolkoff et al. |
| 2010/0282625 A1 | 11/2010 | Lang |
| 2011/0071506 A1 | 3/2011 | Gardner et al. |
| 2011/0082444 A1 | 4/2011 | Mayback et al. |
| 2011/0152761 A1 | 6/2011 | Mayback et al. |

FOREIGN PATENT DOCUMENTS

| | | |
|---|---|---|
| JP | 2006-333888 A | 12/2006 |
| JP | 2010029318 A | 2/2010 |
| WO | 90/00914 | 2/1990 |
| WO | 94/02195 | 2/1994 |
| WO | 95/08949 | 4/1995 |
| WO | 99/45837 | 9/1999 |
| WO | 2011/060158 | 5/2011 |

OTHER PUBLICATIONS

International Search Report of PCT/US10/56368 dated Jan. 14, 2011.
International Search Report of PCT/US13/37909 dated Sep. 16, 2013.
International Search Report of PCT/US13/59351 dated Dec. 12, 2013.
Kafali, Hasan, et al.; "Expeditious Method of Urethrovesical Junction Determination in Retropubic Colposuspension with Intraballoon Illumination of Foley Catheter"; Urologia Internationalis; May 2003, vol. 70, pp. 262-264.

(56) References Cited

OTHER PUBLICATIONS

Extended European Search Report of EP Patent Application No. 10830723.2 dated Jan. 24, 2014.
Patent Examination Report No. 1, dated Aug. 19, 2014 in AU Patent Application No. 2013205073.
European Search Report of PCT/US2013059351 Dated Aug. 19, 2016.
Notice of Rejection from Japanese Patent App. No. 2015-509096 dated Mar. 7, 2017.

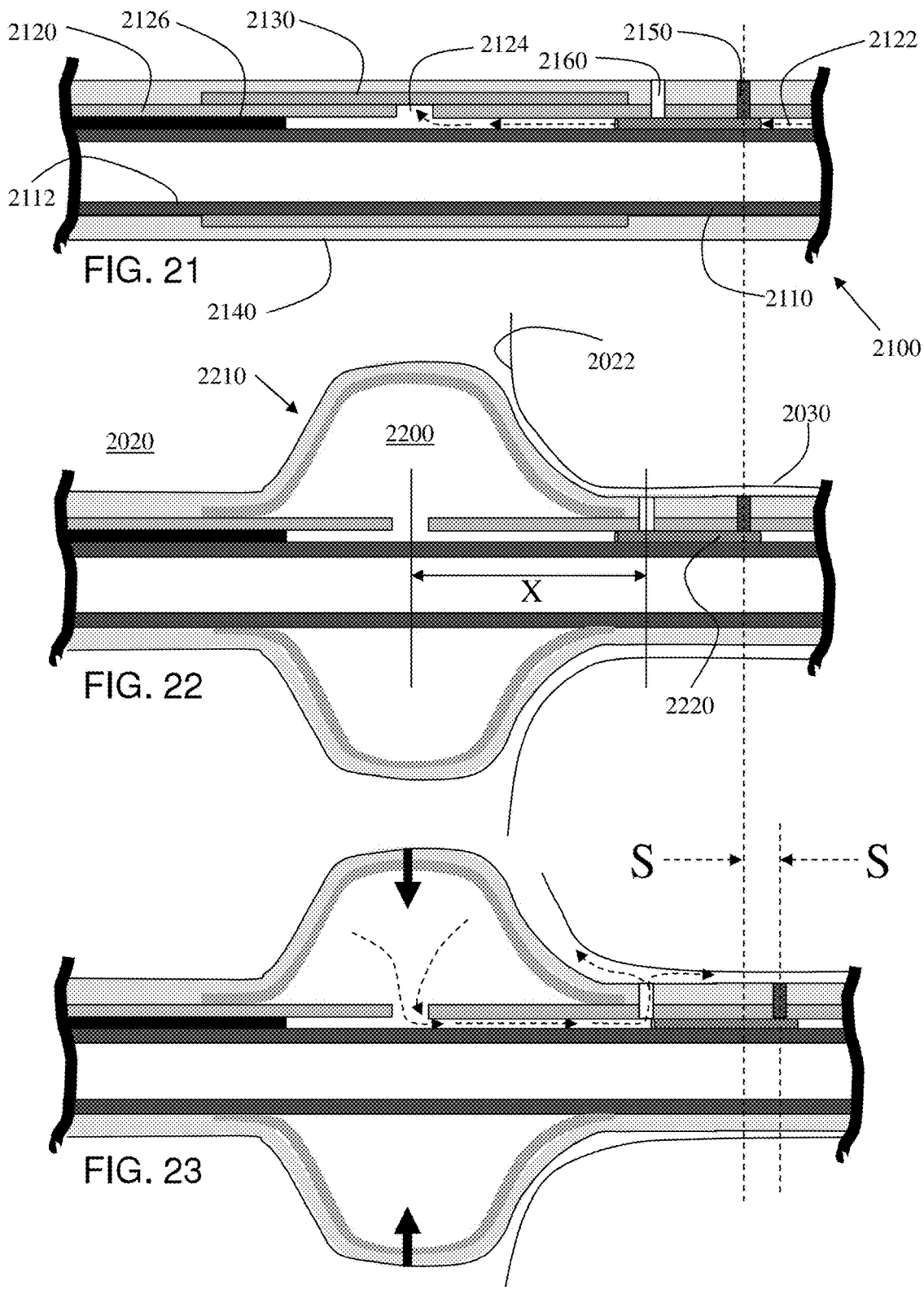

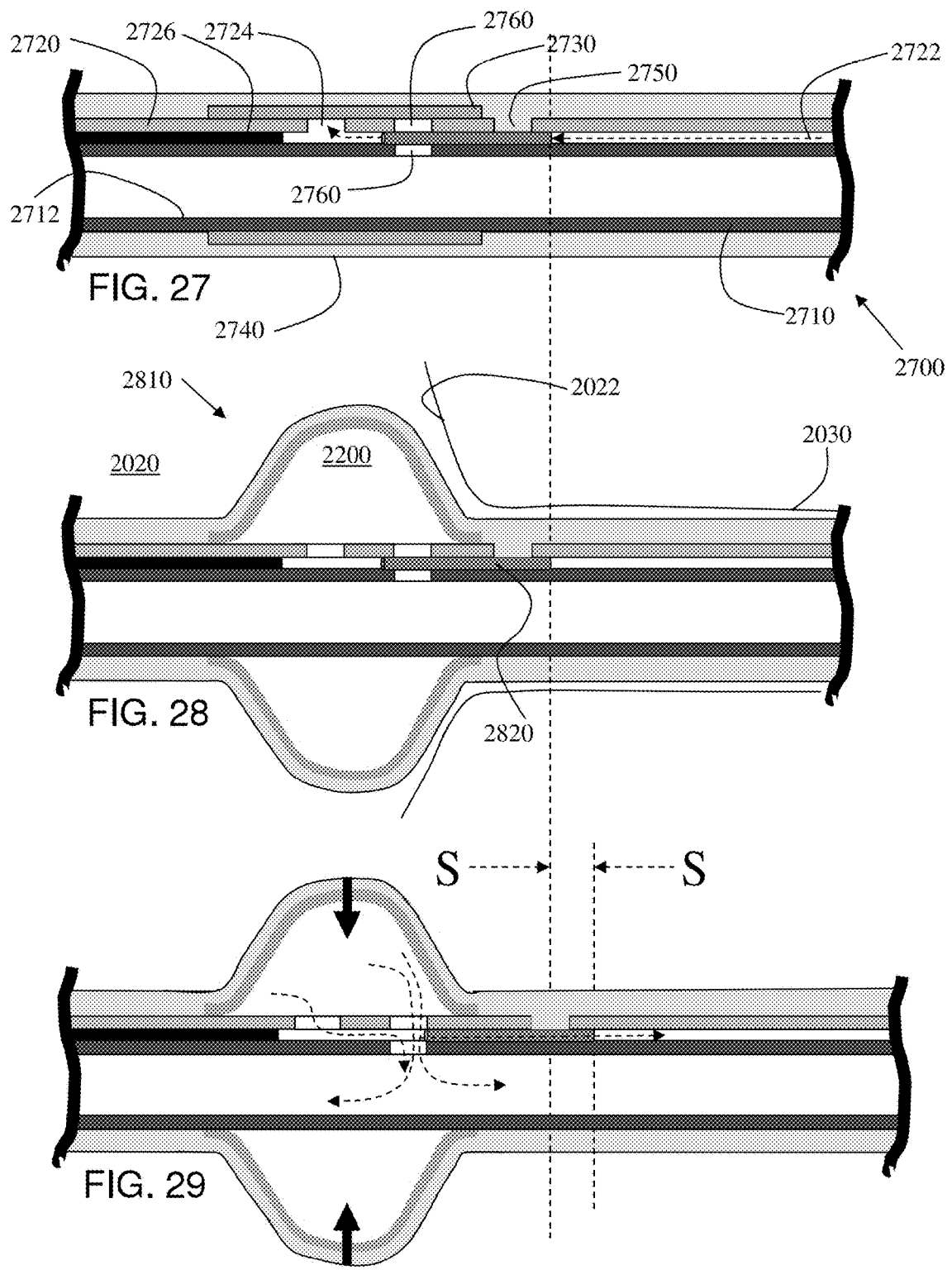

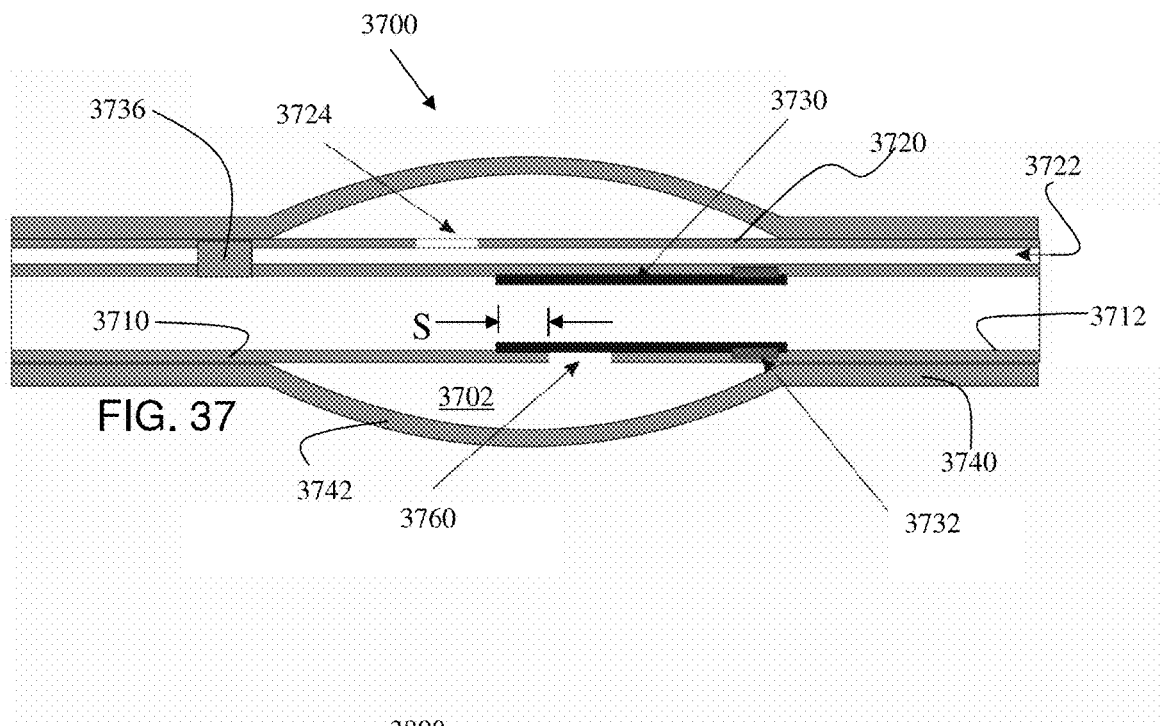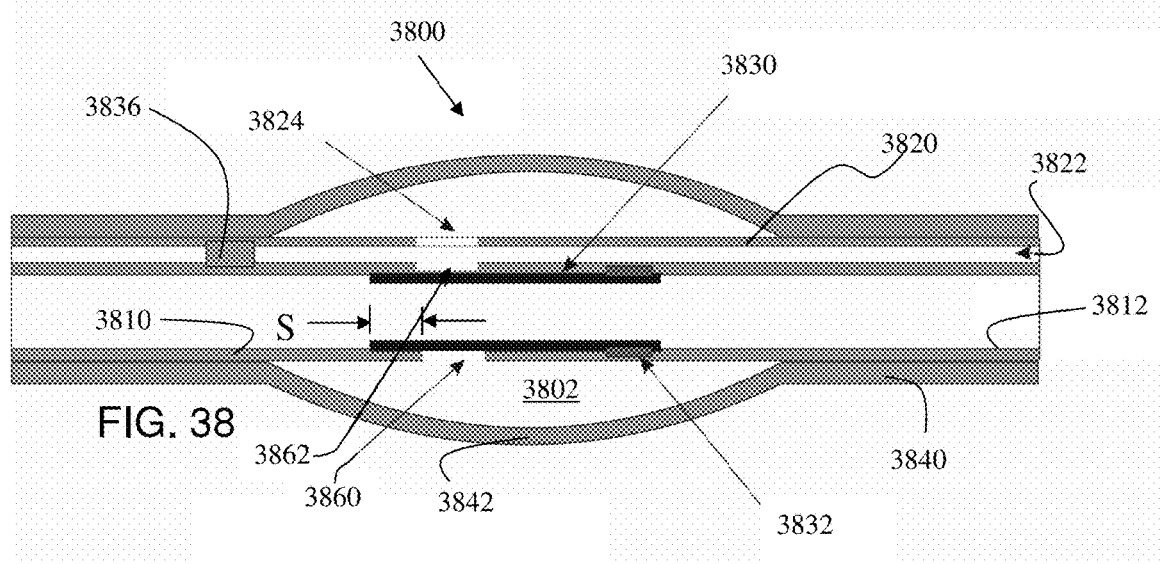

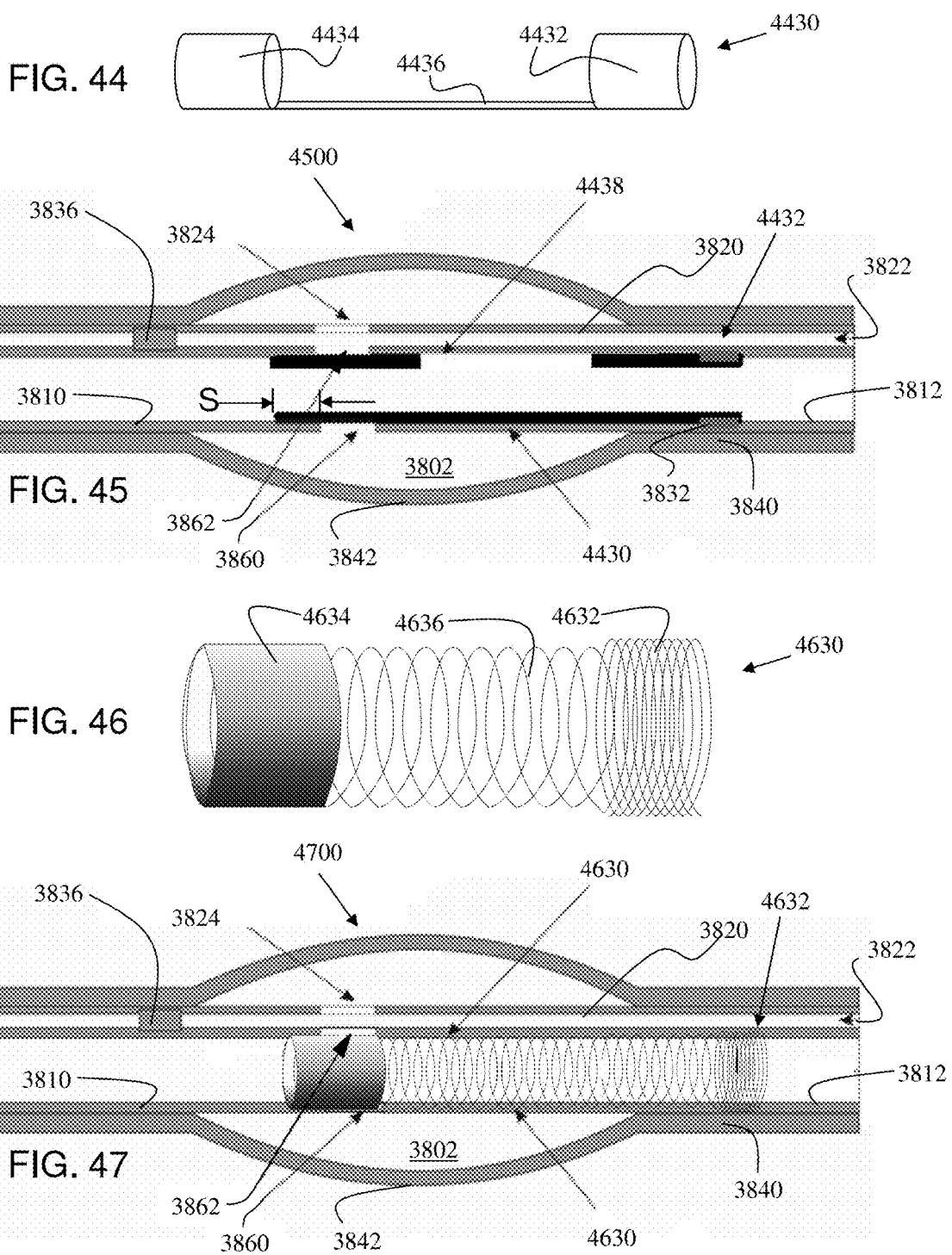

STRETCH VALVE BALLOON CATHETER AND METHODS FOR PRODUCING AND USING SAME

CROSS-REFERENCE TO RELATED APPLICATIONS

The present application:
is a continuation-in-part of U.S. patent application Ser. No. 13/862,163, filed on Apr. 12, 2013, now U.S. Pat. No. 9,056,192, issued Jun. 16, 2015, which:
  claims the benefit of U.S. Provisional Patent Application No. 61/637,690, filed on Apr. 24, 2012;
  is a continuation-in-part of U.S. patent application Ser. No. 13/707,752, filed on Dec. 7, 2012, now U.S. Pat. No. 8,591,497, issued Nov. 26, 2013;
is a continuation-in-part of U.S. patent application Ser. No. 13/868,376, filed on Apr. 23, 2013, now U.S. Pat. No. 9,586,022, issued Mar. 7, 2017, which:
  claims the benefit of U.S. Provisional Patent Application No. 61/637,690, filed on Apr. 24, 2012;
  is a continuation-in-part of U.S. patent application Ser. No. 13/707,752, filed on Dec. 7, 2012, now U.S. Pat. No. 8,591,497, issued Nov. 26, 2013; and
  is a continuation-in-part of U.S. patent application Ser. No. 13/862,163, filed on Apr. 12, 2013, now U.S. Pat. No. 9,056,192, issued Jun. 16, 2015;
is a continuation-in-part of U.S. Patent Application Ser. No. 14/024,151, filed on Sep. 11, 2013, now U.S. Pat. No. 9,272,120, issued Mar. 1, 2016, which:
  is a divisional of U.S. patent application Ser. No. 13/707,752, filed on Dec. 7, 2012, now U.S. Pat. No. 8,591,497, issued Nov. 26, 2013;
  is a continuation-in-part of U.S. patent application Ser. No. 13/713,205, filed on Dec. 13, 2012, now U.S. Pat. No. 9,005,165, issued Apr. 14, 2015;
is a continuation-in-part of U.S. patent application Ser. No. 14/024,440, filed on Sep. 11, 2013, now U.S. Pat. No. 9,044,571, issued Jun. 2, 2015, which:
  is a continuation-in-part of U.S. patent application Ser. No. 13/707,752, filed on Dec. 7, 2012, now U.S. Pat. No. 8,591,497, issued Nov. 26, 2013;
  is a continuation-in-part of U.S. patent application Ser. No. 13/862,163, filed on Apr. 12, 2013, now U.S. Pat. No. 9,056,192, issued Jun. 16, 2015;
  is a continuation-in-part of U.S. patent application Ser. No. 13/868,376, filed on Apr. 23, 2013, now U.S. Pat. No. 9,586,022, issued Mar. 7, 2017;
is a continuation-in-part of U.S. patent application Ser. No. 14/292,112, filed on May 30, 2014 which:
  is a continuation-in-part of U.S. patent application Ser. No. 14/024,440, filed on Sep. 11, 2013, now U.S. Pat. No. 9,044,571, issued Jun. 2, 2015;
  is a continuation-in-part of U.S. patent application Ser. No. 14/024,151, filed on Sep. 11, 2013, now U.S. Pat. No. 9,272,120, issued Mar. 1, 2016;
  is a continuation-in-part of U.S. patent application Ser. No. 13/868,376, filed on Apr. 23, 2013, now U.S. Pat. No. 9,586,022, issued Mar. 7, 2017;
  is a continuation-in-part of U.S. patent application Ser. No. 13/862,163, filed on Apr. 12, 2013, now U.S. Pat. No. 9,056,192, issued Jun. 16, 2015;
  is a continuation-in-part of U.S. patent application Ser. No. 13/713,205, filed on Dec. 13, 2012, now U.S. Pat. No. 9,005,165, issued Apr. 14, 2015, which:
    is a divisional of U.S. patent application Ser. No. 12/943,453, filed on Nov. 10, 2010, now U.S. Pat. No. 8,382,708, issued Feb. 26, 2013;
  is a continuation-in-part of U.S. patent application Ser. No. 13/713,205, filed on Dec. 13, 2012, now U.S. Pat. No. 9,005,165, issued Apr. 14, 2015 which:
    is a divisional of U.S. patent application Ser. No. 12/943,453, filed on Nov. 10, 2010, now U.S. Pat. No. 8,382,708, issued Feb. 26, 2013;
the prior applications are hereby incorporated herein by reference in their entirety.

BACKGROUND OF THE INVENTION

Field of the Invention

The present invention relates to a catheter, especially an automatically deflating balloon catheter with a stretch valve and methods for using and manufacturing such a catheter.

Description of Related Prior Art

A number of conventional balloon catheters exist in the prior art. Some catheters are used to drain the bladder of a patient during surgical procedure or to treat bladder and/or urethra or prostate conditions, for example. Other catheters are used to occlude a lumen, such as a blood vessel, for various reasons (e.g., isolation, angioplasty, valvuloplasty), to pull a thrombus out of a blood vessel, or to dilates strictures. Further catheters are used to provide assistance with breathing, such as endotracheal tubes. One example is a common balloon catheter referred to as a Foley catheter, which is widely used today for treating and draining a patient's bladder. The Foley catheter is shown in FIG. 1 and has a multi-lumen shaft 1 that is disposed in the urethra 10, a balloon portion 3 disposed at the distal end of the shaft 1, a fluid drain section 4 disposed at the distal end of the balloon 3, and a curved or straight, distal guiding tip 5 at the distal-most end of the entire catheter. When placed properly, the proximal-most side of the inflated balloon 3 rests on the interior wall 31 of the bladder 30, entirely blocking off the bladder-urethral junction 11 connecting the bladder 30 and the urethra 10. In such a position, the fluid drain section 4 allows continuous drainage of the bladder 30 and the balloon 3 virtually prevents the catheter from slipping out of the bladder. This ideally inserted position is shown in FIG. 1. As used herein, a fluid can be either a liquid or a gas. Exemplary fluids for inflating a balloon 3 are saline, sterile water, air, or carbon dioxide gas. Exemplary fluids drained by the catheters mentioned herein include urine and blood.

Basically, the balloon catheter has a tube-like body with two lumens passing therethrough. The larger lumen is open to the treatment location for drainage of the fluid (e.g., urine in the bladder) distally or upstream and empties into a non-illustrated ex-corporeal bag (proximally or downstream) for eventual disposal. A smaller lumen is used to inflate (and deflate) the balloon 3 with sterile water (typically) using a syringe attached to the inflation lumen fitting 260 (see, e.g., FIG. 3). When inflated in the bladder, for example, the catheter is substantially prevented from sliding out of the urethra in use.

A conventional balloon 3 has a substantially constant balloon wall thickness. The balloon 3 is fixed to the outer surface of a fluid drainage line (not illustrated in FIG. 1) and is not intended to be removed therefrom or to burst thereon unless an extraordinary amount of inflation occurs. If such an event happens, the material of the balloon will open at a random location based upon the microscopic fractures or weaknesses in the material itself. Such a tearing event is not supposed to occur under any circumstances during use with a patient.

Prior art urinary catheters are not constructed to prevent tearing of the urethra during a catheter implanting procedure and are not constructed to break in any predefined way. Prior art catheters are designed to deflate only when actively deflated, either by a syringe similar to the one that inflated it or by surgery after the physician diagnoses the balloon as not being able to deflate, in which circumstance, a procedure to pop the balloon surgically is required.

Over 96 million indwelling catheters are sold worldwide on an annual basis. Twenty four million catheters are sold to hospitals in the U.S. There are numerous complications associated with those catheters that need to be prevented. These complications are responsible for increases in hospital stays, excessive bleeding, mortality, as well as morbidity. They also cause an increased expense and burden on the already-stressed health care system.

The complications result from several different mechanisms. First, and probably most common, is improper placement of the catheter. Because of the unique anatomy of the male urethra, placing a urethral catheter for urinary drainage can be difficult. A problem arises when the physician, technician, or nurse thinks that the catheter is actually in a proper position when it is not. The proper position for the catheter is with the balloon located in the cavity of the bladder. In this position, the tip distal to the balloon is located in the bladder and is used to drain the bladder cavity of urine.

For placement of this catheter in the bladder 30 in the ideal position, however, the physician or technician has no visual aid. As shown in FIG. 1, the wall 40 defining the bladder-urethral junction 11 is very short in the longitudinal direction of the urethra 10. If the physician inserts the catheter too far into the bladder 30, no damage occurs from balloon inflation; however, there is a possibility of leakage around the balloon 3, which, under normal conditions, actually helps to lubricate the urethra 10. In such a case, gentle proximal movement of the shaft 1 will place the proximal side of the balloon 3 against the bladder-urethral junction 11. The bladder 30 can then easily expand and stretch to compensate for the balloon 3. A normal bladder capacity is 400 cc to 500 cc. A normal balloon capacity is approximately 10 cc to 12 cc although larger balloons are sometimes used. A typical balloon is 5 cc, however, most clinicians put 10 cc of water in the balloon for inflation. With 5 cc of water in the balloon, the diameter is approximately 2 cm and with 10 cc the diameter is approximately 2.5 cm.

Complications occur when the technician and/or nurse inflates the balloon when the balloon is not in the bladder. If the technician does not insert the catheter in far enough, then the balloon 3 will be inflated within the urethra 10—a condition that, while common, is to be avoided at all costs and is a frequent cause of bladder infections created during a hospital or clinic visit. Infections arise because inflation of the bladder 3 inside the urethra 10 causes the urethra 10 to stretch too far and tear. Even though the urethra 10 is a flexible tube, it has limits to which it can be safely stretched from within. Almost every balloon catheter has a balloon outer diameter/circumference that well-exceeds the safe stretching limit of the urethra 10. Therefore, if the balloon catheter is not inserted far enough, inflation of the balloon 3 will cause serious injury to the urethra 10. This is especially true with elderly patients who have urethras that are not as elastic as younger patients. Also, just as important is the change in anatomy of older males, in particular, the prostatic portion of the urethra. With age, the prostate becomes larger and, sometimes, the catheter cannot be advanced through the prostatic portion of the urethra. When this occurs, the technician does not insert the catheter all the way into the bladder and inflates the balloon within the urethra. Alternatively, strictures, i.e., scar tissue, cause the catheter to halt and further pressure tears the urethral wall to create a new, unintended passage. Both of these improper insertions cause severe bleeding and damage.

The elastomeric balloon of present-day catheter products requires relatively high pressures to initiate inflation and expand to an expected full-diameter shape upon over-inflation. As such, when incorrectly placed in the urethra, the rapid inflation, combined with the high-pressure, causes the balloon to tear the surrounding membrane, referred to as the mucosa. Tearing of the urethra 10 in this way causes bleeding and allows bacteria to enter into the bloodstream at the tear site, thus causing the subsequent bladder infection and, eventually, sepsis. Significant bleeding can become life threatening. The urethra can normally dilate several millimeters; however, when the balloon is inflated, this dilation is usually several centimeters. Also, without sufficient and immediate venting of the balloon inflation fluid after improper placement, an accidental or intentional pull on the catheter externally can and does cause extensive bodily harm to the patient.

Life threatening bleeds, especially in patients who are anticoagulated, can and do occur. Also, when the urine is infected, as in immunocompromised patients and the elderly, the bacteria enter the blood stream and can cause serious infections (e.g., sepsis), which frequently can lead to death. If the patient survives the initial trauma, then long-term complications, such as strictures, can and usually do occur. Strictures cause narrowings within the urine channel and usually require additional procedures and surgeries to correct.

Other mechanisms of catheter-induced injuries are inadvertent manipulation of the tubing or dislodging of the balloon—caused when the catheter is pulled from outside the patient due to a sudden jerk or tension. This commonly happens when the patient is ambulating or traveling from the bed to the commode or bathroom. The tubing may inadvertently become fixed while the patient is still moving, at which time a sudden jerk is imparted upon the balloon and pulls the balloon into the urethra, which tears the urethra, causing severe pain and bleeding. Injury caused by the improper, inadvertent, and/or early removal of an inflated balloon catheter is referred to as iatrogenic injury (also referred to as an in-hospital injury). Hundreds of thousands of such iatrogenic injuries occur each year—all of which need to be prevented, not only for patient safety, but also because the cost imposed on the medical health industry for each injury is enormous.

Yet another scenario occurs when the patient deliberately pulls on the catheter, thereby causing self-induced pain and injury to the urethra. This commonly happens in confused patients, for example, patients in nursing homes who have a disease or cognitive dysfunction problem, such as Alzheimer's disease, or other diseases that make the patient unable to understand the necessity of having a catheter. Confusion occurs when the patient has a spasm causing pain and a strong urge to urinate. During the spasm, the confused patient often tugs and pulls on a catheter, which results in injury. Like iatrogenic injuries, these self-induced injuries must be prevented. In the particular case of injury caused by catheter withdrawal when the balloon is inflated (either iatrogenic or self-induced), hospitals have categorized such injuries as "never events"—occurrences that should never happen. Under such circumstances, insurance typically does not cover the resulting extensive medical expenses.

The injuries mentioned herein are not limited to males and also cause severe damage to the female bladder and urethra. The injuries can also occur post-surgically, which makes the damage even more severe. One common situation where injury is caused is when the patient is medicated with morphine or other analgesics that render the patient confused and unable to make rational decisions. Feeling the foreign body inside the urethra, the confused patient does not know to leave it alone and, instead, gives it the injury-causing tug. These injuries have been well-documented and are not limited to adults. Numerous injuries are documented in pediatric patients.

Usually, it takes time to make a diagnosis of patient-caused catheter injury. Immediately after diagnosing the injury, a technician needs to deflate the catheter. However, once the urethra is torn, replacing the damaged catheter with another catheter is quite difficult and, in fact, exacerbates the injury. Sometimes, the patient has to be taken to the operating room to replace a urinary drainage tube once the injury occurs. Because catheters and leg bags are now used routinely in certain situations during home health care, this scenario is not limited to hospitals and occurs at nursing homes and patients' homes as well.

Most of the recent catheter technology has been focused on reducing urinary tract infections that are caused by catheters, injuries that are usually the most common catheter-related complications. One example of such technology is impregnation of the catheter with antimicrobials or antibiotics. But, these advances do nothing to prevent the injuries explained herein.

With regard to balloon catheters other than urinary catheters, such as endotracheal tubes, tracheostomy tubes, fogarty-type atherectomy balloon catheters, isolation catheters, angioplasty balloon catheters, valvuloplasty catheters, vertebroplasty balloons, and other balloons that dilate lumens, none are provided with any self-regulating or self-deflating safety features.

Accordingly, it would be beneficial to provide a balloon catheter that does not inflate past the tearing limit of a lumen (e.g., a urethra) and deflates in a desired, predefined way under certain conditions.

SUMMARY OF THE INVENTION

It is accordingly a desire to provide an automatically deflating pressure balloon catheter with a stretch valve and methods for manufacturing and using the catheter that overcome the hereinafore-mentioned disadvantages of the heretofore-known devices and methods of this general type and quickly and rapidly deflates if pulled out prior to physician-scheduled deflation of the balloon or that deflates partially if over-inflated.

With the foregoing and other objects in view, there is provided, in accordance with the invention, a safety balloon catheter including a flexible, multi-lumen balloon catheter having a proximal catheter end, a balloon defining a balloon interior to be inflated with an inflation fluid, a hollow inflation lumen extending through the catheter to the balloon interior and shaped to convey the inflation fluid to and from the balloon interior, a hollow second lumen parallel to the inflation lumen, and a balloon drainage port fluidically connecting the balloon interior to the second lumen, a stretch valve having a hollow base fixed in the second lumen adjacent the proximal catheter end and shaped to permit a fluid to pass therethrough and a hollow plug shaped to permit a fluid to pass therethrough and slidably positioned in the second lumen at a given distance from the base to, in a steady state, prevent the inflation fluid from passing through the drainage port and, in an actuated state, slide within the second lumen to permit the inflation fluid to pass through the drainage port and into the second lumen, and a connector connected to the base and to the plug and having a length equal to or greater than the given distance between the hollow plug and the base.

With the objects of the invention in view, there is also provided a safety urinary catheter including a flexible, multi-lumen balloon catheter having a proximal catheter end, a balloon having a proximal balloon end and defining a balloon interior to be inflated with an inflation fluid, a hollow inflation lumen extending through the catheter to the balloon interior and shaped to convey the inflation fluid to and from the balloon interior, a hollow drain lumen parallel to the inflation lumen, and a balloon drainage port fluidically connecting the balloon interior to the drain lumen, and a stretch valve having a hollow base fixed in the drain lumen adjacent the proximal catheter end and shaped to permit a fluid to pass therethrough and a hollow plug shaped to permit a fluid to pass therethrough and slidably positioned in the drain lumen at a given distance from the base to, in a steady state, prevent the inflation fluid from passing through the drainage port and, in a stretched state when a length between the proximal catheter end and the proximal balloon end is elongated between approximately 5 percent and approximately 200 percent, the plug slides within the drain lumen to permit the inflation fluid to pass through the drainage port and into the drain lumen, and a connector connected to the base and to the plug and having a length greater than the given distance. The balloon drainage port has an axis perpendicular to the longitudinal axis of the catheter.

With the objects of the invention in view, there is also provided a safety urinary catheter including a safety urinary catheter including a stretch valve, a connector, and a flexible, multi-lumen balloon catheter. The flexible, multi-lumen balloon catheter has a proximal catheter end, a balloon having proximal and distal balloon ends and defining a balloon interior to be inflated with an inflation fluid, a hollow inflation lumen extending through the catheter to the balloon interior and shaped to convey the inflation fluid to and from the balloon interior, a hollow drain lumen parallel to the inflation lumen, and a balloon drainage port fluidically connecting the balloon interior to the drain lumen. The stretch valve has a base fixed in one of the inflation lumen and the drain lumen adjacent the proximal catheter end at a given distance from the balloon drainage port and shaped to permit a fluid to pass thereby, a plug shaped to block the balloon drainage port when installed therewithin and prevent fluid from passing through the balloon drainage port, and a connector connected to the base and to the plug and having a length greater than the given distance. When the plug is installed in the balloon drainage port, the plug prevents the inflation fluid from passing through the balloon drainage port and, in a stretched state when a length between the proximal catheter end and the proximal balloon end is elongated between approximately 5 percent and approximately 200 percent, the plug exits the balloon drainage port to permit the inflation fluid to pass therethrough into the drain lumen.

In accordance with another feature of the invention, the connector is inelastic or partially elastic and partially inelastic. The partially elastic portion of the connector can be a spring.

In accordance with an additional feature of the invention, the inflation lumen is fluidically connected to the balloon interior through at least one inflation port.

In accordance with yet an added feature of the invention, the balloon drainage port is a plurality of balloon drainage ports each fluidically connecting the balloon interior to the second lumen.

In accordance with yet an additional feature of the invention, the plurality of balloon drainage ports each fluidically connect at least one of the balloon interior and the inflation lumen to the second lumen and the stretch valve, in the steady state, positions the plug in the second lumen to prevent fluid from passing through the plurality of balloon drainage ports and, in the actuated state, the plug slides within the second lumen to permit the inflation fluid to pass through the plurality of ballon drainage ports.

In accordance with again another feature of the invention, the balloon has a balloon proximal end, the balloon catheter further comprises a stretch portion between the proximal catheter end and the balloon proximal end, and the actuated state of the stretch valve is a stretched state of the stretch portion at a pull force of between approximately 1 pound and approximately 15 pounds applied to the proximal shaft portion.

In accordance with another feature of the invention, the balloon has a balloon proximal end, the balloon catheter further comprises a stretch portion between the proximal catheter end and the balloon proximal end, and the actuated state of the stretch valve is a stretched state of the stretch portion at a pull force of between approximately 1 pound and approximately 5 pounds applied to the proximal shaft portion.

In accordance with yet another feature of the invention, the balloon has a balloon proximal end, the balloon catheter further comprises a stretch portion between the proximal catheter end and the balloon proximal end, and the actuated state of the stretch valve is a stretched state of the stretch portion at a pull force of between approximately 1.5 pounds and approximately 2 pounds applied to the proximal shaft portion.

In accordance with yet a further feature of the invention, when the balloon portion is inflated with a fluid and a pull force of greater than approximately 15 pounds is applied to the stretch portion, the stretch valve meets the stretched state and thereby deflates the inflated hollow balloon portion.

In accordance with yet an added feature of the invention, when the balloon portion is inflated with a fluid and a pull force of greater than approximately 5 pounds is applied to the stretch portion, the stretch valve meets the stretched state and thereby deflates the inflated hollow balloon portion.

In accordance with yet an additional feature of the invention, when the balloon portion is inflated with a fluid and a pull force of greater than approximately 2 pounds is applied to the stretch portion, the stretch valve meets the stretched state and thereby deflates the inflated hollow balloon portion.

In accordance with again another feature of the invention, the base is fixed in the inflation lumen adjacent the proximal catheter end and, when the plug is installed in the balloon drainage port, the plug prevents the inflation fluid from passing through the balloon drainage port and, in a stretched state when a length between the proximal catheter end and the proximal balloon end is elongated between approximately 5 percent and approximately 200 percent, the plug exits the balloon drainage port into the inflation lumen to permit the inflation fluid to pass through the balloon drainage port into the drain lumen.

In accordance with a concomitant feature of the invention, the base is fixed in the drain lumen adjacent the proximal catheter end and, when the plug is installed in the balloon drainage port, the plug prevents the inflation fluid from passing through the balloon drainage port and, in a stretched state when a length between the proximal catheter end and the proximal balloon end is elongated between approximately 5 percent and approximately 200 percent, the plug exits the balloon drainage port into the drain lumen to permit the inflation fluid to pass through the balloon drainage port into the drain lumen.

The low-pressure balloon catheter of the present invention prevents injury by having the balloon automatically deflate before an injury can occur, for example, when being forced to withdraw from the bladder or being forced to inflate within a urethra.

The stretch valve balloon catheter of the present invention prevents injury to patients in various ways. First, the stretch valve balloon catheter of the present invention prevents injury to patients by having the balloon automatically deflate before an injury can occur, for example, when being forced to withdraw from the bladder prior to physician-scheduled manual deflation. Second, the stretch valve balloon catheter of the present invention prevents injury to patients by preventing the balloon from inflating, for example, when being forced to inflate anywhere outside the desired location (e.g., the trachea or the urethra). In the example of a urinary drainage catheter, the stretch valve balloon catheter of the present invention does not dangerously inflate when outside the bladder, such as when in the urethra. Third, the stretch valve balloon catheter of the present invention prevents injury to the catheter and patient by having the balloon automatically partially deflate when overinflated, for example, when a 10 cc balloon is being inflated with 30 cc.

For placement of this catheter in the bladder in the ideal position, an exemplary embodiment described herein provides the physician or technician with a visual aid. In particular, markings visible from the outside of the catheter are placed to indicate average or known lengths of the lumen in which it is to be placed (e.g., the urethra) and they can be different depending on the sex, weight, or height of the patient.

While the catheters of the present invention make it a safer device, e.g., for urinary drainage, the present invention can also be used for any procedures in which balloons are used to occlude or distend cavities or lumens. Examples of these procedures include coronary artery vessels and peripheral vascular vessels, such as the aorta and extremity vessels. Balloon dilations of other lumens, such as ureters, bowel, heart valve annulus, prostate and the esophagus, are also candidates for use of the catheter of the present invention. Further, the mechanism of pressure release can be used for any fluid or air-filled device such as tissue expanders, percutaneous devices, and the like. The inventive aspects described herein are applicable to all of the various balloon catheter examples mentioned herein.

Some of the embodiments of the inventive concepts described herein utilize a valve (e.g., a slit valve or a stretch valve) that permits reuse when utilized. Although, when a urinary catheter is pulled out by a patient, for example, that catheter is typically discarded for sanitary reasons as exposure outside the treatment area places the catheter in contact with bacteria that can be introduced to the patient if reuse occurs. With embodiments having non-resetting valves, the inventive balloon catheters are single use after deflation occurs. Although deflation of such a single-use catheter renders it useless, the act of immediate deflation protects the patient from serious harm and the cost of replacing a catheter is minimal as compared to the significant cost of treating catheter-induced injury. Prevention of such injuries is becoming more and more important because the injuries are commonplace. The increase occurs for a number of reasons. First, a greater percentage of the population is aging. Second, there is a current trend to use less-skilled health care personnel to perform more procedures and to be responsible for treatment, both of which save the hospitals and doctors money. The shortage of nursing professionals (e.g., R.N.s) exacerbates this trend. The present tendency is to use nursing professionals for more functions, such as administration and delivery of medications. This leaves only the least-skilled technicians with the task of taking vital signs and inserting catheters. Under such circumstances, more injuries are likely and do, in fact, occur. Lastly, catheter-related complications are becoming more severe due to the increased use of anticoagulation medication, such as PLAVIX®, that is frequently prescribed in treating cardiovascular disease.

Yet another possible complication arising from the standard Foley catheter is that the balloon will not deflate even when the deflation mechanism is activated. This situation can occur, for example, because the wrong fluid is used to inflate the balloon or when a fluid, such as saline, crystallizes, which happens occasionally. Sometimes, the ability to deflate the balloon is interrupted because the drainage channel used to deflate the balloon becomes obstructed, which is common if the catheter is left in place too long. Remedy of such a scenario involves an invasive procedure, which includes threading a needle or other sharp object somewhere through the body cavity to puncture the balloon and, thus, dislodge the catheter. This procedure is not desirable and is to be avoided if possible. Yet another possible complication can occur when the patient has a stricture, i.e., scar tissue in the urethra that impedes the passage of the catheter. When a technician is faced with a stricture, it seems to the technician that the catheter is no longer moving towards the bladder. Consequently, the technician uses excessive force to push the catheter into the bladder, thereby causing a tear that creates its own lumen into the penile and prostatic tissue. As is self-evident, this situation is accompanied by significant bleeding and the need for additional corrective procedures and surgery.

The valved, auto-deflating inventive balloons described herein further provide a self-regulating feature that prevents over-inflation of the balloon. Additionally, the valved, auto-deflating balloons prevent inflation when the balloon is not placed in an area large enough for complete expansion, e.g., when the balloon of a urinary Foley catheter is inflated within a urethra or the balloon of an endotracheal tube is inflated within a trachea.

With the low-pressure or valved, auto-deflating balloons described herein, the technician, nurse, or doctor merely needs to pull on the catheter to cause the catheter to automatically deflate, thus sparing the patient from any additional surgical procedures.

Added benefits of the catheters described herein do not deal only with safety, significant financial benefits arise as well. It is understood that catheter-induced injuries are much more common than public documentation suggests. Catheter-related trauma occurs no less that once a week in a large metropolitan hospital. Usually, each incident not only increases the patient's hospital stay substantially, but also the expense of the stay. Each incident (which is usually not reimbursed by insurance) can increase the cost to the hospital by thousands of dollars, even tens or hundreds of thousands of dollars. This is especially true when the patient brings a personal injury action against the hospital, physician(s), and/or staff. And, when additional surgery is required to repair the catheter-induced injury, increased expense to the hospital is not only substantial, if litigation occurs as a result of the injury, damages awarded to the patient can run into the millions of dollars. In situations where a safety catheter, such as the ones described herein, are available but the hospital or physician decides not to use it and, instead, uses a standard catheter, the chance that punitive damages are awarded in litigation increases exponentially. The catheters and methods described herein, therefore, provide safer catheters that have the possibility of saving the medical industry billions of dollars.

To prevent urethra tearing occurrences due to premature-improper inflation of the balloon and/or due to premature removal of an inflated balloon, an exemplary embodiment provides various balloon safety valves. Such valves are configured to release the inflation liquid from the balloon before injury occurs.

The maximum stress that a typical urethra can take without tearing and/or breaking is known and is referred to as a maximum urethra pressure. It is also possible to calculate how much pressure is exerted upon the exterior of a balloon of a balloon catheter by measuring the pressure required to inflate the balloon. Knowing these two values, it is possible to construct a balloon that breaks rapidly and/or ceases inflation if the maximum urethra pressure is exceeded.

For example, in a first exemplary embodiment, the balloon, which is typically some kind of rubber, silicone, elastomer, or plastic, can be made with a breaking point that instantly deflates the balloon if the pressure in the balloon exceeds the maximum urethra pressure. It is acknowledged and accepted that, once the balloon breaks, this catheter is useless and must be discarded because the cost of patient injury far outweighs the cost of the disposable catheter. Also, such a balloon is limited to inflation with a bio-safe fluid to prevent unwanted air/gas from entering the patient. If, however, air or other gas will not injure the patient, the fluid can be air or another gas.

As an alternative to a one-use breaking safety valve, a multi-use pressure valve can be added to the balloon inflation lumen and can be set to open into the drainage lumen if the maximum urethra pressure is exceeded in the balloon or the balloon inflation lumen. Such a valve can be located near or at the balloon inflation port, for example. Any combination of the above embodiments is envisioned as well.

Another exemplary embodiment of the present invention provides the catheter with a balloon that inflates with virtually no pressure. As used herein, "virtually no pressure," "zero-pressure" and "low-pressure" are used interchangeably and are defined as a range of pressure between approximately standard atmospheric pressure and 0.3 atmospheres (5 psig). This is in contrast to "high-pressure," which is greater than approximately 1.5 atmospheres (22 psig). With such a configuration, the zero-pressure balloon can be deflated with virtually no force. As such, when the clinician attempts to inflate the zero-pressure balloon of the present invention within a urethra, the balloon simply does not inflate. Likewise, when the already inflated balloon within the bladder is forced into the urethra, such deflation needs virtually no pressure to collapse the balloon to fit into the urethra. In both circumstances, injury to the urethra is entirely prevented.

Further exemplary embodiments that prevent urethra tearing occurrences due to premature removal of an inflated balloon or inflation outside the treatment area provide a balloon catheter with a stretch valve and methods for manufacturing and using such a valved catheter. In these variations, the invention takes advantage of the fact that premature removal of the inflated balloon catheter requires stretching of the catheter at the proximal side of the balloon. The valved catheter can be configured with a release mechanism that is a function of elongation. With short elongations, the balloon remains inflated. However, when pulled beyond a preset limit, the valve automatically opens and drains the fluid filling the balloon. The existence of the stretch valve also provides the ability to control and eliminate over-inflation. When the balloon is over-inflated, the ends of the balloon (distal and proximal) move away from each other. As this movement occurs, the stretch valve begins to actuate, thereby deflating the balloon until the proximal and distal ends no longer stretch the balloon. When these ends are no longer stretched, the valve closes automatically, thereby preventing further deflation of the previously over-inflated balloon. The existence of the stretch valve also provides the ability to control and eliminate inflation when constricted. For example, when the balloon of the stretch-valve safety catheter is attempted to be inflated within the confines of a urethra, in addition to stretching in the radial direction, the balloon also stretches in the longitudinal direction—the same direction as the actuation axis of the stretch valve. This stretching causes the stretch valve to open prior to causing significant damage to the lumen in which the balloon is being inflated (e.g., the urethra), thereby directing the inflation fluid into the drain lumen instead of the balloon.

In all standard uses of a balloon catheter, the inflation fluid remains in a closed system. When inflated, the inflation fluid only enters the inflation lumen and the interior of the balloon. When so inflated, the inflation fluid never exits the inflation lumen or the balloon until the health professional or user specifically deflates the balloon, typically with a syringe similar to the one that was used to the inflate the balloon in the first place. The various balloon catheters described herein, however, do not possess a closed, balloon-inflation system. For the described low-pressure catheter, the inflation fluid is permitted to exit out the proximal and/or the distal ends of the balloon into the environment outside the balloon. For the herein-described catheters with slit, stretch, or other internal valves, the inflation fluid is permitted to exit into the drainage lumen, which is fluidically connected to the external drainage bag and to the drainage opening at the distal tip of the catheter and, thereby, the bladder or other expanse in the body. Likewise, for the herein-described catheters with stretch valves, the inflation fluid is permitted to exit into the drainage (or inflation) lumen.

It is known that a technician/physician/user inserting a balloon catheter does not know where the balloon is placed within the body after the balloon is inserted therein. It is also known that approximately 25% of patients who are admitted to a hospital will have an indwelling catheter at some point during their stay and 7% of nursing home residents are continually managed by long term catheterization. Over 4,000,000 indwelling urinary balloon catheters are inserted in U.S. patients every year and over 25,000,000 are sold in the U.S. every year. Only with radiographic or sonographic equipment can the balloon portion of the catheter be visualized within the body. This type of visualization is simply too expensive to use every time, for example, a urinary catheter is used.

The difference from standard closed-system balloon catheters of the herein-described safety catheters provides unique benefits not found elsewhere or before. More specifically, only with the inventive safety catheters described herein does the inflation fluid have the opportunity to exit the balloon. When the inflation fluid exits the balloon of these safety catheters, it provides a unique and automatic way of informing the user or health-care professional that a dangerous condition has just been prevented. More specifically, if the inflation fluid contains an inert colorant that is different from any color of fluid that typically is drained by the balloon catheter, the herein-described safety catheters will show, visually and immediately, either that an attempt has been made to inflate the balloon within a constricted lumen (such as the urethra) or that the catheter has been stretched enough to cause the stretch-valve of the inserted balloon to act and prevent possible pull-out injury. In the former case, if the balloon is attempted to be inflated within a constricted lumen (e.g., urethra) and not in the larger treatment area (e.g., bladder), then the inflation fluid will, upon the attempted inflation, be almost immediately apparent to the user/health-care professional when it drains directly into the drainage bag. When the user/health-care professional sees the color in the drainage bag, he/she knows that the balloon is not correctly placed and corrective action can be taken immediately and before injury or further injury occurs. In the latter case, if the catheter is pulled by the patient or by catching the environment, and the catheter is not completely removed from the patient, at least some or all of the inflation fluid will drain into the drainage bag. When that bag is next inspected by the user/health-care professional, it will be immediately apparent that something is wrong and that the catheter needs examination and/or removal and replacement. Some variations herein allow the balloon to even be refilled if deflation occurs without any injury and if the catheter is not pulled out sufficiently far to require replacement. In any case, injury is prevented.

The invention is not limited to this visual aid for indicating to a physician, nurse, or technician that the catheter has been installed improperly. For male and female patients, it is known approximately how far the catheter needs to be inserted into the urethra because average urethra lengths for males and females are known. With this information, the catheter described herein can be provided with external markings indicating those average urethra lengths. Even if the catheters are not male or female specific, both indications can be provided on a given catheter. In this way, if, after believing that insertion is "correct," the user still sees the marking outside the patient, the user can double check the insertion before inflating the balloon (which would occur within the urethra if not installed far enough therein). Additionally, these markings can provide immediate visual indications to medical personnel when it is not known that a patient has jerked out the catheter partially or the catheter snagged on the environment and was pulled out partially. In either situation, if the medical personnel looks at the catheter and sees the markings, then it becomes immediately clear that the inflated balloon catheter has been improperly removed, but partially, and immediate corrective action can be taken.

Description of one exemplary embodiment herein in a way that separate from other exemplary embodiments is not to be construed mean that the one embodiment mutually exclusive of the other exemplary embodiments. The various exemplary embodiments of the safety catheters mentioned herein can be used separately and individually or they can be used together in any combination.

Although some variations are illustrated and described herein as embodied in a stretch valve balloon catheter and methods for producing and using such a catheter, they are, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before further disclosure and description, it is to be understood that the terminology used herein is for the purpose of describing particular embodiments only and is not intended to be limiting. The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the catheter. Lastly, the term "proximal" refers to the end of the catheter closest to the person inserting the catheter and is usually that end of the catheter with a hub. The distal end of the catheter is the end furthest away from the person inserting the catheter.

BRIEF DESCRIPTION OF THE DRAWINGS

In the following, the invention will be described in more detail by exemplary embodiments and the corresponding figures. By schematic illustrations that are not true to scale, the figures show different exemplary embodiments of the invention.

FIG. 21 is a fragmentary, enlarged, longitudinal cross-sectional view of a balloon portion of an exemplary embodiment of an automatically deflating, stretch valve urinary balloon catheter according to the invention with the balloon in an uninflated state;

FIG. 22 is a fragmentary, enlarged, longitudinal cross-sectional view of the automatically deflating, stretch valve urinary balloon catheter of FIG. 21 with the balloon in an inflated state and with the stretch valve in an unactuated state;

FIG. 23 is a fragmentary, enlarged, longitudinal cross-sectional view of the automatically deflating, stretch valve urinary balloon catheter of FIG. 21 with the balloon in an inflated state and with the stretch valve in an actuated state;

FIG. 27 is a fragmentary, enlarged, longitudinal cross-sectional view of a balloon portion of still another exemplary embodiment of an automatically deflating, stretch valve urinary balloon catheter according to the invention with the balloon in an uninflated state;

FIG. 28 is a fragmentary, enlarged, longitudinal cross-sectional view of the automatically deflating, stretch valve urinary balloon catheter of FIG. 27 with the balloon in an inflated state and with the stretch valve in an unactuated state;

FIG. 29 is a fragmentary, enlarged, longitudinal cross-sectional view of the automatically deflating, stretch valve urinary balloon catheter of FIG. 27 with the balloon in an inflated state and with the stretch valve in an actuated state;

FIG. 37 is a fragmentary, enlarged, longitudinal cross-sectional view of a balloon portion of another exemplary embodiment of an automatically deflating, stretch valve urinary balloon catheter according to the invention with the balloon in a partially inflated state and the stretch valve in an unactuated state;

FIG. 38 is a fragmentary, enlarged, longitudinal cross-sectional view of a balloon portion of still another exemplary embodiment of an automatically deflating, stretch valve urinary balloon catheter according to the invention with the balloon in a partially inflated state and the stretch valve in an unactuated state;

FIG. 44 is an enlarged, perspective view of an exemplary embodiment of a stretch valve for a urinary balloon catheter according to the invention;

FIG. 45 is a fragmentary, enlarged, longitudinal cross-sectional view of a balloon portion of an automatically deflating, stretch valve urinary balloon catheter with the stretch valve of FIG. 44 in an unactuated state and with the balloon in a partially inflated state;

FIG. 46 is an enlarged, perspective view of another exemplary embodiment of a stretch valve for a urinary balloon catheter according to the invention;

FIG. 47 is a fragmentary, enlarged, longitudinal cross-sectional view of a balloon portion of an automatically deflating, stretch valve urinary balloon catheter with the stretch valve of FIG. 46 in an unactuated state and with the balloon in a partially inflated state;

DETAILED DESCRIPTION OF THE EXEMPLARY EMBODIMENTS

Figure 1:
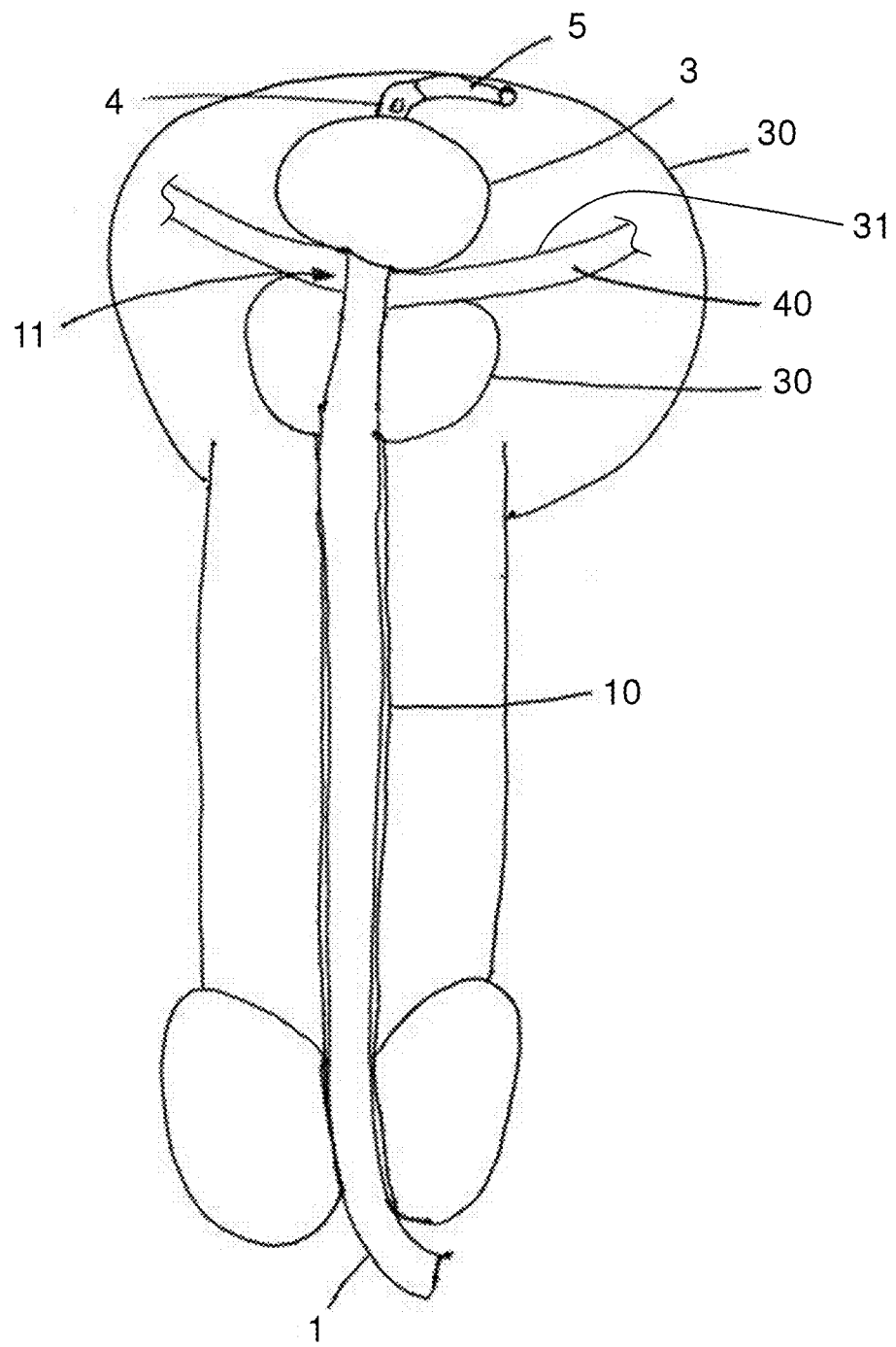
FIG. 1 is a diagrammatic, fragmentary, longitudinal cross-sectional view of a prior art catheter ideally placed in a urethra and a bladder of a male patient.

While the specification concludes with claims defining the features of the invention that are regarded as novel, it is believed that the invention will be better understood from a consideration of the following description in conjunction with the drawing figures, in which like reference numerals are carried forward.

Herein various embodiment of the present invention are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Figure 2:
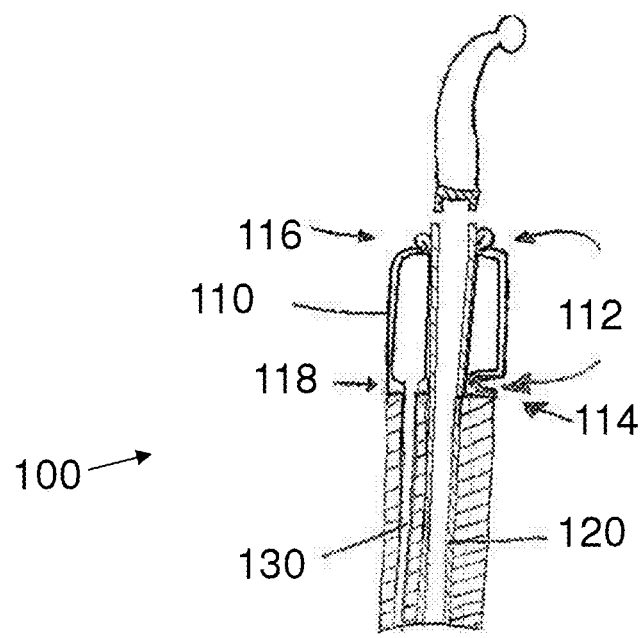
FIG. 2 is a fragmentary, enlarged, longitudinal cross-sectional view of a distal portion of a first embodiment of a pressure-limiting balloon catheter according to the invention.

Referring now to the figures of the drawings in detail and first, particularly to FIG. 2 thereof, there is shown a first embodiment of a pressure-limiting balloon catheter 100 that does not inflate past the tearing limit of a lumen in which the catheter 100 is placed, for example, in the urethra.

To prevent occurrences of urethra tearing due to premature-improper inflation of the balloon and/or due to premature removal of an inflated balloon, the invention of the instant application provides the balloon 110 with a balloon safety valve 112. As set forth above, in a balloon 3 of a conventional catheter (see reference numerals 1 to 5 in FIG. 1), the high-pressure balloon 3 is fixed to the outer surface of the fluid drainage lumen 120 (not shown in FIG. 1) and is not intended to be removed therefrom or to burst thereon unless an extraordinary amount of inflation occurs. Such a tearing event is not supposed to occur under any circumstances during use with a patient. If such an event happens, the material of the balloon 3 will open at a random location, based upon the microscopic fractures or weaknesses in the material itself, and risk serious damage to the patient associated with the bursting, as well as a risk of balloon fragmentation, which could leave one or more pieces of the balloon 3 inside the patient after removal of the catheter 1.

In contrast to such conventional devices, the balloon 110 of the present invention is created specifically to tear when a predefined pressure exists in or is exerted on the balloon 110. The controlled tear will occur because the balloon safety valve 112 is present. Conventional balloons have constant balloon wall thicknesses (before inflation). In contrast thereto, the balloon safety valve 112 in the first embodiment is a defined reduction in balloon wall thickness. This reduction creates a breaking point or selected breaking points at which the balloon 110 is intended specifically to break when a predefined force exists in or is imparted on the balloon 110. Because the balloon 110 is made of a material having a known tearing constant—dependent upon the thickness thereof (which is determined experimentally for different thicknesses of a given material prior to use in a patient), the balloon safety valve 112 of the present invention for urethra applications is matched to break when the pressure inside or exerted on the balloon 110 approaches the maximum urethra pressure.

In the embodiment shown in FIG. 2, a decreased thickness is formed as a first semi-circumferential groove 114 near a proximal end of the balloon 110 and/or as a second semi-circumferential groove 116 near a distal end of the balloon 110. The grooves 114, 116 can have any cross-sectional shape, including, trapezoidal, triangular, square, or rectangle, for example. Because rubber, plastic, and silicone materials tear well with thinner cuts, a relatively triangular shape or one with a narrow bottom can be an exemplary configuration. To make sure that the entire balloon 110 of the illustrated embodiment does not completely tear away from the fluid drainage lumen 120, both grooves 114, 116 do not extend around the entire circumference of the balloon 110. As shown to the left of the proximal groove 116 in FIG. 2, the groove 116 is not present on at least an arc portion 118 of the circumference of the balloon 110. The arc portion is defined to be sufficiently large so that, when the catheter 100 is removed from the patient, the balloon 110 cannot tear away entirely from the catheter 100 (and create the disadvantageous fragmentation situation as set forth above). The illustrated balloon safety valve 112 is, therefore, fashioned to keep the balloon 110 in one piece after breaking and remain firmly connected to the catheter 100 to insure that no piece of the balloon 110 will be left inside the patient after actuation of the balloon safety valve 112. Alternatively, the groove can be along the length of the balloon parallel to the axis of the catheter. This groove can be made by skiving the balloon after attaching to the catheter or by skiving the balloon as it is formed during extrusion or dip molding. In this embodiment, when the pressure exceeds a predetermined limit, the balloon splits along the groove without releasing fragments.

Figure 3:
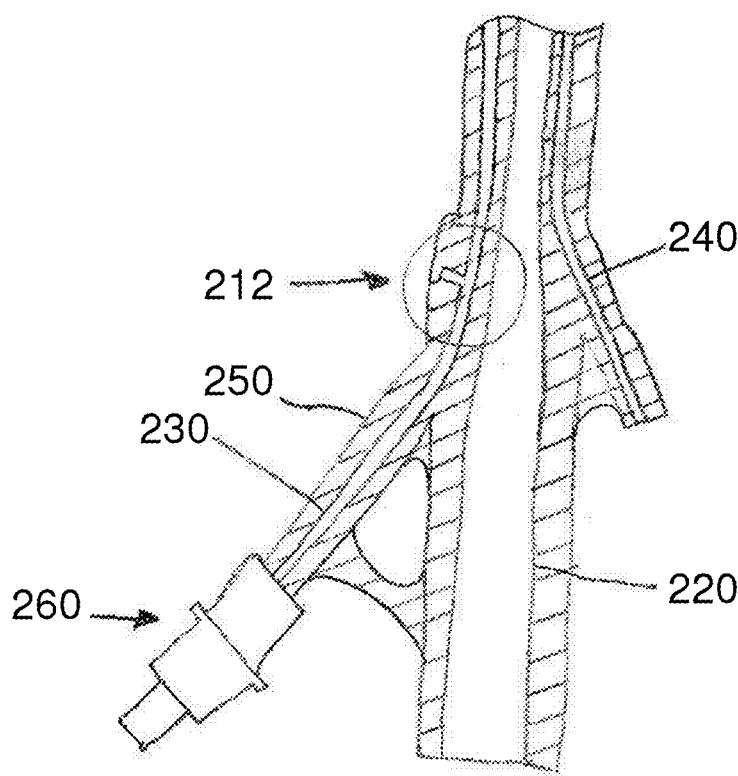
FIG. 3 is a fragmentary, enlarged longitudinal cross-sectional view of a proximal portion of a second embodiment of a pressure-limiting balloon catheter according to the invention.

It is noted that the balloon 110 is inflated through an inflation lumen 130 having a proximal opening, typically formed by one end of a luer connector (see 260 in FIG. 3). The illustrated end is connected to a non-illustrated inflation device, for example, a distal end of a syringe for inflation of the balloon 110.

In this first embodiment, the balloon can be of an elastomer, rubber, silicone, or plastic, for example. Once the balloon breaks, the catheter is useless and must be discarded. Because the balloon 110 in this embodiment will break inside the patient, it should be inflated with a bio-safe fluid to prevent unwanted air, gas, or bio-unsafe fluid from entering the patient. In certain circumstances where balloon catheters are used, air or gas will not injure the patient if let out into the patient's body cavity. In such circumstances, the inflating fluid can be air under pressure, for example.

Maximum urethra pressure can also be tailored to the individual patient. Based upon a urethral pressure-measuring device, the patient's maximum urethra pressure can be measured before the catheter 100 is placed therein. A set of catheters 100 having different safety valve breaking constants can be available to the physician and, after estimating or calculating or knowing the patient's maximum urethra pressure, the physician can select the catheter 100 having a safety valve breaking constant slightly or substantially smaller than the patient's maximum urethra pressure. Accordingly, if the pressure in the balloon 110 approaches the patient's maximum urethra pressure for any reason, whether it is due to over-inflation, improper placement, and/or premature removal, the balloon 110 is guaranteed to break prior to the patient's lumen (in particular, the patient's urethra) and, therefore, prior to causing injury.

A second embodiment of the one-use breaking safety valve of a pressure-limiting balloon catheter 200 is shown in FIG. 3. The catheter 200 has a fluid drainage lumen 220, a balloon inflation lumen 230, and a secondary lumen 240.

The fluid drainage lumen 220 is connected fluidically to the body cavity (i.e., the bladder 30) for draining fluid from the body cavity.

The secondary lumen 240 can be used for any purpose, for example, for housing the radiation line that will supply energy to the radiation coil 2. It can also be used for injecting fluid into any distal part of the catheter 200 or even the body cavity itself.

The balloon inflation lumen 230 begins at a proximal end with an inflating connector 260 that, in an exemplary embodiment, is one part of a luer connector. The balloon inflation lumen 230 continues through the body of the catheter 200 all the way to the balloon 110 and is fluidically connected to the interior of the balloon 110.

Alternatively or additionally, the balloon safety valve is fluidically connected to the balloon inflation lumen 230. In a second embodiment of the safety valve 212, the valve 212 is formed integrally with the balloon inflation lumen 230 and is set to open into the environment (instead of into the patient) if the maximum urethra pressure is exceeded in the balloon 110 or the balloon inflation lumen 230. Alternatively and not illustrated, the valve 212 is formed integrally with the balloon inflation lumen 230 and is set to open into the drainage lumen 220 if the maximum urethra pressure is exceeded in the balloon 110 or the balloon inflation lumen 230. A further alternative includes opening both into the environment and into the drainage lumen 220. Because this safety valve 212 is located near or at the balloon inflation port 260 in this configuration, fluid used to inflate the balloon will not enter the patient when the valve 212 opens.

Figure 4:
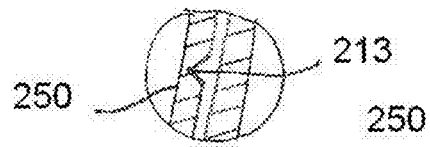
FIG. 4 is a fragmentary, enlarged, cross-sectional view of a first alternative configuration of the safety valve of FIG. 3.
Figure 5:
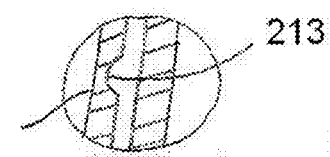
FIG. 5 is a fragmentary, enlarged, cross-sectional view of a second alternative configuration of the safety valve of FIG. 3.
Figure 6:
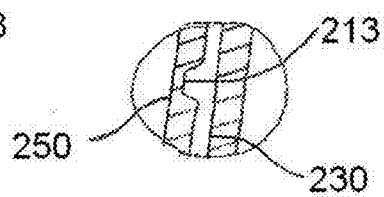
FIG. 6 is a fragmentary, enlarged, cross-sectional view of a third alternative configuration of the safety valve of FIG. 3.

The safety valve 212 in the second embodiment can merely be a narrowing of the distance between the balloon inflation lumen 230 and the outer surface 250 of the catheter 220. In FIG. 3, the valve 212 has a rectangular cross-section and extends away from the balloon inflation lumen 230. As shown in FIGS. 4, 5, and 6, respectively, the cross-section can be triangular (peaked or pyramidical in three-dimensions), curved (circular or cylindrical in three-dimensions), or trapezoidal (frusto-conical or bar-shaped in three-dimensions). The cross-sections are shown in FIGS. 3 to 7 with the narrowing emanating from the balloon inflation lumen 230 outward. As an alternative, the narrowing can begin on the outer surface of the catheter and extend inwards towards the balloon inflation lumen 230. A further alternative can have the narrowing extend from both the inner lumen 230 and the outer surface of the catheter.

Figure 7:
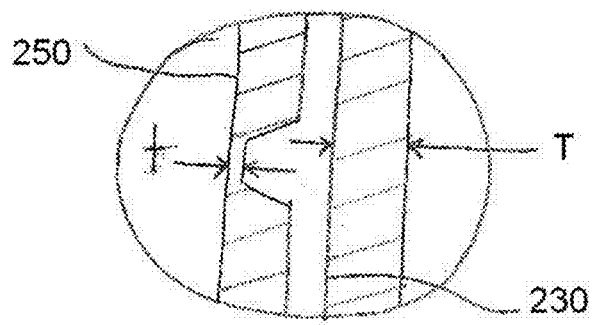
FIG. 7 is a fragmentary, further enlarged, cross-sectional view of the safety valve of FIG. 6.

The cross-sections illustrated are merely exemplary. What is important is that the thickness t between the bottom 213 of the valve 212 and the outer surface 250 of the catheter 220 in comparison to the thickness T of the catheter body over the remainder of the balloon inflation lumen 230. An enlarged view of this thickness comparison is illustrated in FIG. 7. As long as the thickness t is smaller than the thickness T (t<T), and as long as the force $F_b$ required to break the balloon is greater than the force $F_{sv}$ required to break the portion 213 of the safety valve 212 ($F_b$>$F_{sv}$), then the portion 213 of the safety valve 212 is virtually guaranteed to break every time pressure exerting a force F in the balloon inflation lumen 230 is greater than the force $F_{sv}$ required to break the safety valve ($F_{sv}$>F).

Based upon this analysis, the force $F_{sv}$ required to break the safety valve can be tuned to whatever a patient needs or a physician desires and different sized valves can be available for any procedure and provided in the form of a kit. Whether a standard maximum urethra pressure is used or a patient-specific maximum urethra pressure is measured and used, experiments can be conducted prior to use on a patient on various catheter thicknesses t to determine the pressure needed to break the portion 213 of the safety valve 212. For example, ten different maximum urethra pressures can be known as desirable set points and the thicknesses t can be varied such that pressure required to break the ten thicknesses correspond to the ten set point pressures. If, then, ten catheters are placed in such a kit, each having one of the ten thicknesses, then the physician has a range of 10 maximum urethra pressure values to use with the patient.

Although FIGS. 3 to 7 show indentations into the wall of the catheter, the indentation can be in the form of a through-hole entirely through the wall of the catheter communicating with the outside of the catheter over which is placed a sleeve. Depending upon the pressure in the inflation lumen, fluid can leak through the hole and lift up the sleeve and leak to atmosphere therefrom. Pressure is controlled in this embodiment by the modulus of the sleeve material. A harder sleeve that fits snugly on the catheter will not allow leakage at low pressure. Alternatively, a softer rubbery sleeve would lift up easily to release high pressure fluid.

The safety valve 212 of the second embodiment need not be confined to the body of the catheter 200. Instead, the inflating connector 260 can, itself, be equipped with the pressure relief valve 212. Alternatively, a non-illustrated modular attachment containing the safety valve 212 can be attached to the inflating connector 260. Such a modular valve attachment is removable and replaceable (such as through a conventional luer or even a screw-threaded connection). Accordingly, as long as the catheter 200 can still be used after the valve 212 actuates (breaks), the used modular valve attachment can be replaced with a new attachment. The converse is also true for reuse of the attachment if the catheter 200 breaks and the valve of the attachment remains unbroken. A downstream end of the modular valve attachment (e.g., shaped as part of a luer connector) is attached removably to an upstream end of the inflating connector 260 and the upstream end of the modular valve attachment is to be connected to the balloon inflation device, which is commonly a syringe. The upstream end of the modular valve attachment is, likewise, part of a luer connector for easy connection to standard medical devices. In such a configuration, the safety valve 212, 312 of the present invention can be entirely separate from the catheter 200, 300 and, therefore, form a retrofitting device for attachment to any luer connector part present on conventional catheters.

Figure 8:
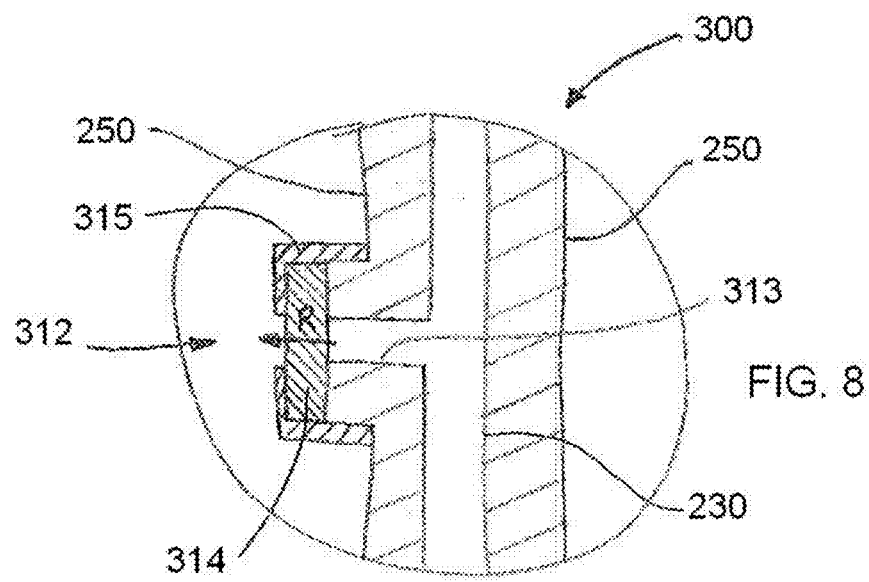
FIG. 8 is a fragmentary, further enlarged, cross-sectional view of a fourth alternative configuration of the safety valve of FIG. 3.

As an alternative to the one-use breaking safety valve of the second embodiment, a multi-use pressure valve can be used. This third embodiment of the pressure-limiting balloon catheter 300 is illustrated in FIG. 8. The catheter 300 can be the same as the catheter 200 in FIG. 3 except for the portion illustrated in FIG. 8. Instead of having a narrowing thickness t of the lumen wall, the valve portion 313 extends entirely to the environment (and/or into the drainage lumen 220). However, a one-way valve 314 (shown only diagrammatically in FIG. 8) is attached to the open end of the valve portion 313 and is secured to the outer surface 250 of the catheter 300 to close off the open end of the valve portion 313. The one-way valve 314 can be secured directly to the outer surface 250 (e.g., with an adhesive), or a connector 315 (e.g., a threaded cap) can secure the one-way valve 314 to the open end of the valve portion 313. Regardless of the configuration, the one-way valve 314 includes a device that does not permit fluid from exiting the lumen 230 until a given resistance R is overcome. This given resistance R can be selectable by the physician depending upon the one-way valve that is chosen for use if a set of one-way valves having different resistances R are available for use by the physician. Just like the second embodiment, the resistance R can be set to correspond to desired maximum urethra pressure values. Therefore, when used, the fluid exits the one-way valve 314 into the environment well before the patient's maximum urethra pressure is exceeded by the balloon.

The one-way valve 314 can be a mechanical one-way valve. Additionally, the one-way valve 314 can be a material having a tear strength corresponding to a desired set of resistances R. The material can be a fluid-tight fabric, a rubber, a plastic, or silicone different from the material making up the catheter. The material can even be a rubber, plastic, or silicone the same as the material making up the catheter but having a reduced thickness t than the thickness T of the catheter. Alternatively, the one-way valve 314 can be a slit valve. Various exemplary embodiments of such a valve can be found in U.S. Pat. No. 4,995,863 to Nichols et al., which is hereby incorporated herein by reference in its entirety.

It can also be appreciated that the pressure release (or relief) valve can be a conventional pressure release valve comprised of a housing with a lumen, a ball, and a spring within the lumen wherein the spring presses the ball against a defined opening. When pressure on the ball exceeds the force of the spring, the ball moves away from the defined opening and fluid moves around the ball and vents to atmosphere. By controlling tension on the spring, the pressure at which the valve releases pressure can be controlled. It can also be appreciated that the pressure release valve can be coupled to a Luer connector, which can be coupled to a one-way check valve that can be used to inflate the balloon as is often used in conventional urinary drainage catheters.

Because the safety valve 212, 312 is located at the proximal end of the catheter 200, 300, the distal end of the catheter 200, 300 can take the form of a distal end of a conventional balloon catheter 2, 3, 4, 5. Alternatively, the distal end shown in FIG. 2 can also be used for redundant over-pressure protection.

Figures 9, 10:
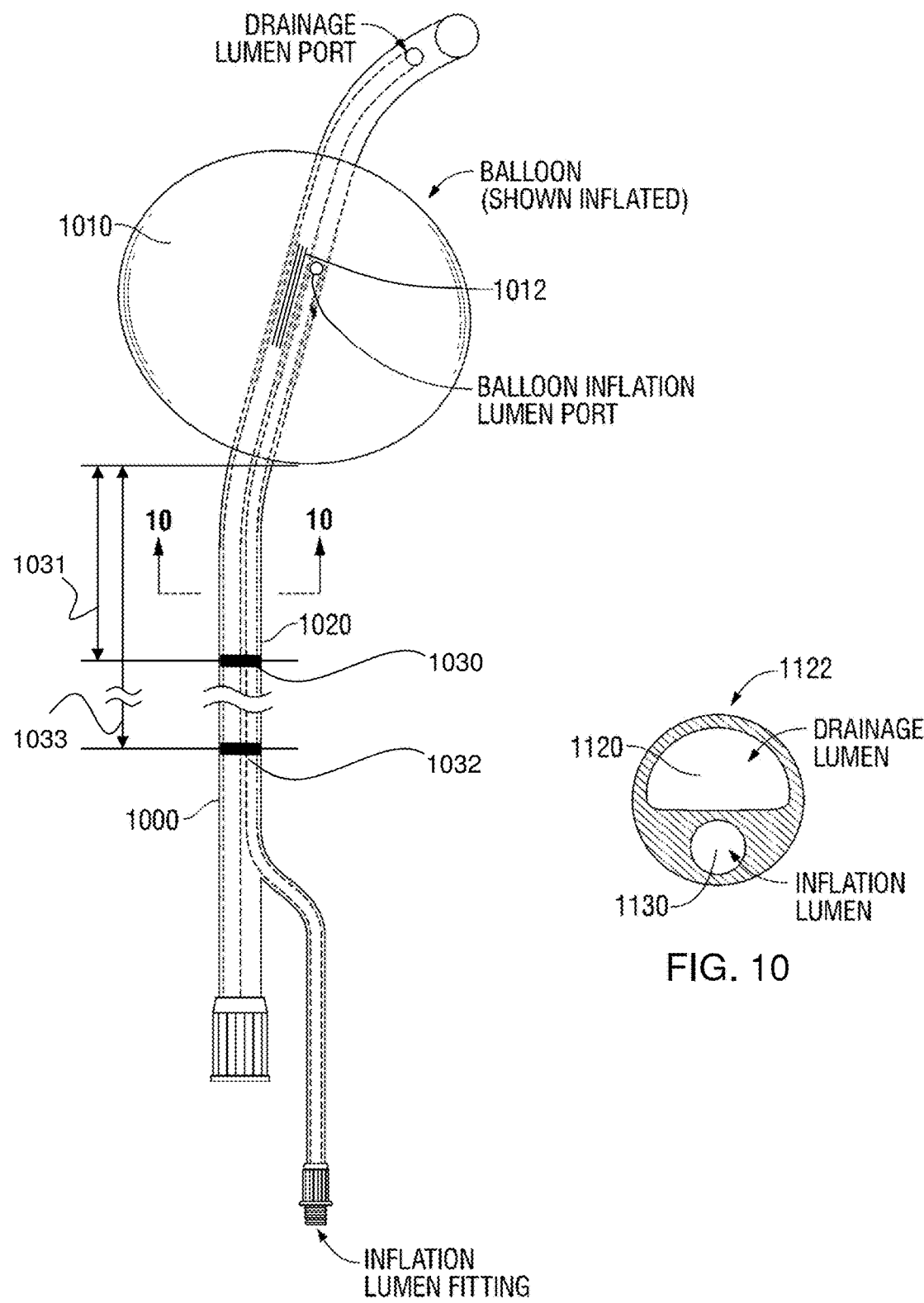
FIG. 9 is a fragmentary, partially hidden, perspective view of an exemplary embodiment of a zero-pressure safety catheter according to the invention.
FIG. 10 is a radial cross-sectional view of a portion of the catheter of FIG. 9 at section line 10-10.
Figure 11:
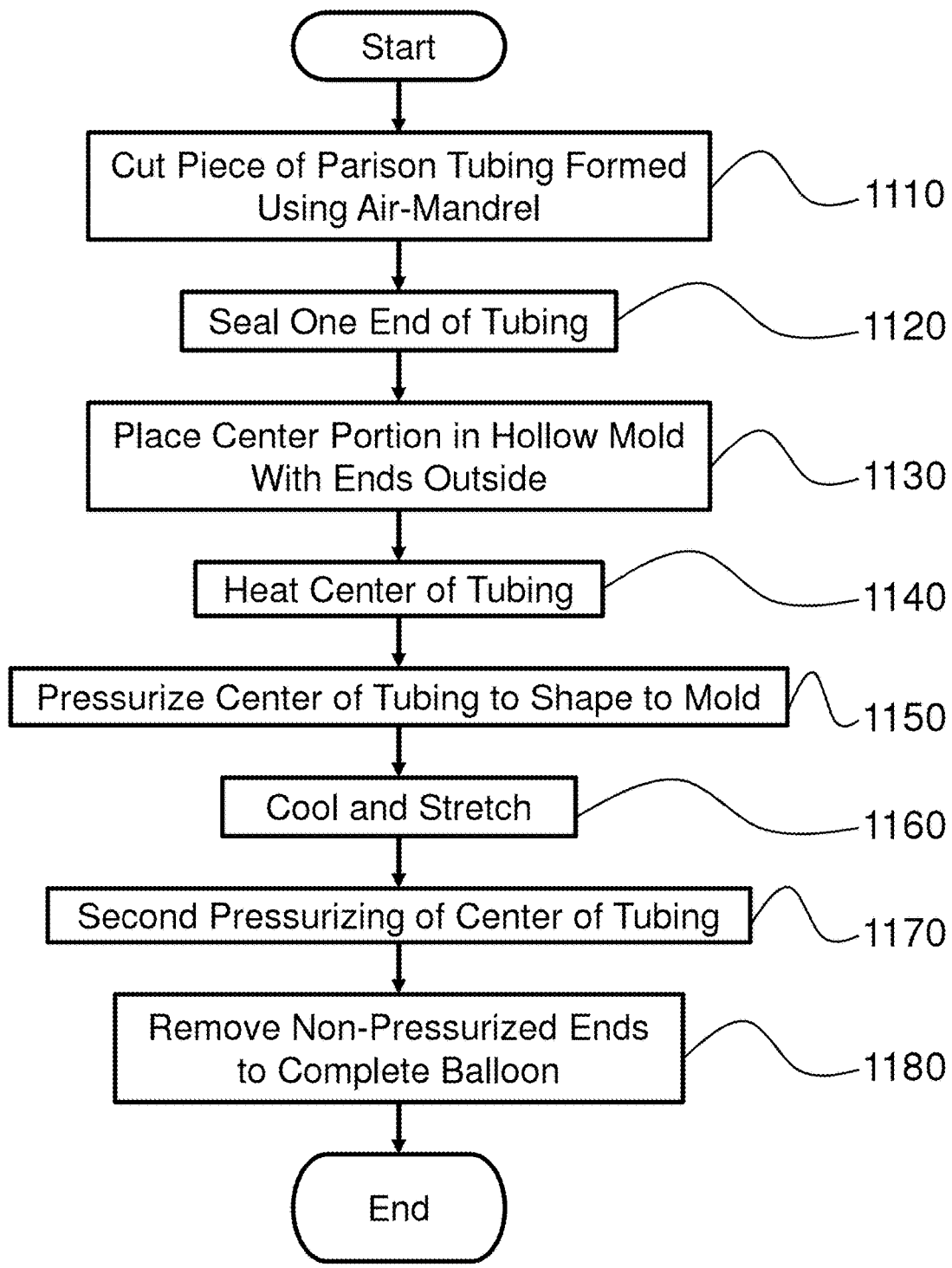
FIG. 11 is a process flow diagram of an exemplary method of forming a zero-pressure balloon according to the invention.
Figure 12:
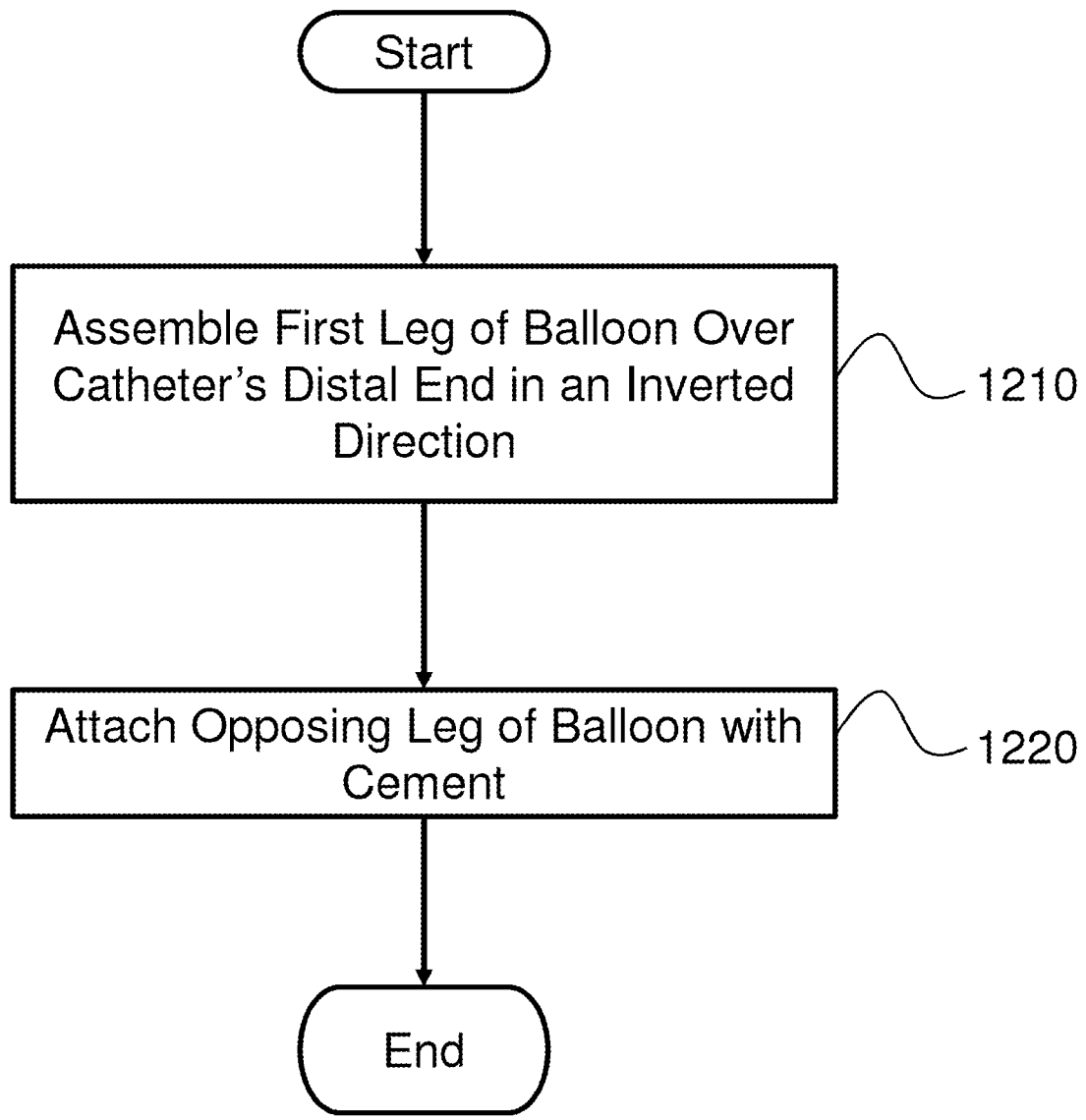
FIG. 12 is a process flow diagram of an exemplary method of attaching a zero-pressure balloon according to the invention.
Figure 13:
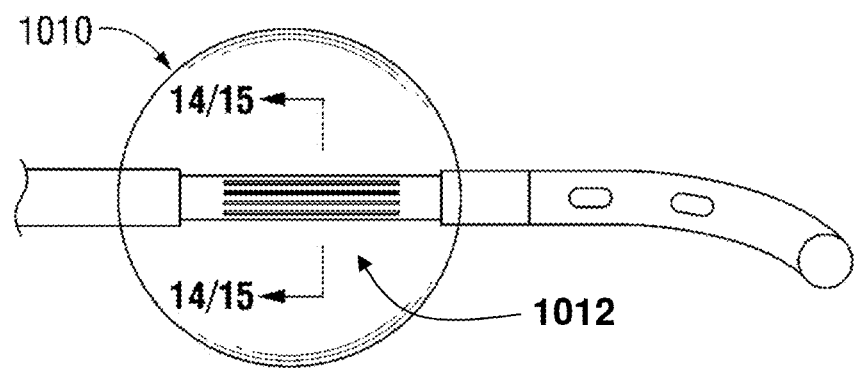
FIG. 13 is a fragmentary, enlarged, perspective view of a distal portion of an exemplary embodiment of a zero-pressure catheter according to the invention.

In another exemplary embodiment of the present invention, FIGS. 9 to 18 illustrate alternatives to the elastomeric balloon described above. In particular, the above elastomeric balloon is replaced by a thin walled, pre-formed, fixed diameter balloon 1010 that inflates with virtually no pressure and withstands pressures between approximately 0.2 atmospheres (2.9 psi) and 0.5 atmospheres (7.35 psi), the latter of which is approximately equal to the maximum urethra pressure, without an appreciable increase in diameter. Examples of such balloon materials and thicknesses are used in the medical field already, such as those used in angioplasty. Other exemplary materials can be those used in commercial (party) balloons, for example, MYLAR®, or similar materials such as nylon, PTA, PTFE, polyethylene and polyurethane, for example. In FIGS. 9 and 13, the balloon 1010 is shown in a spherical shape. However, the balloon 1010 can be, for example, cylindrical with flat or conically tapering ends.

The inflation balloon 1010 can be formed by heating a tubular material within a mold or by heat-sealing thin sheets to one another (e.g., party balloons have two sheets). One example of the relatively non-compliant, thin-walled balloon 1010 of the present invention is formed using a blow-molding process. In the blow-molding process, a thermoplastic material such as nylon, polyurethane, or polycarbonate is extruded or formed into a hollow, tube-like shape (parison) and is subsequently heated and pressurized, usually with air, inside a hollow mold having a shape to form the final outer dimensions of the balloon. An example of the blow molded product is the common plastic soda or water bottle containers.

One exemplary, but not limiting, process to form the zero-pressure balloon of the present invention is described with respect to FIG. 11 and includes, in Step 1110, cutting a relatively short piece of "parison" tubing that is formed using standard "air-mandrel" extrusion techniques. In Step 1120, one end of the tubing is sealed. The center portion of the tubing is placed in a hollow mold, leaving both ends extending outside of the mold in Step 1130. The center of the tubing is heated in Step 1140 with a hot stream of air through a small hole in the center of the mold for a few seconds to soften the tubing walls within the mold. The inside of the tubing is pressurized with a fluid, e.g., air, in Step 1150 to stretch the tubing walls to conform to the inside dimensions of the mold. After a short cooling period, an additional stretch of the formed balloon is done in Step 1160 by pulling on the (external) parison and, after a second "blowing" in the same mold in Step 1170, is used to create a very thin-walled balloon (much less than 0.001 inches, typically, based upon the parison wall thickness and the final balloon diameter). The extra (unblown) parison tubing is then cut off from both ends in Step 1180, leaving the thin walled, relatively supple balloon and its "legs" to be mounted to the catheter as described below.

This exemplary process can be used to create thin, non-compliant balloons for "angioplasty" of blood vessels at pressures exceeding 12 atmospheres of pressure, for example. Although these pressures are not necessary in the present application, it is witness to the fact that very strong thin-walled balloons can result from the above manufacturing process.

The present invention's thin, non-compliant zero-pressure balloon can be attached to the drainage catheter in a number of ways. In a first exemplary attachment embodiment, reference is made to the process of FIG. 12, the slit valve of FIG. 13, and the removable balloon of FIG. 16.

In an exemplary embodiment, each of the distal and proximal legs of the balloon 1010 manufactured according to the process of FIG. 12 is attached to the distal end of the drainage catheter using standard (e.g., FDA-approved) cements or by heat fusing the two pieces together. The non-compliant, thin-walled balloon is dimensioned to envelop the "slit valves" shown, for example, in FIG. 13, as an exemplary configuration of the invention. The balloon's thin walls allow folding of the balloon without a significant increase in the catheter outer diameter for ease in catheter insertion.

Figure 14:
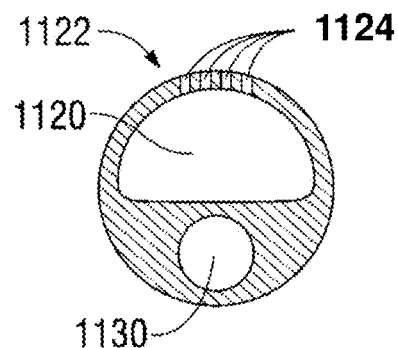
FIG. 14 is a radial cross-sectional view of a slit-valve portion of the catheter of FIG. 13 at section line 14-14.
Figure 15:
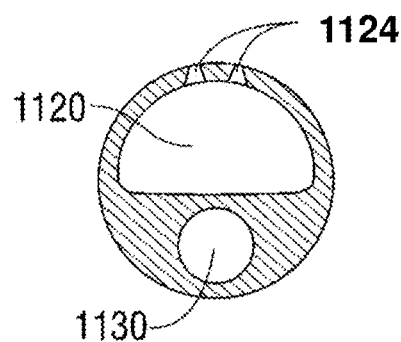
FIG. 15 is a radial cross-sectional view of an alternative embodiment of a slit-valve portion of the catheter of FIG. 13 at section line 15-15.

Exemplary embodiments of the internal balloon valve 1012 according to the invention are illustrated in FIGS. 13, 14, and 15. This internal balloon valve 1012 is formed by cutting the wall of the drainage lumen 1120 at the portion of the catheter shaft 1020 within the balloon 1010. The slit can be a single cut or a plurality of cuts. Some exemplary slit valves other than those shown are described in U.S. Pat. No. 4,995,863 to Nichols et al., all of which can be utilized for the present invention. The slit-opening pressure, therefore, can be regulated by adjusting the number, length and spacing of the slit(s) and the thickness of the drainage lumen wall 1122. For example, the length and orientation of the slit(s) 1012 determines the pressure at which it/they will open and drain the balloon inflation lumen 1130. In one particular embodiment shown in FIG. 15, the slits 1124 are cut through the elastomeric walls in a way that results in a wedge-shaped cross-section. With this wedge shape, fluid within the balloon can drain under pressure easily. The wedge can be increasing or decreasing. With the former, the edges are chamfered towards one another from the central axis of the balloon toward the exterior thereof (e.g., illustrated in FIG. 15) and, with the latter, the edges are chamfered towards one another from the exterior of the balloon toward the central axis.

In another exemplary embodiment, a non-illustrated, thin-walled slitted sleeve can be disposed over the portion of the drainage catheter wall 1122 within the balloon 1010 and covering a throughbore fluidically connecting the interior of the balloon 1010 to the interior of the drainage lumen 1120. As such, pressure within the balloon 1010 will open the slit(s) of the sleeve, thereby fluidically connecting the balloon 1010 interior with the drainage lumen 1120 to transfer fluid in the balloon 1010 to the drainage lumen 1120. Each of these exemplary balloon configurations entirely prevents damage caused by improper inflation or premature removal.

Alternatively, the balloon wall itself could be modified to burst at a particular pressure to release the inflation media. This weakened section could be created by mechanical, chemical, or thermal treatment for example. Mechanical measures may be accomplished by scratching the surface and, thus, thinning the balloon wall in a particular section to cause it to burst at a pre-determined pressure or actually slicing or punching a hole in the wall and covering the area with a thinner, weaker film of material which will tear at a predetermined pressure lower than the rest of the balloon. Likewise, a chemical solvent could be applied to create the same effect as the mechanical device above by making chemical changes to the plastic molecular structure of the balloon wall and, thereby, weakening a desired section of the balloon wall. Weakening a section of the wall by heat to thereby re-orient its molecular structure (much like softening by annealing) is also possible. Therefore, the preferential tearing of the balloon wall at a predetermined internal pressure can be effected in a number of ways as exemplified by, but not limited to, the methods described above.

Figure 16:
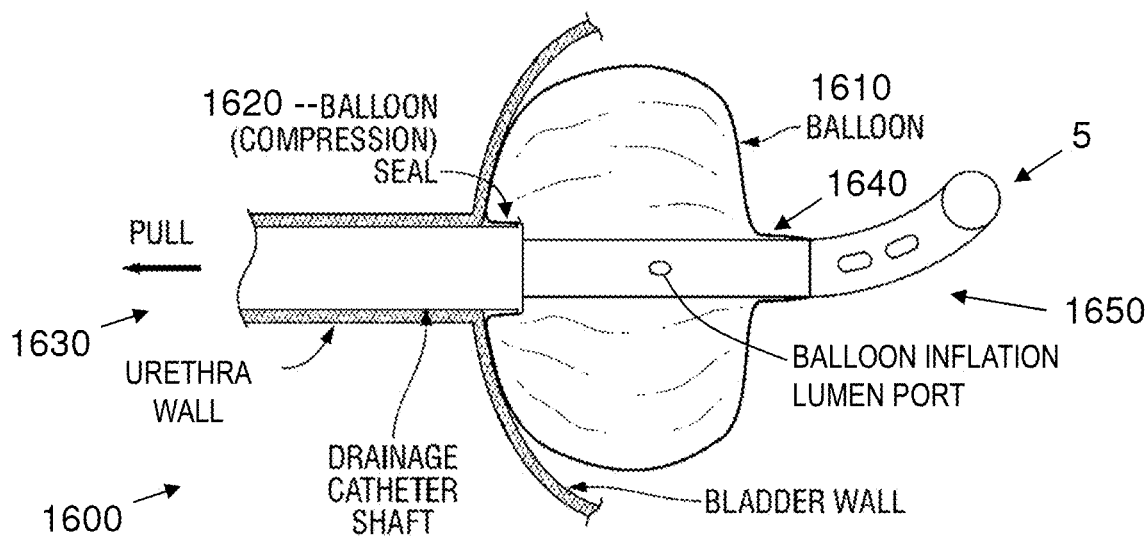
FIG. 16 is a fragmentary, enlarged, partially cross-sectional and partially perspective view of an everting balloon catheter according to the invention in a correctly inserted position in the bladder.

A second exemplary, but not limiting, process to attach the zero-pressure balloon of the present invention to the safety catheter 1600 of the present invention, which can be used with or without the slit valves, is described with respect to FIGS. 12 and 16 and includes, in Step 1210, assembling a first proximal leg 1620 of the balloon 1610 over the distal end of the drainage catheter shaft 1630 in an "inverted" direction (open end toward the balloon interior as shown in FIG. 16). This inverted connection is accomplished with a mechanical release that can be formed, for example, merely by using the shape of the proximal leg 1620 of the balloon 1610 or by using a separate compression device, such as an elastic band, or by using adhesives that removably connect the proximal leg 1620 to the drainage catheter shaft 1630. In a compression only example, the proximal balloon seal is, thereby, formed by the force of the "inverted" relatively non-compliant proximal leg 1620 being extended over and around the distal end of the flexible drainage catheter shaft 1630 by, for example, stretching the material of the drainage catheter shaft 1630 (e.g., silicone) to reduce its outer diameter. The other, distal leg 1640 of the balloon 1610 can, then, be attached in Step 1220 using cements (as in the first example above) or by heat fusion. It is noted that, while attachment is shown and described in an inverted orientation for the proximal leg 1620 and in a non-inverted orientation for the distal leg 1640, these are not the only possible orientations for each and can be assembled in any combination of inverted and non-inverted orientations. For example, the distal leg 1640 can, as the proximal leg 1620, be attached in an inverted direction not illustrated in FIG. 16.

To further aid in balloon assembly and catheter deflation and insertion, the outer diameter of the catheter 1600 under the balloon 1610, as well as the inner diameter of the distal balloon leg 1640, can be reduced as compared with the outer diameter of the drainage catheter shaft 1630, which configuration is shown in FIGS. 16 to 19. The reduced-diameter portion of the catheter 1600 is referred herein as the distal tip portion 1650 and extends from the distal end of the drainage catheter shaft 1630 at least to the distal end of the distal balloon leg 1640. As shown, the distal tip 5 (distal of the balloon 1610) also can have the same reduced diameter (or can be reduced further or increased larger as desired). Thus, if the outer diameter of the distal tip portion 1650 is reduced immediately distal of the proximal balloon seal 1620, any predetermined pull force will stretch the catheter shaft 1630, thereby reducing the outer diameter of the catheter shaft 1630 at the proximal balloon seal and allowing the proximal balloon leg 1620 to slide or peel distally and deflate the balloon quickly, at which time all fluid is released therefrom into the bladder or urethra, for example. It is envisioned that the proximal balloon leg 1620 can be mounted with the balloon leg 1620 in a non-inverted or "straight" position if desired with similar results. However, in such a configuration, sliding of the proximal leg 1620 over the distal end of the catheter shaft 1630 may be more resistant to a pulling force on the exposed proximal end of the catheter shaft 1630 but the slight incursion of the balloon-filling fluid can be used to lubricate this connection and, therefore, the resistance to pulling decreases.

With a zero-pressure configuration as described and referred to herein, the balloon 1010, 1610 is under zero-pressure or low pressure. Thus, the inflation device (e.g., a syringe) need not be configured to deliver pressure much above the low pressure range described above. Mere presence of the filling liquid in the balloon, makes the balloon large enough to resist and prevent movement of the balloon into the urethra and out of the bladder without having an internal, high pressure. As such, when inserted improperly in the urethra, the balloon will simply not inflate because there is no physical space for the balloon to expand and because the inflation pressure remains beneath the urethral damaging pressure threshold. If the inflation device is configured for low pressure, even maximum delivered pressure to the balloon will be insufficient to inflate the balloon within the urethra, thereby preventing any possibility of balloon inflation inside the urethra.

In the other case where the balloon is inflated properly within the bladder but the catheter is improperly removed out from the patient without deflating the balloon, safety devices of the invention prevent tearing of the urethra upon exit. Any combination of the internal balloon valve 1012 (e.g., the slit valve of FIG. 13 formed through the wall of a portion of the drainage lumen 1120 located inside the balloon 1010, 1610) and the removable proximal balloon seal 1620 can be used; one or both can be employed to provide the safety features of the invention. In operation, when a predetermined inflation pressure is reached, the internal balloon valve 1012 opens and any fluid in the balloon 1010, 1610 is emptied through the drainage lumen 1120 into the bladder (distal) and/or the external drain bag (proximal), the latter of which is not illustrated. As set forth above, the point at which pressure causes the internal balloon valve 1012 to open is defined to be less than the pressure needed to damage the urethra when a fully inflated prior-art balloon catheter is improperly removed as described herein. In a low-pressure state, in which the balloon 1010, 1610 is filled with a fluid (either liquid or gas), there is not enough pressure to force open the internal balloon valve 1012 and permit exit of the fluid out from the balloon 1010, 1610. In a higher-pressure state (below urethra damage pressure), in contrast, pressure exerted on the fluid is sufficient to open the internal balloon valve 1012, thus permitting the fluid to quickly drain out of the balloon 1010, 1610 and into the drainage lumen 1120.

In a situation where the balloon 1010, 1610 is in the urethra and inflation is attempted, pressure exerted by the surrounding urethral wall on the inflating balloon 1010, 1610 will cause the internal balloon valve 1012 to open up well before the balloon 1010, 1610 could inflate. Thus, the balloon inflation fluid will, instead of filling the balloon 1010, 1610, exit directly into the drainage lumen 1120. In an alternative embodiment, the fluid used for inflation can be colored to contrast with urine (or any other fluid that is envisioned to pass through the drainage lumen). Thus, if the balloon 1010, 1610 is inserted only into the urethra and inflation is attempted, the inflating fluid will immediately exit into the drainage lumen and enter the exterior (non-illustrated) drain bag. Thus, within a few seconds, the technician will know if the balloon 1010, 1610 did not enter the bladder and inflate therein properly by seeing the colored inflation fluid in the drain bag. In such a situation, the technician needs to only insert the catheter further into the urethra and attempt inflation again. The absence of further colored inflation fluid in the drain bag indicates that correct balloon inflation occurred.

To enhance placement of this catheter in the bladder in the ideal position, in an alternative exemplary embodiment, a visual aid 1030, 1032 for insertion is provided by marking the catheter shaft 1020. This visual aid can be on the exterior surface or it can be embedded within the material comprising the shaft as long as it is visible to medical personnel. For, example, it could be an embedded band of colored plastic or radiopaque material, or it could just be an inked circumferential line. Because male and female patients have urethras of different lengths, a first marker 1030 can be used to indicate an average urethra length 1031 for a male and a second marker 1032 can be used to indicate an average urethra length 1033 for a female.

In this way, if, after believing that insertion is "correct," the user still sees the marking outside the patient, the user can double check the insertion before inflating the balloon (which would occur in the urethra if not installed far enough therein) and entirely prevent injury-causing inflation within the urethra. Additionally, these markings 1030, 1032 can provide immediate indications to medical personnel when it is not known that a patient has jerked out the catheter partially or the catheter snagged on the environment and pulled out partially. In either situation, if the medical personnel looks at the catheter and sees the respective marking 1030, 1032, then it becomes immediately clear that the inflated balloon catheter has been improperly removed, but partially, and immediate corrective action can be taken.

It is noted that this marking feature is only being shown on the catheter of FIG. 9 for illustrative purposes. It is not intended to be limited to the catheter of FIG. 9 and is to be understood as applying to any and/or an of the exemplary embodiments described herein.

In the situation where the balloon 1010, 1610 is inflated within the bladder and the catheter 100 is pulled out from the bladder without deflating the balloon 1010, 1610, pressure exerted by the bladder-urethral junction 11 upon the inflated balloon 1010, 1610 will cause the valve 1012 to open up quickly and cause fluid flow into the drainage lumen 1120 before injury occurs to the junction 11 or the urethra. If, in such a situation, the catheter is also equipped with the removable balloon end (e.g., proximal end 1620), then, as the removable balloon end is peeling off, the slit valve opens up to relieve pressure either before or at the same time the peeling off occurs. This allows the inflation fluid to exit even faster than if just the valve 1012 is present.

Figure 17:
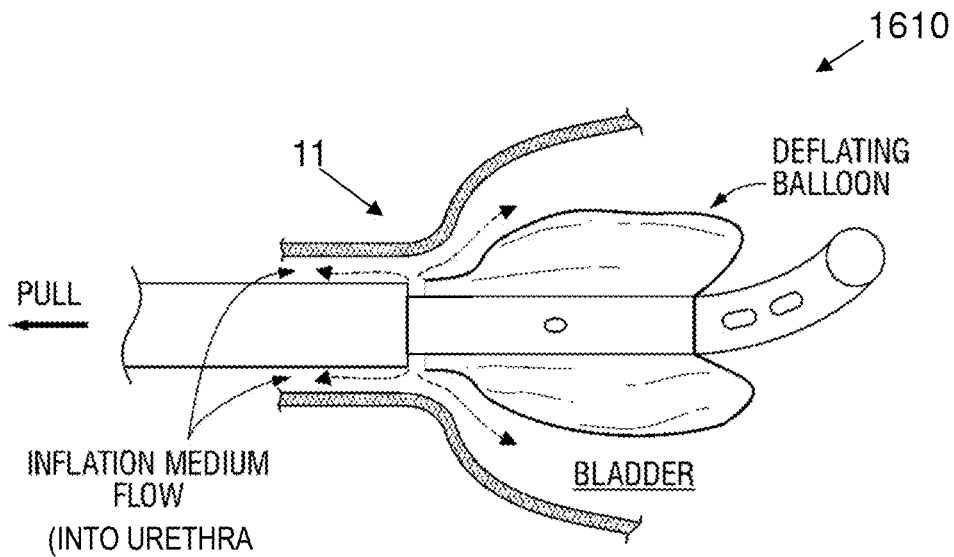
FIG. 17 is a fragmentary, enlarged, partially cross-sectional and partially perspective view of the catheter of FIG. 16 being pulled distally out of the bladder and beginning its everting deflation.
Figure 18:
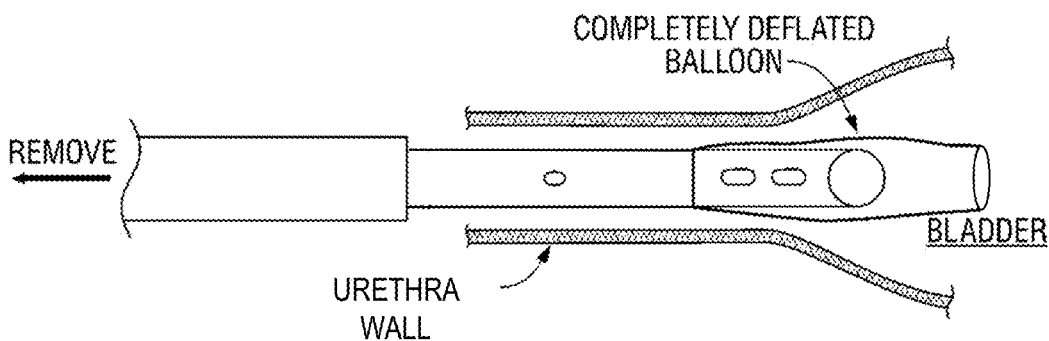
FIG. 18 is a fragmentary, enlarged, partially cross-sectional view of the catheter of FIG. 16 with the everting deflation complete.

FIGS. 16 to 18 illustrate an exemplary embodiment of the inventive catheter 1600 with the everting removable balloon 1610. These figures illustrate the situation where the balloon 1610 is inflated within the bladder and, as indicated by the pull arrow, the catheter 1600 is pulled out from the bladder without deflating the balloon 1610. Here, the distal seal 1640 of the balloon 1610 is fixed to the distal tip portion 1650 of the catheter 1600, which tip 5 has a reduced outer diameter as compared to the drainage catheter shaft 1630, and the proximal seal 1620 is removably attached (e.g., with a compression seal) to the drainage catheter shaft 1630. The pulling force causes the drainage catheter shaft 1630 to move in the proximal direction out of the urethra and, thereby, compress the proximal side of the inflated balloon 1610 against the bladder-urethral junction 11. As the catheter shaft 1630 moves proximally, the force on the proximal seal 1620 increases until the seal 1620 breaks free of the catheter shaft 1630, referred to herein as the breakaway point. FIG. 17 illustrates the now partially inflated balloon 1610 just after the breakaway point. Because the diameter of the distal tip portion 1650 is reduced in comparison to the distal end of the catheter shaft 1630, a gap opens up between the inner diameter of the proximal seal portion of the balloon 1610 and the outer diameter of the distal tip portion 1650. This gap allows the inflating fluid to exit the balloon 1610 quickly into one or both of the urethra and the bladder before injury occurs to the junction 11 or to the urethra. As the central portion of the balloon 1610 is still larger than the urethral opening of the junction 11, the friction and force imparted on the balloon 1610 causes the balloon 1610 to roll over itself, i.e., evert, until it is entirely everted as shown in FIG. 18. At this time, an of the inflating fluid is either in the urethra and/or in the bladder.

In an exemplary embodiment of the removable proximal balloon seal 1620, a pulling force in a range of 1 to 15 pounds will cause the proximal balloon seal 1620 to pull free and allow eversion of the balloon 1610, i.e., the breakaway point. In another exemplary embodiment, the range of force required to meet the breakaway point is between 1 and 5 pounds, in particular, between 1.5 and 2 pounds.

Figure 19:
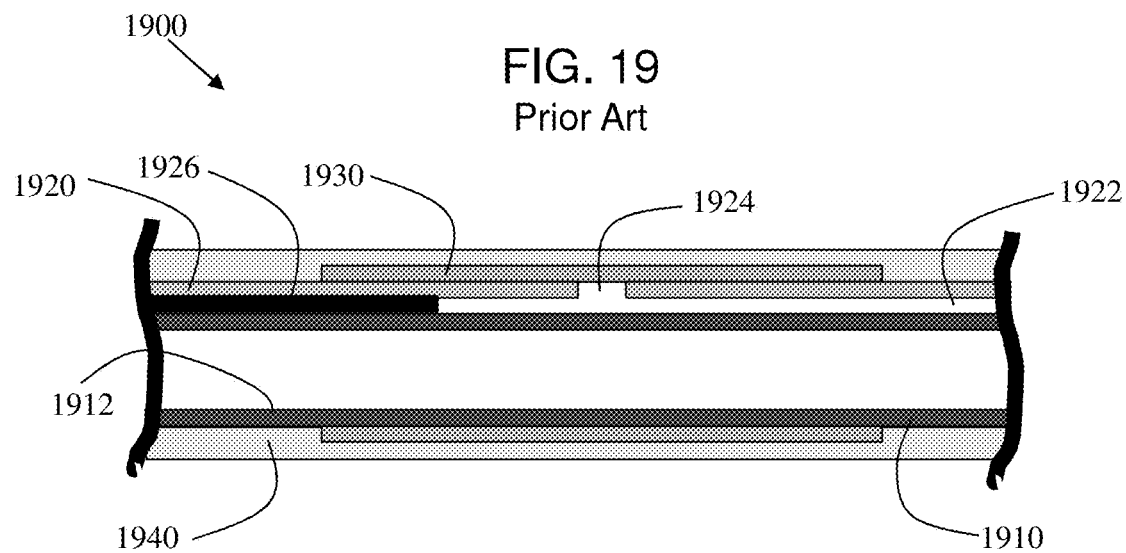
FIG. 19 is a fragmentary, enlarged, longitudinal cross-sectional view of a balloon portion of a prior art urinary catheter in an uninflated state.
Figure 20:
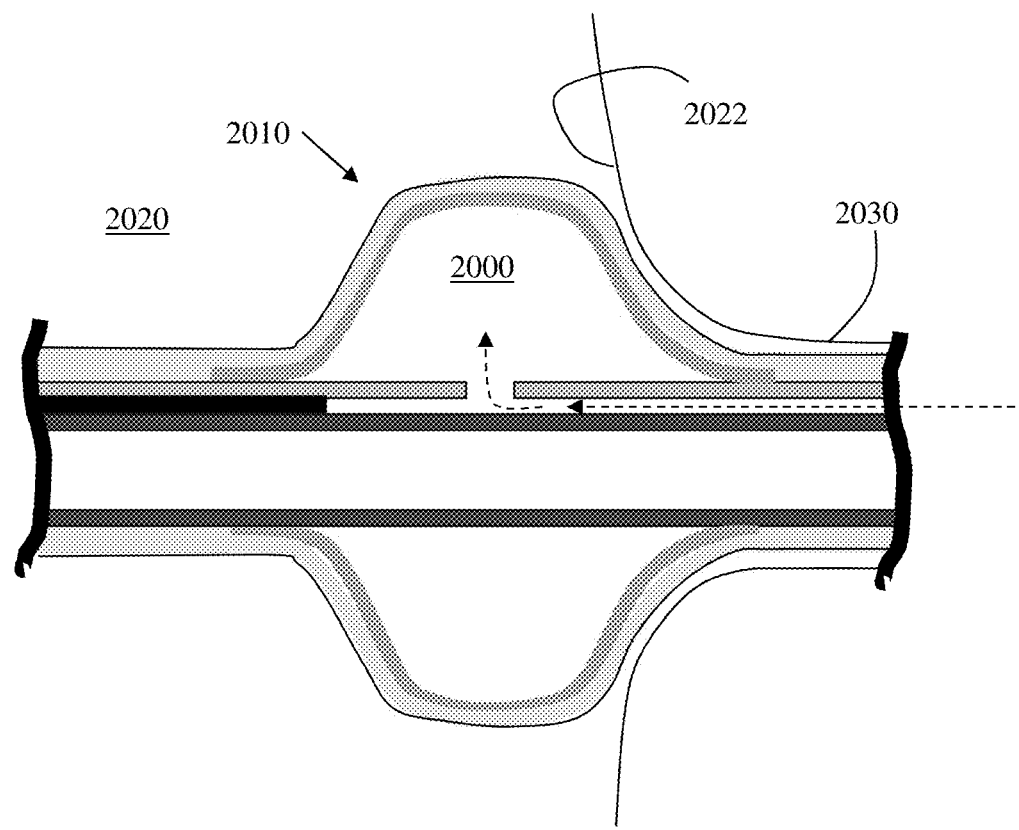
FIG. 20 is a fragmentary, enlarged, longitudinal cross-sectional view of the prior art urinary catheter of FIG. 19 in an inflated state within a bladder.

With regard to additional exemplary embodiments of self-deflating or automatically deflating balloon catheters according to the invention, FIGS. 19 and 20 are provided to illustrate the construction and processes for manufacturing prior art urinary catheters, also referred to as Foley catheters. Although prior art urinary catheters are used herein to assist in the understanding of the exemplary embodiments of urinary balloon catheters according to the invention, neither are used herein to imply that the invention is solely applicable to urinary-type catheters. Instead, the technology described herein can be applied to any balloon catheter, including an mentioned herein.

FIG. 19 shows the balloon portion of the prior art catheter 1900 with the balloon in its uninflated state. An annular inner lumen wall 1910 (red) defines therein a drainage lumen 1912. At one circumferential longitudinal extent about the inner lumen wall 1910, an inflation lumen wall 1920 (orange) defines an inflation lumen 1922 and a balloon inflation port 1924 fluidically connected to the inflation lumen 1922; in standard urinary catheters, there is only one inflation lumen 1922 and one inflation port 1924. The views of FIGS. 19 and 20 show a cross-section through the inflation lumen 1922 and inflation port 1924. If the inflation lumen 1922 extended an of the way through the catheter 1900 to its distal end (to the left of FIGS. 19 and 20), then the balloon could not inflate as an inflation liquid would exit the distal end. Therefore, in order to allow inflation of the balloon, a lumen plug 1926 (black) closes the inflation lumen 1922 distal of the inflation port 1924. In this exemplary illustration, the lumen plug 1926 starts at a position distal of the inflation port 1924 at the inflation lumen 1922.

About the inner lumen and inflation lumen walls 1910, 1920 around the inflation port 1924 is a tube of material that forms the balloon interior wall 1930 (green). The tube forming the balloon interior wall 1930 is fluid-tightly sealed against the respective inner walls 1910, 1920 only at the proximal and distal ends of the tube. Accordingly, a pocket is formed therebetween. An outer wall 1940 (yellow) covers an of the walls 1910, 1920, 1926, 1930 and does so in what has referred to herein as a fluid-tight manner, meaning that any fluid used to blow up the balloon through the inflation lumen 1922 and the inflation port 1924 will not exit the catheter 1900 through the fluid-tight connection. FIG. 20 illustrates the fluid inflating the balloon (indicated with dashed arrows). Because at least the balloon interior wall 1930 and the outer wall 1940 are elastomeric, pressure exerted by the inflating fluid 2000 against these walls will cause them to balloon outwards as, for example, shown in FIG. 20. When the non-illustrated proximal end of the catheter 1900 is sealed with the fluid 2000 therein (e.g., with at least a part of a luer connector as shown in FIG. 3), the catheter 1900 will remain in the shape shown in FIG. 20.

As set forth above, the balloon 2010 of a urinary catheter should be inflated only when in the bladder 2020. FIG. 20 shows the catheter 1900 correctly inflated in the bladder 2020 and then, if needed, pulled proximally so that the inflated balloon 2010 rests against and substantially seals off the urethra 2030 from the interior of the bladder 2020. "Substantially," as used in this regard means that most or an of the urine in the bladder 2020 will drain through the drain lumen 1912 and will not pass around the inflated balloon 2010 more than is typical and/or required for correctly implanted urinary catheters. It is known that an insubstantial amount of urine will pass the balloon 2010 and, advantageously, lubricate the urethra 2030 but will not leak out the end of the urethra as muscles in the various anatomy of males and females will seal the end with sufficient force to prevent significant leakage.

Even though each of the walls is shown in different colors herein, the different colors do not imply that the respective walls must be made of different materials. These colors are used merely for clarity purposes to show the individual parts of the prior art and inventive catheters described herein. As will be described in further detail below, most of the different colored walls actually are, in standard urinary catheters, made of the same material. Some of the biocompatible materials used for standard Foley catheters include latex (natural or synthetic), silicone rubber, and thermoplastic elastomers (TPEs) including styrenic block copolymers, polyolefin blends, elastomeric alloys (TPE-v or TPV), thermoplastic polyurethanes, thermoplastic copolyester, and thermoplastic polyamides.

One exemplary process for creating the prior art urinary catheters starts with a dual lumen extrusion of latex. The dual lumen, therefore, already includes both the drainage lumen 1912 and the inflation lumen 1922. Both lumen 1912, 1922, however, are extruded without obstruction and without radial ports. Therefore, in order to have the inflation port 1924, a radial hole is created from the outside surface inwards to the inflation lumen. Sealing off of the distal end of the inflation lumen 1922 is performed in a subsequent step. The tube making up the inner balloon wall 1930 is slid over the distal end of the multi-lumen extrusion 1910, 1920 to cover the inflation port and is fluid-tightly sealed to the inner multi-lumen extrusion at both ends of the tube but not in the intermediate portion. This tube can be made of latex as well and, therefore, can be secured to the latex multi-lumen extrusion in any known way to bond latex in a fluid-tight manner. At this point, the entire sub-assembly is dipped into latex in its liquid form to create the outer wall 1940. The latex is allowed to enter at least a portion of the distal end of the inflation lumen 1922 but not so far as to block the inflation port 1924. When the latex cures, the balloon 2010 is fluid tight and can only be fluidically connected to the environment through the non-illustrated, proximal-most opening of the inflation port, which is fluidically connected to the inflation lumen 1922. In this process, the inner wall 1910, the inflation lumen wall 1920, the plug 1926, the balloon inner wall 1930, and the outer wall 1940 are all made of the same latex material and, therefore, together form a very secure water-tight balloon 2010.

As set forth above, all prior art balloon catheters are designed to deflate only when actively deflated, either by a syringe similar to the one that inflated it or by surgery after the physician diagnoses the balloon as not being able to deflate, in which circumstance, a procedure to pop the balloon surgically is required.

Described above are various embodiments of self-deflating or automatically deflating catheters according to the invention. FIGS. 21 to 33 illustrate automatically deflating, stretch-valve balloon catheters in still other exemplary embodiments of the present invention. FIGS. 21 to 23 show a first exemplary embodiment of a stretch-valve balloon catheter 2100 according to the invention, FIG. 21 illustrating the balloon portion of the inventive catheter 2100 with the balloon in its uninflated state. An annular inner lumen wall 2110 (red) defines therein a drainage lumen 2112. At one or more circumferential longitudinal extents about the inner lumen wall 2110, an inflation lumen wall 2120 (orange) defines an inflation lumen 2122 and a balloon inflation port 2124 fluidically connected to the inflation lumen 2122; in the inventive catheter, there can be more than one inflation lumen 2122 and corresponding inflation port 2124 even though only one is shown herein. Accordingly, the views of FIGS. 21 to 23 show a cross-section through the single inflation lumen 2122 and single inflation port 2124. A lumen plug 2126 (black) closes the inflation lumen 2122 distal of the inflation port 2124. In this exemplary illustration, the lumen plug 2126 starts at a position distal of the inflation port 2124 at the inflation lumen 2122. This configuration is only exemplary and can start at the inflation port 2124 or anywhere distal thereof.

About the inner lumen and inflation lumen walls 2110, 2120 around the inflation port 2124 is a tube of material that forms the balloon interior wall 2130 (green). The tube of the balloon interior wall 2130 is fluid-tightly sealed against the respective inner walls 2110, 2120 only at the proximal and distal ends of the tube. Accordingly, a pocket is formed therebetween. An outer wall 2140 (yellow) covers all of the walls 2110, 2120, 2126, 2130 in a fluid-tight manner. FIG. 21 illustrates the fluid about to inflate the balloon (indicated with dashed arrows). Because at least the balloon interior wall 2130 and the outer wall 2140 are elastomeric, pressure exerted by the inflating fluid 2200 against these walls will cause them to balloon outwards as, for example, shown in FIG. 22. When the non-illustrated proximal end of the catheter 2100 is sealed with the fluid 2200 therein (e.g., with at least a part of a luer connector as shown in FIG. 3), the catheter 2100 will remain in the shape shown in FIG. 22.

FIG. 22 shows the catheter 2100 correctly inflated in the bladder 2020 and then, if needed, pulled proximally so that the inflated balloon 2210 rests against and substantially seals off the urethra 2030 from the interior of the bladder 2020.

The stretch-valve of the exemplary embodiment of FIGS. 21 to 23 has three different aspects. The first is a hollow, stretch-valve tube 2220 that is disposed in the inflation lumen 2122 to not hinder inflation of the balloon 2210 with the fluid 2200. While the diameter of the stretch-valve tube 2220 can be any size that accommodates substantially unhindered fluid flow through the inflation lumen 2122, one exemplary inner diameter of the stretch-valve tube 2220 is substantially equal to the diameter of the inflation lumen 2122 and the outer diameter of the stretch-valve tube 2220 is just slightly larger than the diameter of the inflation lumen 2122 (e.g., the wall thickness of the tube can be between 0.05 mm and 0.2 mm). The proximal end of the stretch-valve tube 2220 in this exemplary embodiment is proximal of a proximal end of the balloon inner wall 2130. The distal end of the stretch-valve tube 2220 is somewhere near the proximal end of the balloon inner wall 2130; the distal end can be proximal, at, or distal to the proximal end of the balloon inner wall 2130 and selection of this position is dependent upon the amount of stretch S required to actuate the stretch-valve of the inventive catheter 2100 as described below. Another exemplary embodiment of the stretch-valve tube 2220 has one or more of the proximal and distal ends thereof larger in outer diameter than an intermediate portion of the stretch-valve tube 2220. Thus, if one end is larger, the stretch-valve tube 2220 has a "club" shape and, if both ends are larger, the stretch-valve tube 2220 has a "dumbbell" shape. An exemplary configuration of a dumbbell shaped stretch-valve tube is described hereinbelow.

In FIG. 22, the distal end of the stretch-valve tube 2220 is shown at the proximal end of the balloon inner wall 2130. Two ports are formed proximal of the balloon 2210. A proximal port (purple) 2150 is formed through the outer wall 2140 and through the inflation lumen wall 2020 overlapping at least a portion of the proximal end of the stretch-valve tube 2220. In this manner, a portion of the outer surface of the proximal end of the stretch-valve tube 2220 at the proximal port 2150 is exposed to the environment but there is no fluid communication with the inflation lumen 2122 and the proximal port 2150. A distal port (white) 2160 is formed through the outer wall 2140 and through the inflation lumen wall 2020 overlapping at least a portion of the distal end of the stretch-valve tube 2220. In this manner, a portion of the outer surface of the distal end of the stretch-valve tube 2220 at the distal port 2160 is exposed to the environment but there is no fluid communication from the inflation lumen 2122 to the distal port 2160. To secure the stretch-valve tube 2220 in the catheter 2100, the proximal port 2150 is filled with a material that fixes the proximal end of the stretch-valve tube 2220 to at least one of the outer wall 2140 and the inflation lumen wall 2020. In one exemplary embodiment, an adhesive bonds the proximal end of the stretch-valve tube 2220 to both the outer wall 2140 and the inflation lumen wall 2120.

In such a configuration, therefore, any proximal movement of the catheter 2100 at or proximal of the proximal port 2150 will also move the stretch-valve tube 2220 proximally; in other words, the distal end of the stretch-valve tube 2220 can slide S within the inflation lumen 2122 in a proximal direction. FIG. 23 illustrates how the slide-valve of the invention operates when the proximal end of the catheter 2100 is pulled with a force that is no greater than just before injury would occur to the bladder-urethral junction or the urethra if the catheter 2100 was still inflated when the force was imparted. In an exemplary embodiment of the stretch valve of FIGS. 21 to 23, a pulling force in a range of 1 to 15 pounds will cause the stretch-valve tube 2220 to slide proximally S to place the distal end of the stretch-valve tube 2220 just proximal of the distal port 2160, i.e., the deflation point of the stretch-valve shown in FIG. 23. In another exemplary embodiment, the range of force required to meet the deflation point is between 1 and 5 pounds, in particular, between 1.5 and 2 pounds.

As can be seen in FIG. 23, when the deflation point of the stretch-valve is reached, the interior of the balloon 2210 becomes fluidically connected to the distal port 2160. Because the distal port 2160 is open to the environment (e.g., the interior of the bladder 2020) and due to the fact that the bladder is relatively unpressurized as compared to the balloon 2210, all internal pressure is released from the balloon 2210 to eject the inflating fluid 2200 into the bladder 2020 (depicted by dashed arrows), thereby causing the balloon 2210 to deflate rapidly (depicted by solid opposing arrows). It is noted that the distance X (see FIG. 22) between the inflation port 2124 and the distal port 2160 directly impacts the rate at which the balloon 2120 deflates. As such, reducing this distance X will increase the speed at which the balloon 2210 deflates. Also, the cross-sectional areas of the inflation port 2124, the inflation lumen 2122, and the distal port 2160 directly impact the rate at which the balloon 2220 deflates. Further, any changes in direction of the fluid can hinder the rate at which the balloon deflates. One way to speed up deflation can be to shape the distal port 2160 in the form of a non-illustrated funnel outwardly expanding from the inflation lumen 2122. Another way to speed up deflation is to have two or more inflation lumens 2122 about the circumference of the inner lumen wall 2110 and to have corresponding sets of a stretch-valve tube 2220, a proximal port 2150, and a distal port 2160 for each inflation lumen 2122.

Figure 24:
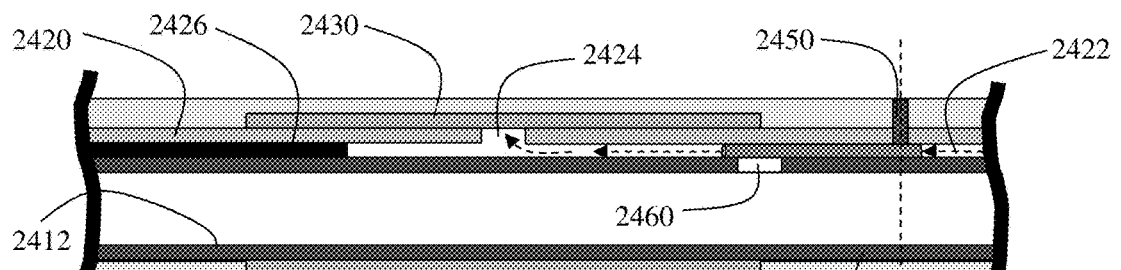
FIG. 24 is a fragmentary, enlarged, longitudinal cross-sectional view of a balloon portion of another exemplary embodiment of an automatically deflating, stretch valve urinary balloon catheter according to the invention with the balloon in an uninflated state.
Figure 25:
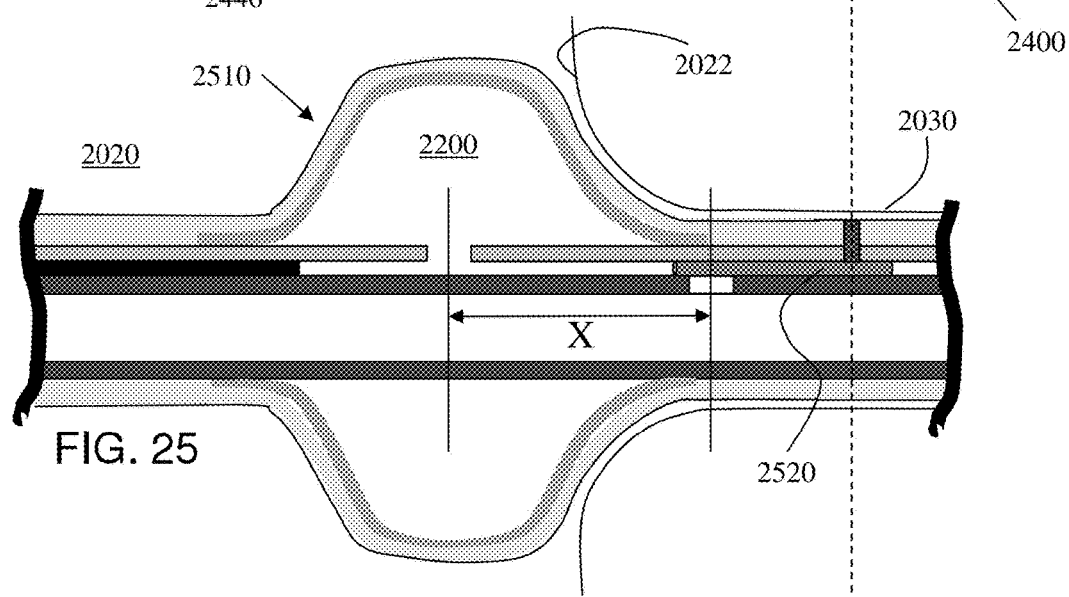
FIG. 25 is a fragmentary, enlarged, longitudinal cross-sectional view of the automatically deflating, stretch valve urinary balloon catheter of FIG. 24 with the balloon in an inflated state and with the stretch valve in an unactuated state.
Figure 26:
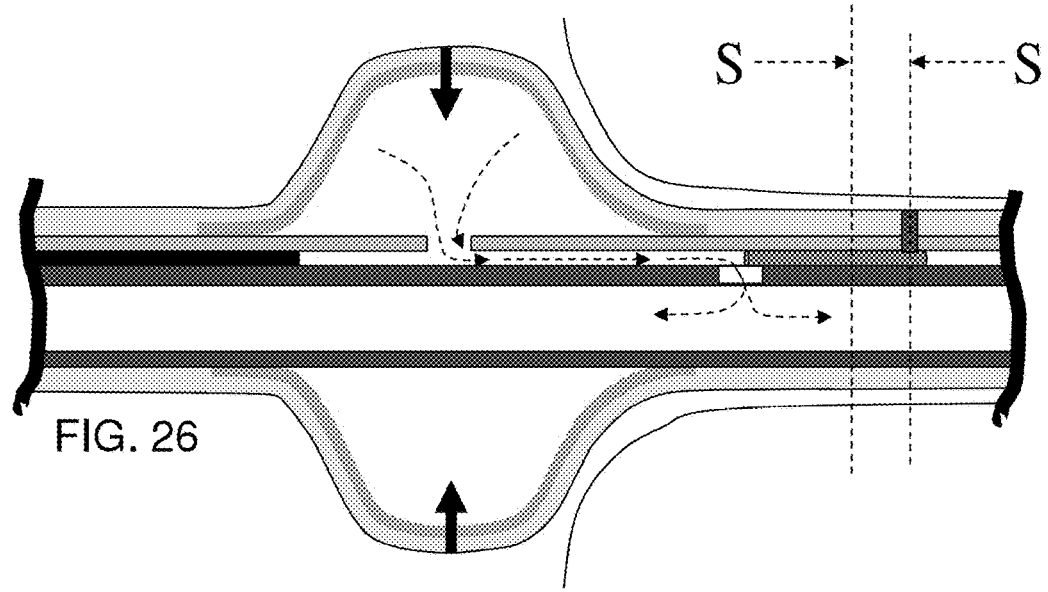
FIG. 26 is a fragmentary, enlarged, longitudinal cross-sectional view of the automatically deflating, stretch valve urinary balloon catheter of FIG. 24 with the balloon in an inflated state and with the stretch valve in an actuated state.

Still another possibility for rapidly deflating an inflated balloon is to drain the fluid 2200 into the drain lumen 2112 instead of the bladder. This exemplary embodiment is illustrated in FIGS. 24 to 26. FIG. 24 illustrates the balloon portion of the inventive catheter 2400 with the balloon in its uninflated state. An annular inner lumen wall 2410 (red) defines therein a drainage lumen 2412. At one or more circumferential longitudinal extents about the inner lumen wall 2410, an inflation lumen wall 2420 (orange) defines an inflation lumen 2422 and a balloon inflation port 2424 fluidically connected to the inflation lumen 2422; in the inventive catheter, there can be more than one inflation lumen 2422 and corresponding inflation port 2424 even though only one is shown herein. Accordingly, the views of FIGS. 24 to 26 show a cross-section through the single inflation lumen 2422 and single inflation port 2424. A lumen plug 2426 (black) closes the inflation lumen 2422 distal of the inflation port 2424. In this exemplary illustration, the lumen plug 2426 starts at a position distal of the inflation port 2424 at the inflation lumen 2422. This configuration is only exemplary and can start at the inflation port 2424 or anywhere distal thereof.

About the inner lumen and inflation lumen walls 2410, 2420 around the inflation port 2424 is a tube of material that forms the balloon interior wall 2430 (green). The tube of the balloon interior wall 2430 is fluid-tightly sealed against the respective inner walls 2410, 2420 only at the proximal and distal ends of the tube. Accordingly, a pocket is formed therebetween. An outer wall 2440 (yellow) covers all of the walls 2410, 2420, 2426, 2430 in a fluid-tight manner. FIG. 24 illustrates the fluid about to inflate the balloon (indicated with dashed arrows). Because at least the balloon interior wall 2430 and the outer wall 2440 are elastomeric, pressure exerted by the inflating fluid 2200 against these walls will cause them to balloon outwards as, for example, shown in FIG. 25. When the non-illustrated proximal end of the catheter 2400 is sealed with the fluid 2200 therein (e.g., with at least a part of a luer connector as shown in FIG. 3), the catheter 2400 will remain in the shape shown in FIG. 25.

FIG. 25 shows the catheter 2400 correctly inflated in the bladder 2020 and then, if needed, pulled proximally so that the inflated balloon 2510 rests against and substantially seals off the urethra 2030 from the interior of the bladder 2020.

The stretch-valve of the exemplary embodiment of FIGS. 24 to 26 has three different aspects. The first is a hollow, stretch-valve tube 2520 that is disposed in the inflation lumen 2422 to not hinder inflation of the balloon 2510 with the fluid 2200. While the diameter of the stretch-valve tube 2520 can be any size that accommodates substantially unhindered fluid flow through the inflation lumen 2422, one exemplary inner diameter of the stretch-valve tube 2520 is substantially equal to the diameter of the inflation lumen 2422 and the outer diameter of the stretch-valve tube 2520 is just slightly larger than the diameter of the inflation lumen 2122 (e.g., the wall thickness of the tube can be between 0.05 mm and 0.2 mm). The proximal end of the stretch-valve tube 2520 in this exemplary embodiment is disposed proximal of a proximal end of the balloon inner wall 2430. The distal end of the stretch-valve tube 2520 is somewhere near the proximal end of the balloon inner wall 2430; the distal end can be proximal, at, or distal to the proximal end of the balloon inner wall 2430 and selection of this position is dependent upon the amount of stretch S required to actuate the stretch-valve of the inventive catheter 2400 as described below. Another exemplary embodiment of the stretch-valve tube 2520 has one or more of the proximal and distal ends thereof larger in outer diameter than an intermediate portion of the stretch-valve tube 2520. Thus, if one end is larger, the stretch-valve tube 2520 has a "club" shape and, if both ends are larger, the stretch-valve tube 2520 has a "dumbbell" shape. An exemplary configuration of a dumbbell shaped stretch-valve tube is described hereinbelow.

In the exemplary embodiment of FIG. 25, the distal end of the stretch-valve tube 2520 is shown at proximal end of the balloon inner wall 2430. Two ports are formed, one proximal of the balloon 2510 and one proximal of the inflation port 2424. A proximal port (purple) 2450 is formed through the outer wall 2440 and through the inflation lumen wall 2420 to overlap at least a portion of the proximal end of the stretch-valve tube 2520. In this manner, a portion of the outer surface of the proximal end of the stretch-valve tube 2520 at the proximal port 2450 is exposed to the environment but there is no fluid communication between the inflation lumen 2422 and the proximal port 2450. A distal port (white) 2460 is formed through the inner lumen wall 2410 anywhere proximal of the inflation port 2424 to overlap a least a portion of the distal end of the stretch-valve tube 2520. In this manner, a portion of the outer surface of the distal end of the stretch-valve tube 2520 at the distal port 2460 is exposed to the drainage lumen 2412 but there is no fluid communication between the inflation lumen 2422 and the distal port 2460. To secure the stretch-valve tube 2520 in the catheter 2400, the proximal port 2450 is filled with a material that fixes the proximal end of the stretch-valve tube 2520 to at least one of the outer wall 2440 and the inflation lumen wall 2420. In one exemplary embodiment, an adhesive bonds the proximal end of the stretch-valve tube 2520 to both the outer wall 2440 and the inflation lumen wall 2420.

In such a configuration, therefore, any proximal movement of the catheter 2400 at or proximal to the proximal port 2450 will also move the stretch-valve tube 2520 proximally; in other words, the distal end of the stretch-valve tube 2520 can slide S within the inflation lumen 2422 in a proximal direction. FIG. 26 illustrates how the slide-valve of the invention operates when the proximal end of the catheter 2400 is pulled to a force that is no greater than just before injury would occur to the bladder-urethral junction or the urethra if the catheter 2400 was still inflated when the force was imparted. In an exemplary embodiment of the stretch valve of FIGS. 24 to 26, a pulling force in a range of 1 to 15 pounds will cause the stretch-valve tube 2520 to slide proximally S to place the distal end of the stretch-valve tube 2520 just proximal of the distal port 2460, i.e., the deflation point of the stretch-valve shown in FIG. 26. In another exemplary embodiment, the range of force required to meet the deflation point is between 1 and 5 pounds, in particular, between 1.5 and 2 pounds.

As can be seen in FIG. 26, when the deflation point of the stretch-valve is reached, the interior of the balloon 2510 becomes fluidically connected to the distal port 2460. Because the distal port 2460 is open to the drainage lumen 2412 (which is open the interior of the bladder 2020 and the non-illustrated, proximal drainage bag) and due to the fact that the bladder is relatively unpressurized as compared to the balloon 2510, all internal pressure is released from the balloon 2510 to eject the inflating fluid 2200 into the drainage lumen 2412 (depicted by dashed arrows in FIG. 26), thereby causing the balloon 2510 to deflate rapidly (depicted by solid opposing arrows in FIG. 26). Again, it is noted that the distance X between the inflation port 2424 and the distal port 2460 (see FIG. 25) directly impacts the rate at which the balloon 2510 deflates. As such, having this distance X be smaller will increase the speed at which the balloon 2510 deflates. Also, the cross-sectional areas of the inflation port 2424, the inflation lumen 2422, and the distal port 2460 directly impact the rate at which the balloon 2120 deflates. Further, any changes in direction of the fluid can hinder the rate at which the balloon deflates. One way to speed up deflation can be to shape the distal port 2460 in the form of a funnel outwardly expanding from the inflation lumen 2422. Another way to speed up deflation can be to have two or more inflation lumens 2422 about the circumference of the inner lumen wall 2410 and to have corresponding sets of a stretch-valve tube 2520, a proximal port 2450, and a distal port 2460 for each inflation lumen 2422.

Yet another exemplary embodiment that is not illustrated herein is to combine both of the embodiments of FIGS. 21 to 23 and 24 to 26 to have the fluid 2200 drain out from both of the distal ports 2160, 2460 into both the bladder 2020 and the drain lumen 2112, respectively.

Still another possibility for rapidly deflating an inflated balloon is to drain the fluid 2200 directly into the drain lumen 2712 in a straight line without any longitudinal travel X. This exemplary embodiment is illustrated in FIGS. 27 to 29. FIG. 27 illustrates the balloon portion of the inventive catheter 2700 with the balloon in its uninflated state. An annular inner lumen wall 2710 (red) defines therein a drainage lumen 2712. At one or more circumferential longitudinal extents about the inner lumen wall 2710, an inflation lumen wall 2720 (orange) defines an inflation lumen 2722 and a balloon inflation port 2724 fluidically connected to the inflation lumen 2722; in the inventive catheter, there can be more than one inflation lumen 2722 and corresponding inflation port 2724 even though only one is shown herein. Accordingly, the views of FIGS. 27 to 29 show a cross-section through the single inflation lumen 2722 and single inflation port 2724. A lumen plug 2726 (black) closes the inflation lumen 2722 distal of the inflation port 2724. In this exemplary illustration, the lumen plug 2726 starts at a position distal of the inflation port 2724 at the inflation lumen 2722. This configuration is only exemplary and can start at the inflation port 2724 or anywhere distal thereof.

About the inner lumen and inflation lumen walls 2710, 2720 around the inflation port 2724 is a tube of material that forms the balloon interior wall 2730 (green). The tube of the balloon interior wall 2730 is fluid-tightly sealed against the respective inner walls 2710, 2720 only at the proximal and distal ends of the tube. Accordingly, a pocket is formed therebetween. An outer wall 2740 (yellow) covers all of the walls 2710, 2720, 2726, 2730 in a fluid-tight manner. FIG. 27 illustrates the fluid about to inflate the balloon (indicated with dashed arrows). Because at least the balloon interior wall 2730 and the outer wall 2740 are elastomeric, pressure exerted by the inflating fluid 2200 against these walls will cause them to balloon outwards as, for example, shown in FIG. 28. When the non-illustrated proximal end of the catheter 2700 is sealed with the fluid 2200 therein (e.g., with at least a part of a luer connector as shown in FIG. 3), the catheter 2700 will remain in the shape shown in FIG. 28.

FIG. 28 shows the catheter 2700 correctly inflated in the bladder 2020 and then, if needed, pulled proximally so that the inflated balloon 2810 rests against and substantially seals off the urethra 2030 from the interior of the bladder 2020.

The stretch-valve of the exemplary embodiment of FIGS. 27 to 29 has three different aspects. The first is a hollow, stretch-valve tube 2820 that is disposed in the inflation lumen 2722 to not hinder inflation of the balloon 2810 with the fluid 2200. While the diameter of the stretch-valve tube 2820 can be any size that accommodates substantially unhindered fluid flow through the inflation lumen 2722, one exemplary inner diameter of the stretch-valve tube 2820 is substantially equal to the diameter of the inflation lumen 2722 and the outer diameter of the stretch-valve tube 2820 is just slightly larger than the diameter of the inflation lumen 2722 (e.g., the wall thickness of the tube can be between 0.05 mm and 0.2 mm). The proximal end of the stretch-valve tube 2820 in this exemplary embodiment is proximal of a proximal end of the balloon inner wall 2730. The distal end of the stretch-valve tube 2820 is somewhere near the proximal end of the balloon inner wall 2730; the distal end can be proximal, at, or distal to the proximal end of the balloon inner wall 2730 and selection of this position is dependent upon the amount of stretch S required to actuate the stretch-valve of the inventive catheter 2700 as described below. Another exemplary embodiment of the stretch-valve tube 2820 has one or more of the proximal and distal ends thereof larger in outer diameter than an intermediate portion of the stretch-valve tube 2820. Thus, if one end is larger, the stretch-valve tube 2820 has a "club" shape and, if both ends are larger, the stretch-valve tube 2820 has a "dumbbell" shape. An exemplary configuration of a dumbbell shaped stretch-valve tube is described hereinbelow.

In the exemplary embodiment of FIG. 28, the distal end of the stretch-valve tube 2820 is shown between the inflation port 2724 and the proximal end of the balloon inner wall 2730. Two ports are formed, one proximal of the balloon 2810 and one between the inflation port 2724 and the proximal end of the balloon inner wall 2730. A proximal port 2750 is formed through the outer wall 2740 through the inflation lumen wall 2720 to overlap at least a portion of the proximal end of the stretch-valve tube 2820. In this manner, a portion of the outer surface of the proximal end of the stretch-valve tube 2820 at the proximal port 2750 is exposed to the environment but there is no fluid communication between the inflation lumen 2722 and the proximal port 2750. A distal port (white) 2760 is formed through both inflation lumen wall 2720 and the inner wall 2710 distal of the proximal connection of the balloon inner wall 2730 to overlap a least a portion of the distal end of the stretch-valve tube 2820. In this manner, opposing portions of the outer surface of the distal end of the stretch-valve tube 2820 at the distal port 2760 are exposed, one exposed to the interior of the balloon 2810 and one exposed to the drainage lumen 2712 but there is no fluid communication between either the inflation lumen 2722 or the drainage lumen 2712 and the distal port 2760. To secure the stretch-valve tube 2820 in the catheter 2700, the proximal port 2750 is filled with a material that fixes the proximal end of the stretch-valve tube 2820 to at least one of the outer wall 2740 and the inflation lumen wall 2720. In one exemplary embodiment, an adhesive bonds the proximal end of the stretch-valve tube 2820 to both the outer wall 2740 and the inflation lumen wall 2720. In the exemplary embodiment, the adhesive can be the same material as any or all of the walls 2710, 2720, 2730, 2740 or it can be a different material. If the outer wall 2740 is formed by a dipping of the interior parts into a liquid bath of the same material as, for example, a dual lumen extrusion including the inner wall 2710 and the inflation lumen wall 2720, then, when set, the outer wall 2740 will be integral to both the inner wall 2710 and the inflation lumen wall 2720 and will be fixedly connected to the stretch-valve tube 2820 through the proximal port 2750.

In such a configuration, therefore, any proximal movement of the catheter 2700 at or proximal to the proximal port 2750 will also move the stretch-valve tube 2820 proximally; in other words, the distal end of the stretch-valve tube 2820 can slide S within the inflation lumen 2722 in a proximal direction. FIG. 29 illustrates how the slide-valve of the invention operates when the proximal end of the catheter 2700 is pulled to a force that is no greater than just before injury would occur to the bladder-urethral junction or the urethra if the catheter 2700 was still inflated when the force was imparted. In an exemplary embodiment of the stretch valve of FIGS. 27 to 29, a pulling force in a range of 1 to 15 pounds will cause the stretch-valve tube 2820 to slide proximally S to place the distal end of the stretch-valve tube 2820 just proximal of the distal port 2760, i.e., the deflation point of the stretch-valve shown in FIG. 29. In another exemplary embodiment, the range of force required to meet the deflation point is between 1 and 5 pounds, in particular, between 1.5 and 2 pounds.

As can be seen in FIG. 29, when the deflation point of the stretch-valve is reached, the interior of the balloon 2810 becomes fluidically connected to both the upper and lower portions of the distal port 2760 in a direct and straight line. Because the distal port 2760 is open to the drainage lumen 2712 (which is open the interior of the bladder 2020 and to the non-illustrated, proximal drain bag) and due to the fact that the bladder is relatively unpressurized as compared to the balloon 2810, an internal pressure is released from the balloon 2810 to eject the inflating fluid 2200 into the drainage lumen 2712 (depicted by dashed arrows in FIG. 29), thereby causing the balloon 2810 to deflate rapidly (depicted by solid opposing arrows). Unlike the embodiments above, the distance X between the deflation port (the upper part of distal port 2760) and the lower part of distal port 2760 is zero—therefore, the rate at which the balloon 2510 deflates cannot be made any faster (other than expanding the area of the distal port 2760). It is further noted that the inflation port 2724 also becomes fluidically connected to the drain lumen 2712 and, therefore, drainage of the fluid 2200 occurs through the inflation port 2724 as well (also depicted by a dashed arrow). The cross-sectional area of the inflation lumen 2722 only slightly impacts the rate of balloon deflation, if at all. One way to speed up deflation can be to shape the distal port 2760 in the form of a funnel outwardly expanding in a direction from the outer circumference of the catheter 2700 inwards towards the drainage lumen 2712. Another way to speed up deflation can be to have two or more inflation lumens 2722 about the circumference of the inner lumen wall 2710 and to have corresponding sets of a stretch-valve tube 2820, a proximal port 2750, and a distal port 2760 for each inflation lumen 2722.

Figure 30:
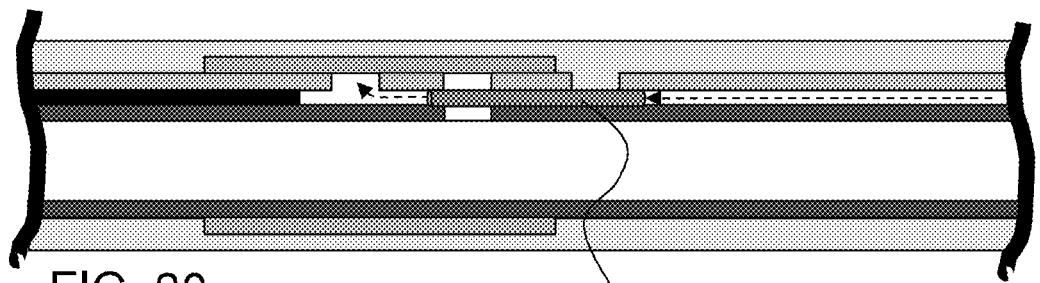
FIG. 30 is a fragmentary, enlarged, longitudinal cross-sectional view of the automatically deflating, stretch valve urinary balloon catheter of FIG. 27.
Figure 31:
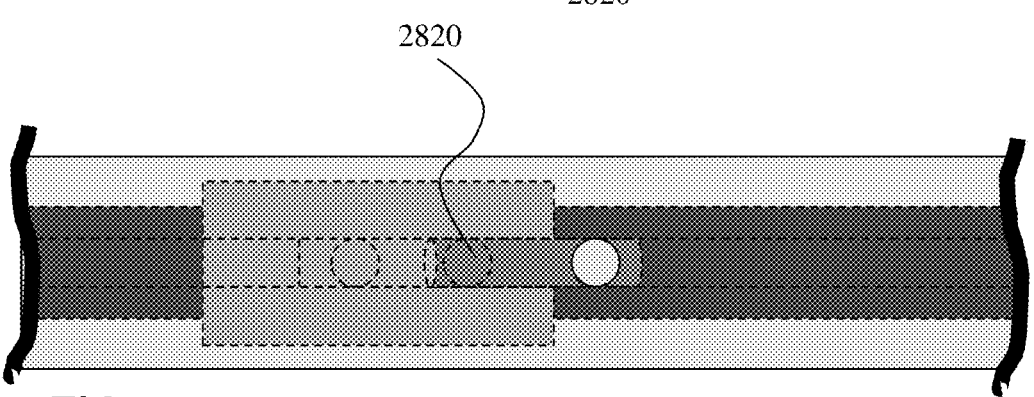
FIG. 31 is a fragmentary, enlarged, longitudinal cross-sectional view of the automatically deflating, stretch valve urinary balloon catheter of FIG. 27 turned ninety degrees counterclockwise when viewed from a proximal end thereof and with the stretch valve in an unactuated state.
Figure 32:
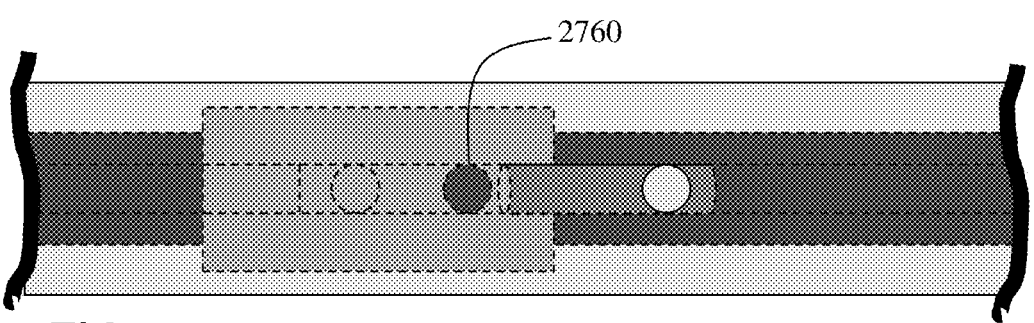
FIG. 32 is a fragmentary, enlarged, longitudinal cross-sectional view of the automatically deflating, stretch valve urinary balloon catheter of FIG. 27 turned ninety degrees counterclockwise when viewed from a proximal end thereof and with the stretch valve in an actuated state.

FIG. 30 reproduces FIG. 27 to assist in explaining FIGS. 31 and 32 on the same page. FIGS. 31 and 32 show, respectively, the closed and opened positions of the stretch-valve tube 2820 in FIGS. 28 and 29. These figures are viewed in an orientation turned ninety degrees counterclockwise with regard to a central, longitudinal axis of the catheter 2700 viewed along the axis towards the distal end from the proximal end so that the view looks down upon the distal port 2760. As can be seen, without pulling on the proximal end of the catheter 2700 (FIG. 31), the stretch-valve tube 2820 blocks the distal port 2760. With a proximal force on the proximal end of the catheter 2700, as shown in the orientation of FIG. 32, the stretch-valve tube 2820 slides and no longer blocks the distal port 2760.

FIGS. 33 to 36 show alternative exemplary embodiments for the automatically deflating, stretch-valve, safety balloon catheter according to the invention. Where various parts of the embodiments are not described with regard to these figures (e.g., the balloon interior wall), the above-mentioned parts are incorporated by reference herein into these embodiments and are not repeated for reasons of brevity.

Figure 33:
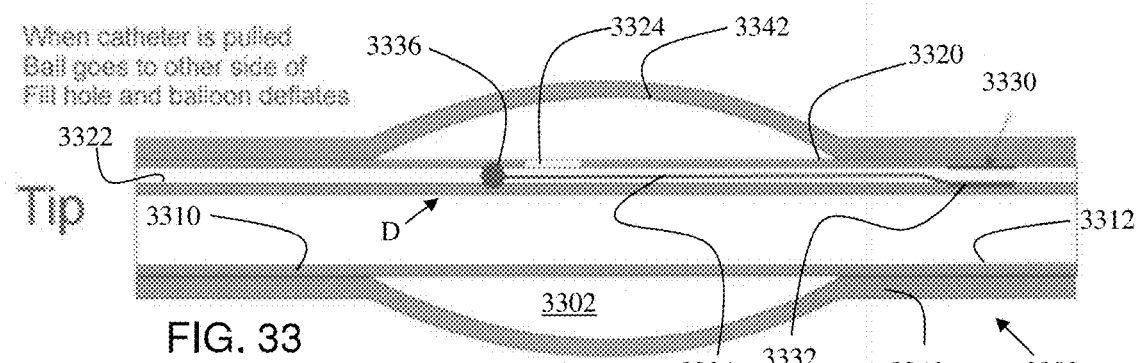
FIG. 33 is a fragmentary, enlarged, longitudinal cross-sectional view of a balloon portion of yet another exemplary embodiment of an automatically deflating, stretch valve urinary balloon catheter according to the invention with the balloon in a partially inflated state and the stretch valve in an unactuated state.

FIG. 33 illustrates the balloon portion of the inventive catheter 3300 with the balloon 3302 in a partially inflated state. An annular inner lumen wall 3310 defines therein a drainage lumen 3312. At one or more circumferential longitudinal extents about the inner wall 3310, an inflation lumen wall 3320 defines an inflation lumen 3322 and a balloon inflation port 3324 fluidically connected to the inflation lumen 3322; in the inventive catheter, there can be more than one inflation lumen 3322 and corresponding inflation port 3324 even though only one is shown herein. Accordingly, the views of FIGS. 33 to 36 show a cross-section through the single inflation lumen and single inflation port. No lumen plug closes the inflation lumen 3322 distal of the inflation port 3324 (this is in contrast to the above-described exemplary embodiments). In the exemplary embodiment of FIG. 33, a stretch-valve mechanism 3330 serves to plug the inflation lumen 3322 distal of the inflation port 3324 as described in further detail below. An outer wall 3340 covers all of the interior walls 3310 and 3320 in a fluid-tight manner and forms the exterior of the balloon 3342 but does not cover the distal end of the inflation lumen 3322. The outer wall 3340 is formed in any way described herein and is not discussed in further detail here.

The stretch-valve mechanism 3330 is disposed in the inflation lumen 3322 to not hinder inflation of the balloon 3302 with inflating fluid. A proximal, hollow anchor portion 3332 is disposed in the inflation lumen 3320 proximal of the inflation port 3324. While the diameter of the hollow anchor portion 3332 can be any size that accommodates substantially unhindered fluid flow through the inflation lumen 3322, one exemplary inner diameter of the hollow anchor portion 3332 is substantially equal to the diameter of the inflation lumen 3322 and the outer diameter of the hollow anchor portion 3332 is just slightly larger than the diameter of the inflation lumen 3322 (e.g., the wall thickness of the tube can be between 0.05 mm and 0.2 mm). The longitudinal length of the hollow anchor portion 3332 is as long as desired to be longitudinally fixedly secured within the inflation lumen 3322 when installed in place. The tube, from its shape alone, can provide the securing connection but, also, an adhesive can be used in any manner, one of which includes creating a proximal port as shown in the above embodiments and utilizing the dipped exterior to form the fixed connection. The distal end of the hollow anchor portion 3332 in this exemplary embodiment is proximal of a proximal end of the balloon 3302. The distal end of the hollow anchor portion 3332 can be nearer to the inflation port 3324, but not at or distal of the inflation port 3324; both ends of the hollow anchor portion 3332 can be proximal, at, or distal to the proximal end of the balloon 3302 and selection of this position is dependent upon the amount of stretch that is desired to actuate the stretch-valve of the inventive catheter 3300 as described below. In the exemplary embodiment of FIG. 33, the stretch-valve mechanism 3330 also includes an intermediate stopper wire 3334 connected at its proximal end to the hollow anchor portion 3332 and a stopper 3336 connected to the distal end of the stopper wire 3334. The stopper 3336 is sized to be slidably disposed in the inflation lumen 3322 while, at the same time, to provide a fluid-tight seal so that liquid cannot pass from one side of the stopper 3336 to the other side within the inflation lumen 3322. The stopper 3336 is located distal of the inflation port 3324. The stopper wire 3334, therefore, spans the inflation port 3324. Because the stopper 3336 must traverse the inflation port 3324, it must be just distal of the inflation port 3324, but the hollow anchor portion can be located anywhere proximal of the inflation port 3324. While the length of the stopper wire 3334 needs to be sufficient to span the inflation port 3324, it can be as long as desired, which will depend on where the hollow anchor portion 3332 resides as well as the amount of stretch desired. As the catheter 3300 stretches more at its proximal end and less at its distal end when pulled from the proximal end, the hollow anchor portion 3322 can be further proximal in the inflation lumen 3322 than shown, and can even be very close to or at the proximal end of the inflation lumen 3322. Even though the term "wire" is used herein, this does not necessarily mean that the wire structure is an incompressible rod. It can, likewise, be a flexible but non-stretchable cable or cord. In such a configuration, therefore, once the stopper 3336 is pulled proximally (to the right in FIG. 33), it will not be forced back distally once the stretching of the catheter is released. As such, the flexible cable embodiment provides a single-actuation valve.

In such a configuration, therefore, any proximal movement of the catheter 3300 at or proximal to the inflation port 3324 will also move the stretch-valve mechanism 3330 proximally; in other words, the stopper 3336 slides proximally within the inflation lumen 3322 from distal of the inflation port 3324 to a proximal side of the inflation port 3324. When the proximal end of the catheter 3300 is pulled to move the stopper 3336 across the inflation port 3324 with a force that is no greater than just before injury would occur to the bladder-urethral junction or the urethra if the catheter 3300 was still inflated when the force was imparted, fluid in the balloon 3342 can exit distally out the inflation lumen 3322. In an exemplary embodiment of the stretch valve of FIG. 33, a pulling force in a range of 1 to 15 pounds will cause the stretch-valve mechanism 3330 to slide proximally to place the stopper 3336 just proximal of the inflation port 3324, i.e., the deflation point of the stretch-valve shown in FIG. 33. In another exemplary embodiment, the range of force required to meet the deflation point is between 1 and 5 pounds, in particular, between 1.5 and 2 pounds. When the stopper 3336 traverses the inflation port 3324, the balloon 3342 automatically deflates and the inflating fluid exits into the bladder out the distal end of the inflation lumen 3332, which is open at the distal end of the catheter 3300.

Figure 34:
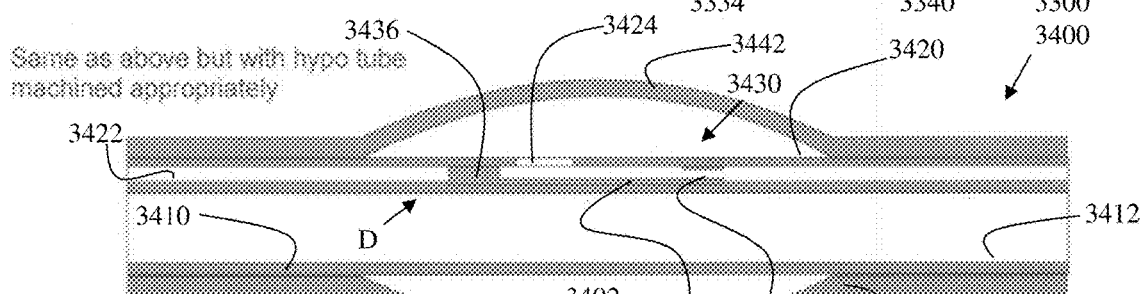
FIG. 34 is a fragmentary, enlarged, longitudinal cross-sectional view of a balloon portion of yet a further exemplary embodiment of an automatically deflating, stretch valve urinary balloon catheter according to the invention with the balloon in a partially inflated state and the stretch valve in an unactuated state

FIG. 34 illustrates the balloon portion of the inventive catheter 3400 with the balloon 3402 in a partially inflated state. An annular inner lumen wall 3410 defines therein a drainage lumen 3412. At one or more circumferential longitudinal extents about the inner lumen wall 3410, an inflation lumen wall 3420 defines an inflation lumen 3422 and a balloon inflation port 3424 fluidically connected to the inflation lumen 3422; in the inventive catheter, there can be more than one inflation lumen 3422 and corresponding inflation port 3424 even though only one is shown herein. No lumen plug closes the inflation lumen 3422 distal of the inflation port 3424. In this exemplary embodiment, a stretch-valve mechanism 3430 serves to plug the inflation lumen 3422 distal of the inflation port 3424 as described in further detail below. An outer wall 3440 covers all of the interior walls 3410 and 3420 in a fluid-tight manner and forms the exterior of the balloon 3442 but does not cover the distal end of the inflation lumen 3422. The outer wall 3440 is formed in any way described herein and is not discussed in further detail here.

The stretch-valve mechanism 3430 is disposed in the inflation lumen 3422 and does not hinder inflation of the balloon 3402 with inflating fluid. A proximal, hollow anchor portion 3432 is disposed in the inflation lumen 3420 proximal of the inflation port 3424. While the diameter of the hollow anchor portion 3432 can be any size that accommodates substantially unhindered fluid flow through the inflation lumen 3422, one exemplary inner diameter of the hollow anchor portion 3432 is substantially equal to the diameter of the inflation lumen 3422 and the outer diameter of the hollow anchor portion 3432 is just slightly larger than the diameter of the inflation lumen 3422 (e.g., the wall thickness of the tube can be between 0.05 mm and 0.2 mm). Another exemplary embodiment of the hollow anchor portion 3432 and a stopper 3436 has one or more of these larger in outer diameter than an intermediate hollow stopper tube 3434. Thus, if one end is larger, the stretch-valve mechanism 3430 has a "club" shape and, if both ends are larger, the stretch-valve mechanism 3430 has a "dumbbell" shape. An exemplary configuration of a dumbbell shaped stretch-valve tube is described hereinbelow.

The longitudinal length of the hollow anchor portion 3432 is as long as desired to be longitudinally fixedly secured within the inflation lumen 3422 when installed in place. The tube, from its shape alone, can provide the securing connection but, also, an adhesive can be used in any manner, one of which includes creating a proximal port as shown in the above embodiments and utilizing the dipped exterior to form the fixed connection. The distal end of the hollow anchor portion 3432 in this exemplary embodiment is at a proximal side of the balloon 3402. The distal end of the hollow anchor portion 3432 can be nearer to the inflation port 3424, but not at or distal of the inflation port 3424; both ends of the hollow anchor portion 3432 can be proximal, at, or distal to the proximal end of the balloon 3402 and selection of this position is dependent upon the amount of stretch that is desired to actuate the stretch-valve of the inventive catheter 3400 as described below. In the exemplary embodiment of FIG. 34, the intermediate hollow stopper tube 3434 is connected at its proximal end to the hollow anchor portion 3432 and the stopper 3436 is connected to the distal end of the stopper tube 3434. The stopper tube 3434 is only a circumferential portion of the hollow anchor portion 3432 and is located opposite the inflation port 3424 so that it does not obstruct fluid flow through the inflation port 3424. The stopper 3436, in contrast, is a solid cylinder having the same or different outer diameter as the hollow anchor portion 3432. The entire mechanism 3430 is sized to be slidably disposed in the inflation lumen 3422 while, at the same time, to provide a fluid-tight seal at the stopper 3436 so that liquid cannot pass from one side of the stopper 3436 to the other side within the inflation lumen 3422. The stopper 3436 is located distal of the inflation port 3424. The stopper tube 3434, therefore, spans the inflation port 3424. Because the stopper 3436 must traverse the inflation port 3424, it must be just distal of the inflation port 3424 but the hollow anchor portion 3432 can be located anywhere proximal of the inflation port 3424. While the length of the stopper tube 3434 needs to be sufficient to span the inflation port 3424, it can be as long as desired, which will depend on where the hollow anchor portion 3432 resides. As the catheter 3400 stretches more at its proximal end and less at its distal end when pulled from the proximal end, the hollow anchor portion 3422 can be further proximal in the inflation lumen 3422 than shown, and can even be very close to or at the proximal end of the inflation lumen 3422.

In such a configuration, therefore, any proximal movement of the catheter 3400 at or proximal to the inflation port 3424 will also move the stretch-valve mechanism 3430 proximally; in other words, the stopper 3436 slides proximally within the inflation lumen 3422 from distal of the inflation port 3424 to a proximal side of the inflation port 3424. When the proximal end of the catheter 3400 is pulled to move the stopper 3436 across the inflation port 3424 with a force that is no greater than just before injury would occur to the bladder-urethral junction or the urethra if the catheter 3400 was still inflated when the force was imparted, fluid in the balloon 3442 can exit distally out the inflation lumen 3422. In an exemplary embodiment of the stretch valve of FIG. 34, a pulling force in a range of 1 to 15 pounds will cause the stretch-valve mechanism 3430 to slide proximally to place the stopper 3436 just proximal of the inflation port 3424, i.e., the deflation point of the stretch-valve shown in FIG. 34. In another exemplary embodiment, the range of force required to meet the deflation point is between 1 and 5 pounds, in particular, between 1.5 and 2 pounds. When the stopper 3436 traverses the inflation port 3424, the balloon 3442 automatically deflates and the inflating fluid exits into the bladder out the distal end of the inflation lumen 3432, which is open at the distal end of the catheter 3400.

Figure 35:
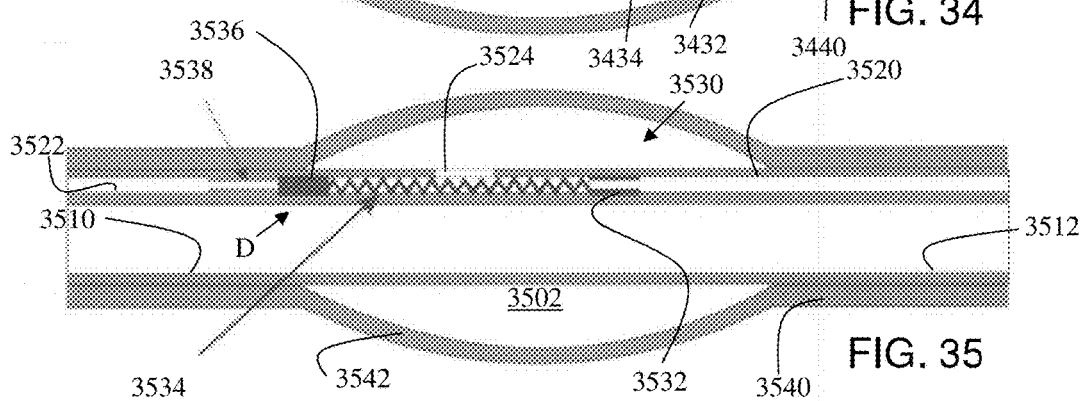
FIG. 35 is a fragmentary, enlarged, longitudinal cross-sectional view of a balloon portion of still a further exemplary embodiment of an automatically deflating, stretch valve urinary balloon catheter according to the invention with the balloon in a partially inflated state and the stretch valve in an unactuated state.

FIG. 35 illustrates the balloon portion of the inventive catheter 3500 with the balloon 3502 in a partially inflated state. An annular inner lumen wall 3510 defines therein a drainage lumen 3512. At one or more circumferential longitudinal extents about the inner lumen wall 3510, an inflation lumen wall 3520 defines an inflation lumen 3522 and a balloon inflation port 3524 fluidically connected to the inflation lumen 3522; in the inventive catheter, there can be more than one inflation lumen 3522 and corresponding inflation port 3524 even though only one is shown herein. No lumen plug closes the inflation lumen 3522 distal of the inflation port 3524. In this exemplary embodiment, a stretch-valve mechanism 3530 serves to plug the inflation lumen 3522 distal of the inflation port 3524 as described in further detail below. An outer wall 3540 covers all of the interior walls 3510 and 3520 in a fluid-tight manner and forms the exterior of the balloon 3542 but does not cover the distal end of the inflation lumen 3522. The outer wall 3540 is formed in any way described herein and is not discussed in further detail here.

The stretch-valve mechanism 3530 is disposed in the inflation lumen 3522 to not hinder inflation of the balloon 3502 with inflating fluid. A proximal, hollow anchor portion 3532 is disposed in the inflation lumen 3520 proximal of the inflation port 3524. While the diameter of the hollow anchor portion 3532 can be any size that accommodates substantially unhindered fluid flow through the inflation lumen 3522, one exemplary inner diameter of the hollow anchor portion 3532 is substantially equal to the diameter of the inflation lumen 3522 and the outer diameter of the hollow anchor portion 3532 is just slightly larger than the diameter of the inflation lumen 3522 (e.g., the wall thickness of the tube can be between 0.05 mm and 0.2 mm). Another exemplary embodiment of the hollow anchor portion 3532 and a stopper 3536 has one or more of these larger in outer diameter than an intermediate bias device 3534. Thus, if one end is larger, the stretch-valve mechanism 3430 has a "club" shape and, if both ends are larger, the stretch-valve mechanism 3430 has a "dumbbell" shape. An exemplary configuration of a dumbbell shaped stretch-valve tube is described hereinbelow.

The longitudinal length of the hollow anchor portion 3532 is as long as desired to be longitudinally fixedly secured within the inflation lumen 3522 when installed in place. The tube, from its shape alone, can provide the securing connection but, also, an adhesive can be used in any manner, one of which includes creating a proximal port as shown in the above embodiments and utilizing the dipped exterior to form the fixed connection. The distal end of the hollow anchor portion 3532 in this exemplary embodiment is at a proximal side of the balloon 3502. The distal end of the stretch-valve mechanism 3530 can be nearer to the inflation port 3524, but not at or distal of the inflation port 3524; both ends of the hollow anchor portion 3532 can be proximal, at, or distal to the proximal end of the balloon 3502 and selection of this position is dependent upon the amount of stretch that is desired to actuate the stretch-valve of the inventive catheter 3500 as described below. In the exemplary embodiment of FIG. 35, the intermediate bias device 3534, such as a spring, is connected at its proximal end to the hollow anchor portion 3532 and the stopper 3536 is connected to the distal end of the bias device 3534. The bias device 3534 is located at the inflation port 3524 but not to obstruct fluid flow through the inflation port 3524. The stopper 3536, in contrast, is a solid cylinder having the same outer diameter as the hollow anchor portion 3532. The entire mechanism 3530 is sized to be slidably disposed in the inflation lumen 3522 while, at the same time, to provide a fluid-tight seal at the stopper 3536 so that liquid cannot pass from one side of the stopper 3536 to the other side within the inflation lumen 3522. The stopper 3536 is located distal of the inflation port 3524. To prevent distal movement of the stopper 3536, a restrictor 3538 is provided distal of the stopper 3536. The bias device 3534, therefore, spans the inflation port 3524. Because the stopper 3536 must traverse the inflation port 3524, it must be just distal of the inflation port 3524 but the hollow anchor portion 3532 can be located anywhere proximal of the inflation port 3524. While the length of the bias device 3534 needs to be sufficient to span the inflation port 3524, it can be as long as desired, which will depend on where the hollow anchor portion 3532 resides. As the catheter 3500 stretches more at its proximal end and less at its distal end when pulled from the proximal end, the hollow anchor portion 3522 can be further proximal in the inflation lumen 3522 than shown, and can even be very close to or at the proximal end of the inflation lumen 3522.

In such a configuration, therefore, any proximal movement of the catheter 3500 at or proximal to the inflation port 3524 will also move the stretch-valve mechanism 3530 proximally; in other words, the stopper 3536 slides proximally within the inflation lumen 3522 from distal of the inflation port 3524 to a proximal side of the inflation port 3524. When the proximal end of the catheter 3500 is pulled to move the stopper 3536 across the inflation port 3524 with a force that is no greater than just before injury would occur to the bladder-urethral junction or the urethra if the catheter 3500 was still inflated when the force was imparted, fluid in the balloon 3542 can exit distally out the inflation lumen 3522. In an exemplary embodiment of the stretch valve of FIG. 35, a pulling force in a range of 1 to 15 pounds will cause the stretch-valve mechanism 3530 to slide proximally to place the stopper 3536 just proximal of the inflation port 3524, i.e., the deflation point of the stretch-valve shown in FIG. 35. In another exemplary embodiment, the range of force required to meet the deflation point is between 1 and 5 pounds, in particular, between 1.5 and 2 pounds. When the stopper 3536 traverses the inflation port 3524, the balloon 3542 automatically deflates and the inflating fluid exits into the bladder out the distal end of the inflation lumen 3532, which is open at the distal end of the catheter 3500.

Figure 36:
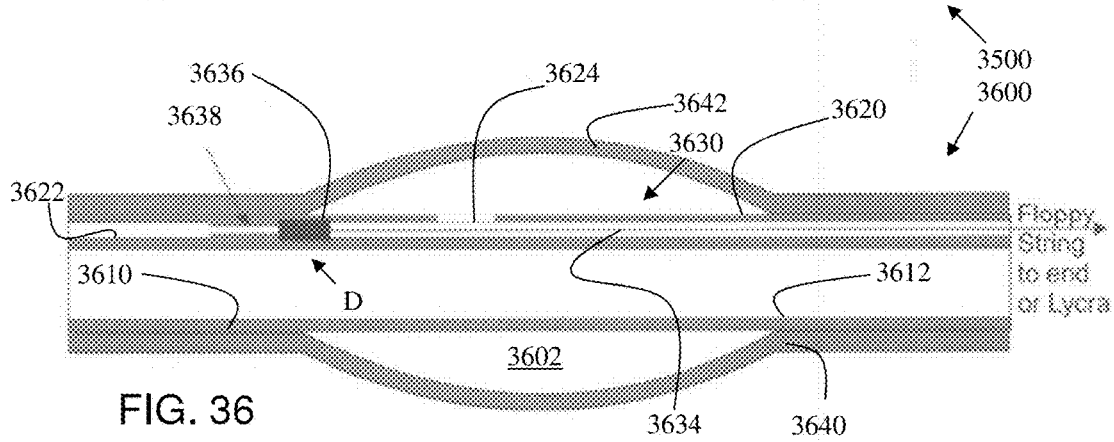
FIG. 36 is a fragmentary, enlarged, longitudinal cross-sectional view of a balloon portion of an additional exemplary embodiment of an automatically deflating, stretch valve urinary balloon catheter according to the invention with the balloon in a partially inflated state and the stretch valve in an unactuated state.

FIG. 36 illustrates the balloon portion of the inventive catheter 3600 with the balloon 3602 in a partially inflated state. An annular inner lumen wall 3610 defines therein a drainage lumen 3612. At one or more circumferential longitudinal extents about the inner lumen wall 3610, an inflation lumen wall 3620 defines an inflation lumen 3622 and a balloon inflation port 3624 fluidically connected to the inflation lumen 3622; in the inventive catheter, there can be more than one inflation lumen 3622 and corresponding inflation port 3624 even though only one is shown herein. No lumen plug closes the inflation lumen 3622 distal of the inflation port 3624. In this exemplary embodiment, a stretch-valve mechanism 3630 serves to plug the inflation lumen 3622 distal of the inflation port 3624 as described in further detail below. An outer wall 3640 covers all of the interior walls 3610 and 3620 in a fluid-tight manner and forms the exterior of the balloon 3642 but does not cover the distal end of the inflation lumen 3622. The outer wall 3640 is formed in any way described herein and is not discussed in further detail here.

The stretch-valve mechanism 3630 is disposed in the inflation lumen 3622 to not hinder inflation of the balloon 3602 with inflating fluid. A non-illustrated proximal anchor is disposed in the inflation lumen 3620 proximal of the inflation port 3624. The proximal anchor can be any size or shape that accommodates unhindered fluid flow through the inflation lumen 3622, one exemplary inner diameter of the hollow anchor portion is a tube substantially equal to the diameter of the inflation lumen 3622 with an outer diameter just slightly larger than the diameter of the inflation lumen 3622 (e.g., the thickness of the tube can be between 0.07 mm and 0.7 mm). The longitudinal length of this hollow anchor can be as long as desired to be longitudinally fixedly secured within the inflation lumen 3622 when installed in place. The anchor in this exemplary embodiment is at or near the non-illustrated proximal end of the inflation lumen 3622. The distal end of the stretch-valve mechanism 3630 is distal of the inflation port 3624. In the exemplary embodiment of FIG. 36, the stretch-valve mechanism 3630 also includes an intermediate cord 3634, either inelastic or elastic, connected at its proximal end to the anchor. A stopper 3636 is connected to the distal end of the cord 3634. The cord 3634 is located at the inflation port 3624 but not to obstruct fluid flow through the inflation port 3624. The stopper 3636, in contrast, is a solid cylinder having the a diameter that allows it to slidably move within the inflation lumen 3622 when the cord 3634 pulls it but, at the same time, to provide a fluid-tight seal so that liquid cannot pass from one side of the stopper 3636 to the other side within the inflation lumen 3622. The stopper 3636 is located distal of the inflation port 3624. To prevent distal movement of the stopper 3636, a restrictor 3638 is provided distal of the stopper 3636. The cord 3634, therefore, spans the inflation port 3624. Because the stopper 3636 must traverse the inflation port 3624, it must be just distal of the inflation port 3624 but the anchor can be located anywhere proximal of the inflation port 3624. While the length of the cord 3634 needs to be sufficient to span the inflation port 3624, it can be as long as desired, which will depend on where the anchor resides. As the catheter 3600 stretches more at its proximal end and less at its distal end when pulled from the proximal end, the anchor can be very close to or at the proximal end of the inflation lumen 3622. It can even be attached to the luer connector half that prevents fluid from flowing out the proximal end of the inflation lumen 3622.

In such a configuration, therefore, any proximal movement of the catheter 3600 at the proximal end where the anchor resides will also move the stretch-valve mechanism 3630 proximally; in other words, the stopper 3636 slides proximally within the inflation lumen 3622 from distal of the inflation port 3624 to a proximal side of the inflation port 3624. When the proximal end of the catheter 3600 is pulled to move the stopper 3636 across the inflation port 3624 with a force that is no greater than just before injury would occur to the urethrovesical junction or the urethra if the catheter 3600 was still inflated when the force was imparted, fluid in the balloon 3642 can exit distally out the inflation lumen 3622. In an exemplary embodiment of the stretch valve of FIG. 36, a pulling force in a range of 1 to 15 pounds will cause the stretch-valve mechanism 3630 to slide proximally to place the stopper 3636 just proximal of the inflation port 3624, i.e., the deflation point of the stretch-valve shown in FIG. 36. In another exemplary embodiment, the range of force required to meet the deflation point is between 1 and 5 pounds, in particular, between 1.5 and 2 pounds. When the stopper 3636 traverses the inflation port 3624, the balloon 3642 automatically deflates and the inflating fluid exits into the bladder out the distal end of the inflation lumen 3622, which is open at the distal end of the catheter 3600.

An alternative exemplary embodiment combines the embodiments of FIGS. 30 and 36 to tether the tube 2820 to the proximal end of the catheter.

In each of the embodiments of FIGS. 33 to 36, deflation of the balloon 3342, 3442, 3542, 3642 out through the inflation lumen 3322, 3422, 3522, 3622 can be enhanced by creating a separate deflation port D between the stopper 3336, 3436, 3536, 3636 and the drain lumen 3312, 3412, 3512, 3612 at the rest or steady state position of the stopper 3336, 3436, 3536, 3636 (shown in FIGS. 33 to 36). In such a configuration, when the stopper 3336, 3436, 3536, 3636 moves downstream of the inflation port 3324, 3424, 3524, 3624, not only will the inflation fluid exit the distal (upstream) end of the inflation lumen 3322, 3422, 3522, 3622, but it will also exit directly into the drain lumen 3312, 3412, 3512, 3612. It is noted that, when the stopper 3336, 3436, 3536, 3636 moves only slightly downstream but not at or past the inflation port 3324, 3424, 3524, 3624, the deflation port D will connect the drain lumen 3312, 3412, 3512, 3612 to the inflation lumen 3322, 3422, 3522, 3622 fluidically. This is not disadvantageous in in these configurations because these lumens will be connected already through the distal ends thereof in the drainage organ (e.g., the bladder).

FIG. 37 illustrates the balloon portion of the inventive catheter 3700 with the balloon 3742 in a partially inflated state. An annular inner lumen wall 3710 defines therein a drainage lumen 3712. At one or more circumferential longitudinal extents about the inner lumen wall 3710, an inflation lumen wall 3720 defines an inflation lumen 3722 and a balloon inflation port 3724 fluidically connected to the inflation lumen 3722; in the inventive catheter, there can be more than one inflation lumen 3722 and corresponding inflation port 3724 even though only one is shown herein. A lumen plug 3736 fluidically closes the inflation lumen 3722 distal of the inflation port 3724 so that an inflation fluid 3702 is directed into the balloon 3742. The lumen plug 3736 can plug any point or extent from the inflation port 3724 distally. An outer wall 3740 covers an of the interior walls 3710 and 3720 in a fluid-tight manner and forms the exterior of the balloon 3742 but does not cover the distal end of the drainage lumen 3712. The outer wall 3740 is formed in any way described herein and is not discussed in further detail here.

In this exemplary embodiment, a hollow, stretch-valve tube 3730 is disposed in the drainage lumen 3712 to not hinder drainage of the fluid to be drained (e.g., urine). While the diameter of the stretch-valve tube 3730 can be any size that accommodates substantially unhindered fluid flow through the drainage lumen 3712, one exemplary inner diameter of the stretch-valve tube 3730 is substantially equal to the diameter of the drainage lumen 3712 and the outer diameter of the stretch-valve tube 3730 is just slightly larger than the diameter of the drainage lumen 3712 (e.g., the wall thickness of the tube can be between 0.07 mm and 0.7 mm). Another exemplary embodiment of the stretch-valve tube 3730 has one or more of the proximal and distal ends thereof larger in outer diameter than an intermediate portion of the stretch-valve tube 3730. Thus, if one end is larger, the stretch-valve tube 3730 has a "club" shape and, if both ends are larger, the stretch-valve tube 3730 has a "dumbbell" shape. An exemplary configuration of a dumbbell shaped stretch-valve tube is described hereinbelow.

The proximal end of the stretch-valve tube 3730 in this exemplary embodiment is proximal of a proximal end of a deflation port 3760. The distal end of the stretch-valve tube 3730 is not distal of the distal end of the balloon 3742 so that the balloon 3742 can be deflated; the distal end can be anywhere between the two ends of the balloon 3742 but is shown in an intermediate position in FIG. 37. The distal end of the stretch-valve tube 3730 is at a distance S distal of the deflation port 3760 and selection of this distance S is dependent upon the amount of stretch required to actuate the stretch-valve of the inventive catheter 3700 as described below. In the exemplary embodiment of FIG. 37, the longitudinal length of the deflation port 3760 is shown as less than one half of the longitudinal length of the stretch-valve tube 3730. The deflation port 3760 is formed through the inner lumen wall 3710 and the stretch-valve tube 3730 is positioned to overlap at least the deflation port 3760. In this manner, a portion of the outer surface of the distal end of the stretch-valve tube 3730 closes off the deflation port 3760 to prevent fluid communication between the balloon 3742 and the drainage lumen 3712 through the deflation port 3760.

Exemplary embodiments for securing the stretch-valve tube 3730 in the catheter 3700 include a proximal anchor 3732 in the drainage lumen 3710 disposed away from the deflation port 3760, here proximally. The proximal anchor 3732 can be any size or shape that accommodates substantially unhindered fluid flow through the drainage lumen 3712, one exemplary inner diameter of the hollow anchor 3732 being a tube or ring substantially equal to the diameter of the drainage lumen 3712 with an outer diameter just slightly larger than the diameter of the drainage lumen 3712 (e.g., the thickness of the tube can be between 0.07 mm and 0.7 mm). The longitudinal length of this hollow anchor 3732 can be as long as desired but just enough to longitudinally fixedly secure the stretch-valve tube 3730 within the drainage lumen 3712 when installed in place. The anchor 3732 in this exemplary embodiment is at the proximal end of the balloon 3742 but can be further inside the balloon 3742 (distal) or entirely proximal of the balloon 3742. In an exemplary embodiment, the anchor 3732 has a stepped distal orifice that permits the proximal end of the stretch-valve tube 3730 to be, for example, press-fit therein for permanent connection. In another exemplary embodiment, the anchor 3732 is an adhesive or glue that fixes the proximal end of the stretch-valve tube 3730 longitudinally in place within the drainage lumen 3712. The adhesive can be the same material as any or all of the walls 3710, 3720, 3740 or it can be a different material. In an exemplary non-illustrated embodiment where a fixation port or set of fixation ports are formed through the inner wall 3710 proximal of the proximal-most end of the balloon 3742 and about the proximal end of the stretch-valve tube 3730, if the outer wall 3740 is formed by a dipping of the interior parts into a liquid bath of the same material as, for example, a dual lumen extrusion including the inner wall 3710 and the inflation lumen wall 3720, then, when set, the outer wall 3740 will be integral to both the inner wall 3710 and the inflation lumen wall 3720 and will be fixedly connected to the stretch-valve tube 3730 through the fixation port(s). (Further exemplary embodiments for securing the stretch-valve tube 3730 in the catheter 3700 are described below with regard to FIGS. 48 to 56.)

In such a configuration, therefore, any proximal movement of the catheter 3700 at or proximal to the deflation port 3760 will also move the stretch-valve tube 3730 proximally; in other words, the distal end of the stretch-valve tube 3730 can slide within the drainage lumen 3712 in a proximal direction. When the proximal end of the catheter 3700 is pulled to a force that is no greater than just before injury would occur to the bladder-urethral junction or to the urethra if the catheter 3700 was still inflated when the force was imparted, the force will cause the stretch-valve tube 3730 to slide proximally and place the distal end of the stretch-valve tube 3730 just proximal of the deflation port 3760, e.g., with a pulling force in a range of 1 to 15 pounds. In another exemplary embodiment, the range of force required to meet the deflation point is between 1 and 5 pounds, in particular, between 1.5 and 2 pounds.

When the deflation point of the stretch-valve tube 3730 occurs, the interior of the balloon 3742 becomes fluidically connected directly into the drainage lumen 3712 (which is open to the interior of the bladder 2020 and to the non-illustrated, proximal drain bag) and, due to the fact that the bladder is relatively unpressurized as compared to the balloon 3742, all internal pressure is released from the balloon 3742 to eject the inflating fluid 3702 directly into the drainage lumen 3712, thereby causing the balloon 3742 to deflate rapidly. Because there is no intermediate structure between the balloon inflating fluid 3702 and the drainage lumen 3712, the rate at which the balloon 3742 deflates is fast. One way to speed up deflation can be to shape the deflation port 3760 in the form of a funnel outwardly expanding in a direction from the outer wall 3740 towards the interior of the catheter 3700. Another way to speed up deflation can be the presence of two or more deflation ports 3760 about the circumference of the inner lumen wall 3710 and/or an enlargement of the cross-sectional area of the deflation port 3760.

FIG. 38 illustrates a balloon portion of the inventive catheter 3800 with a balloon 3842 in a partially inflated state. An annular inner lumen wall 3810 defines therein a drainage lumen 3812. At one or more circumferential longitudinal extents about the inner lumen wall 3810, an inflation lumen wall 3820 defines an inflation lumen 3822 and a balloon inflation port 3824 fluidically connected to the inflation lumen 3822; in the inventive catheter, there can be more than one inflation lumen 3822 and corresponding inflation port 3824 even though only one is shown herein. A lumen plug 3836 fluidically closes the inflation lumen 3822 distal of the inflation port 3824 so that all inflation fluid 3802 is directed into the balloon 3842. The lumen plug 3736 can plug any point or extent from the inflation port 3724 distally. An outer wall 3840 covers all of the interior walls 3810 and 3820 in a fluid-tight manner and forms the exterior of the balloon 3842 but does not cover the distal end of the drainage lumen 3812. The outer wall 3840 is formed in any way described herein and is not discussed in further detail here.

In this exemplary embodiment, a hollow, stretch-valve tube 3830 is disposed in the drainage lumen 3812 to not hinder drainage of the fluid to be drained (e.g., urine). While the diameter of the stretch-valve tube 3830 can be any size that accommodates substantially unhindered fluid flow through the drainage lumen 3812, one exemplary inner diameter of the stretch-valve tube 3830 is substantially equal to the diameter of the drainage lumen 3812 and the outer diameter of the stretch-valve tube 3830 is just slightly larger than the diameter of the drainage lumen 3812 (e.g., the wall thickness of the tube can be between 0.07 mm and 0.7 mm).

Another exemplary embodiment of the stretch-valve tube 3830 has one or more of the proximal and distal ends thereof larger in outer diameter than an intermediate portion of the stretch-valve tube 3830. Thus, if one end is larger, the stretch-valve tube 3830 has a "club" shape and, if both ends are larger, the stretch-valve tube 3830 has a "dumbbell" shape. An exemplary configuration of a dumbbell shaped stretch-valve tube is described hereinbelow.

The proximal end of the stretch-valve tube 3830 in this exemplary embodiment is proximal of a proximal end of a deflation port 3860. The longitudinal length of the deflation port 3860 is not distal of the distal end of the balloon 3842 so that the balloon 3842 can be deflated; the distal end can be anywhere between the two ends of the balloon 3842 but is shown in an intermediate position in FIG. 38. The distal end of the stretch-valve tube 3830 is at a distance S distal of the deflation port 3860 and selection of this distance S is dependent upon the amount of stretch required to actuate the stretch-valve of the inventive catheter 3800 as described below. In the exemplary embodiment of FIG. 38, the longitudinal length of the deflation port 3760 is shown as less than one half of the longitudinal length of the stretch-valve tube 3830. The drainage port 3860 is formed through the inner lumen wall 3810 and the stretch-valve tube 3830 is positioned to overlap at least the drainage port 3860. In this manner, a portion of the outer surface of the distal end of the stretch-valve tube 3830 closes off the drainage port 3860 to prevent fluid communication between the balloon 3842 and the drainage lumen 3812 through the drainage port 3860.

In this exemplary embodiment, in comparison to the embodiment of FIG. 37, a second drainage port 3862 is provided in the inner lumen wall 3810 aligned with the drainage port 3860, and both drainage ports 3860, 3862 are aligned with the inflation port 3824. As such, when the stretch-valve tube 3830 moves proximally to uncover the drainage ports 3860, 3862, inflation fluid 3802 from inside the balloon 3842 exits from both the inflation port 3824 and the drainage port 3860.

To secure the stretch-valve tube 3830 in the catheter 3800, a proximal anchor 3832 is disposed in the drainage lumen 3810 away from the deflation ports 3860, 3862, here proximally. The proximal anchor 3832 can be any size or shape that accommodates substantially unhindered fluid flow through the drainage lumen 3812, one exemplary inner diameter of the hollow anchor 3832 being a tube or ring substantially equal to the diameter of the drainage lumen 3812 with an outer diameter just slightly larger than the diameter of the drainage lumen 3812 (e.g., the thickness of the tube can be between 0.07 mm and 0.7 mm). The longitudinal length of this hollow anchor 3832 can be as long as desired but just enough to longitudinally fixedly secure the stretch-valve tube 3830 within the drainage lumen 3812 when installed in place. The anchor 3832 in this exemplary embodiment is at the proximal end of the balloon 3842 but can be further inside the balloon 3842 (distal) or entirely proximal of the balloon 3842. In an exemplary embodiment, the anchor 3832 has a stepped distal orifice that permits the proximal end of the stretch-valve tube 3830 to be, for example, press-fit therein for permanent connection. In another exemplary embodiment, the anchor 3832 is an adhesive or glue that fixes the proximal end of the stretch-valve tube 3830 longitudinally in place within the drainage lumen 3812. The adhesive can be the same material as any or an of the walls 3810, 3820, 3840 or it can be a different material. In an exemplary non-illustrated embodiment where a fixation port or set of fixation ports are formed through the inner wall 3810 proximal of the proximal-most end of the balloon 3842 and about the proximal end of the stretch-valve tube 3830, if the outer wall 3840 is formed by a dipping of the interior parts into a liquid bath of the same material as, for example, a dual lumen extrusion including the inner wall 3810 and the inflation lumen wall 3820, then, when set, the outer wall 3840 will be integral to both the inner wall 3810 and the inflation lumen wall 3820 and will be fixedly connected to the stretch-valve tube 3820 through the fixation port(s). (Further exemplary embodiments for securing the stretch-valve tube 3830 in the catheter 3800 are described below with regard to FIGS. 48 to 56.)

In such a configuration, therefore, any proximal movement of the catheter 3800 at or proximal to the drainage ports 3860, 3862 will also move the stretch-valve tube 3830 proximally; in other words, the distal end of the stretch-valve tube 3830 can slide within the drainage lumen 3812 in a proximal direction. When the proximal end of the catheter 3800 is pulled to a force that is no greater than just before injury would occur to the bladder-urethral junction or the urethra if the catheter 3800 was still inflated when the force was imparted, the force will cause the stretch-valve tube 3830 to slide proximally to place the distal end of the stretch-valve tube 3830 just proximal of the drainage ports 3860, 3862, e.g., with a pulling force in a range of 1 to 15 pounds. In another exemplary embodiment, the range of force required to meet the deflation point is between 1 and 5 pounds, in particular, between 1.5 and 2 pounds.

When the deflation point of the stretch-valve tube 3830 occurs, the interior of the balloon 3842 becomes fluidically connected directly into the drainage lumen 3812 (which is open to the interior of the bladder 2020 and to the non-illustrated, proximal drain bag) and, due to the fact that the bladder is relatively unpressurized as compared to the balloon 3842, all internal pressure is released from the balloon 3842 to eject the inflating fluid 3802 directly into the drainage lumen 3812, thereby causing the balloon 3842 to deflate rapidly. Because there is no intermediate structure between the balloon inflating fluid 3802 and the drainage lumen 3812, the rate at which the balloon 3842 deflates is fast. One way to speed up deflation can be to shape the drainage ports 3860, 3862 in the form of a funnel outwardly expanding in a direction from the outer wall 3840 towards the interior of the catheter 3800. Another way to speed up deflation can be to have two or more drainage ports 3860 about the circumference of the inner lumen wall 3810 and/or to enlarge the cross-sectional area of the drainage ports 3860, 3862.

Figure 39:
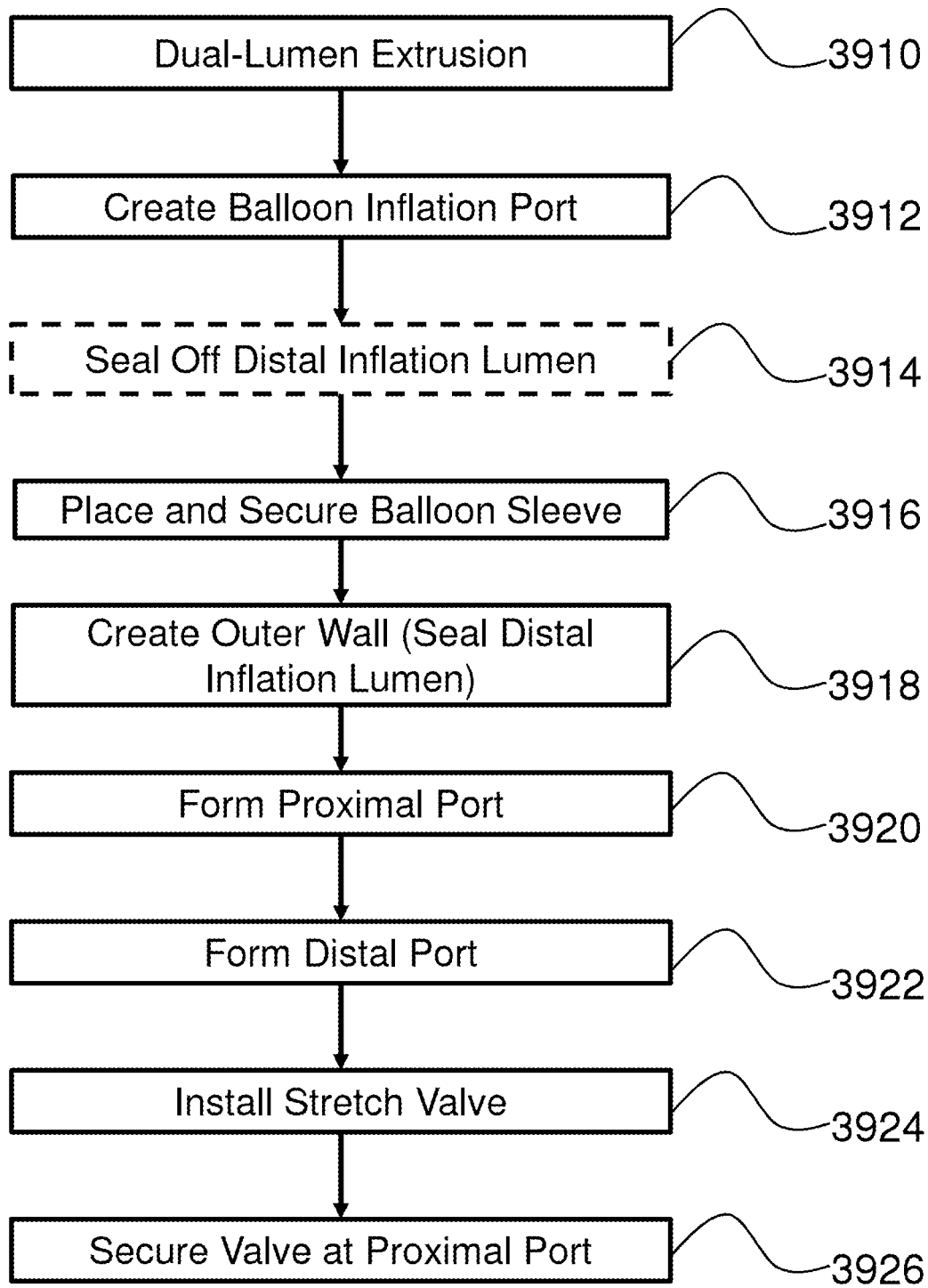
FIG. 39 is a flow chart of exemplary embodiments of processes for making a catheter according to the invention.

Reference is made to the flow chart of FIG. 39 to explain one exemplary embodiment of a process for making a catheter according to the embodiment of FIGS. 21 to 23.

The catheter starts, in Step 3910 with a dual lumen extrusion of latex. This extrusion, therefore, defines the annular inner lumen wall 2110 with the drainage lumen 2112 and, at one or more circumferential longitudinal extents about the inner lumen wall 2110, an inflation lumen wall 2120 with the inflation lumen 2122. The dual lumen, therefore, already includes both the drainage lumen 2112 and the inflation lumen 2122. Both lumen 2112, 2122, however, are extruded without obstruction and without radial ports. Therefore, in order to have the inflation port 2124, a radial hole needs to be created between the outside surface of the extrusion and the inflation lumen.

In step 3912, the balloon inflation port 2124 is made to fluidically connect the environment of the extrusion to the inflation lumen 2122.

Sealing off of the distal end of the inflation lumen 2122 can be performed in Step 3914 by inserting or creating a plug 2126 therein or the sealing can occur simultaneously with the creation of the outer wall 2140 below.

In step 3916, a balloon sleeve 2130 is placed about the inflation port 2124 and is fixed to the exterior of the inflation lumen wall 2120 at both ends to define a fluid-tight balloon interior 2200 therebetween. As such, inflation of the balloon 2210 can occur through the inflation lumen 2122. For example, the tube 2130 making up the inner balloon wall is slid over the distal end of the dual-lumen extrusion to cover the inflation port 2124 and is fluid-tightly sealed to the inner multi-lumen extrusion at both ends of the tube but not in the intermediate portion. This tube can be made of latex as well and, therefore, can be secured to the latex multi-lumen extrusion in any known way to bond latex in a fluid-tight manner.

In step 3918, the entire sub-assembly is covered with the outer wall 2140. For example, the entire sub-assembly is dipped into latex in its liquid form to create the outer wall 2140. In the alternative embodiment where a distal inflation lumen plug is not used, the latex can be allowed to enter at least a portion of the distal end of the inflation lumen 2122 but not so far as to block the inflation port 2124. When the latex cures, the balloon 2210 is fluid tight and can only be fluidically connected to the environment through the proximal-most opening of the inflation port, which is fluidically connected to the inflation lumen 2122. In this process, the inner wall 2110, the inflation lumen wall 2120, the plug 2126, the balloon wall 2130, and the outer wall 2140 are all made of the same latex material and, therefore, together form a very secure water-tight balloon 2210.

The sub-process described in Steps 3910 to 3920 can be skipped if desired and, instead, completed by utilizing a standard Foley catheter, on which the following steps are performed.

The stretch valve is now created. A proximal port 2150 is formed through the outer wall 2140 and through the inflation lumen wall 2020 in step 3920. A distal port 2160 is formed through the outer wall 2140 and through the inflation lumen wall 2020 in step 3922. Then, in step 3924, the stretch-valve tube 2220 is inserted through either one of the proximal or distal ports 2150, 2160 such that the proximal port 2150 overlaps at least a portion of the proximal end of the stretch-valve tube 2220 and the distal port 2160 overlaps at least a portion of the distal end of the stretch-valve tube 2220. In this manner, two portions of the outer surface of the proximal end of the stretch-valve tube 2220 at the proximal and distal ports 2150, 2160 are exposed to the environment but there is no fluid communication with the inflation lumen 2122 and the proximal or distal ports 2150, 2160.

In Step 3926, the proximal port 2150 is used to secure the stretch-valve tube 2220 in the catheter 2100. In one exemplary embodiment, the proximal port 2150 is filled with a material that fixes the proximal end of the stretch-valve tube 2220 to at least one of the outer wall 2140 and the inflation lumen wall 2020. In an exemplary embodiment, an adhesive bonds the proximal end of the stretch-valve tube 2220 to both the outer wall 2140 and the inflation lumen wall 2120. In another exemplary embodiment, a portion of the present sub-assembly is dipped into latex in its liquid form to plug the proximal port 2150 and fixedly secure the stretch-valve tube 2220 to both the outer wall 2140 and the inflation lumen wall 2120. When the latex cures, the connection at the proximal port 2150 is fluid tight and no longer permits fluidic connection to the environment therethrough. In this process, therefore, the filled proximal port 2150, the inflation lumen wall 2120, and the outer wall 2140 are all made of the same latex material and, therefore, together form a very secure water-tight connection. (Further exemplary embodiments for securing the stretch-valve tube 2220 in the catheter 2100 are described below with regard to FIGS. 48 to 56.)

In such a configuration, therefore, any proximal movement of the catheter 2100 at or proximal of the proximal port 2150 will also move the stretch-valve tube 2220 proximally; in other words, the distal end of the stretch-valve tube 2220 can slide within the inflation lumen 2122 in a proximal direction.

Reference is also made to the flow chart of FIG. 39 to explain one exemplary embodiment of a process for making a catheter according to the embodiment of FIGS. 24 to 26.

The catheter starts, in Step 3910 with a dual lumen extrusion of latex. This extrusion, therefore, defines the annular inner lumen wall 2410 with the drainage lumen 2412 and, at one or more circumferential longitudinal extents about the inner lumen wall 2410, an inflation lumen wall 2420 with the inflation lumen 2422. The dual lumen, therefore, already includes both the drainage lumen 2412 and the inflation lumen 2422. Both lumens 2412, 2422, however, are extruded without obstruction and without radial ports. Therefore, in order to have the inflation port 2424, a radial hole needs to be created between the outside surface of the extrusion and the inflation lumen.

In Step 3912, the balloon inflation port 2424 is made to fluidically connect the environment of the extrusion to the inflation lumen 2422.

Sealing off of the distal end of the inflation lumen 2422 can be performed in Step 3914 by inserting or creating a plug 2426 therein or the sealing can occur simultaneously with the creation of the outer wall 2440 below.

In Step 3916, a balloon sleeve 2430 is placed about the inflation port 2424 and is fixed to the exterior of the inflation lumen wall 2420 at both ends to define a fluid-tight balloon interior 2200 therebetween. As such, inflation of the balloon 2240 can occur through the inflation lumen 2422. For example, the tube 2430 making up the inner balloon wall is slid over the distal end of the dual-lumen extrusion to cover the inflation port 2424 and is fluid-tightly sealed to the inner multi-lumen extrusion at both ends of the tube but not in the intermediate portion. This tube can be made of latex as well and, therefore, can be secured to the latex multi-lumen extrusion in any known way to bond latex in a fluid-tight manner.

In Step 3918, the entire sub-assembly is covered with the outer wall 2440. For example, the entire sub-assembly is dipped into latex in its liquid form to create the outer wall 2440. In the alternative embodiment where a distal inflation lumen plug is not used, the latex can be allowed to enter at least a portion of the distal end of the inflation lumen 2422 but not so far as to block the inflation port 2424. When the latex cures, the balloon 2240 is fluid tight and can only be fluidically connected to the environment through the proximal-most opening of the inflation port, which is fluidically connected to the inflation lumen 2422. In this process, the inner wall 2410, the inflation lumen wall 2420, the plug 2426, the balloon wall 2430, and the outer wall 2440 are all made of the same latex material and, therefore, together form a very secure water-tight balloon 2240.

The sub-process described in Steps 3910 to 3920 can be skipped if desired and, instead, completed by utilizing a standard Foley catheter, on which the following Steps are performed.

The stretch valve is now created. A proximal port 2450 is formed through the outer wall 2440 and through the inflation lumen wall 2020 in Step 3920. A distal port 2460 is formed through the inner wall 2410 into the inflation lumen 2422 in Step 3922. Then, in Step 3924, the stretch-valve tube 2520 is inserted through either one of the proximal or distal ports 2450, 2460 such that the proximal port 2450 overlaps at least a portion of the proximal end of the stretch-valve tube 2520 and the distal port 2460 overlaps at least a portion of the distal end of the stretch-valve tube 2520. In this manner, one portion of the outer surface of the proximal end of the stretch-valve tube 2520 at the proximal port 2450 is exposed to the drain lumen 2412 and another portion of the outer surface of the distal end of the stretch-valve tube 2520 at the distal port 2460 is exposed to the environment but there is no fluid communication with the inflation lumen 2422 to either of the proximal or distal ports 2450, 2460.

In Step 3926, the proximal port 2450 is used to secure the stretch-valve tube 2520 in the catheter 2400. In one exemplary embodiment, the proximal port 2450 is filled with a material that fixes the proximal end of the stretch-valve tube 2520 to at least one of the outer wall 2440 and the inflation lumen wall 2020. In an exemplary embodiment, an adhesive bonds the proximal end of the stretch-valve tube 2520 to both the outer wall 2440 and the inflation lumen wall 2420. In another exemplary embodiment, a portion of the present sub-assembly is dipped into latex in its liquid form to plug the proximal port 2450 and fixedly secure the stretch-valve tube 2520 to both the outer wall 2440 and the inflation lumen wall 2420. When the latex cures, the connection at the proximal port 2450 is fluid tight and no longer permits fluidic connection to the environment therethrough. In this process, therefore, the filled proximal port 2450, the inflation lumen wall 2420, and the outer wall 2440 are all made of the same latex material and, therefore, together form a very secure water-tight connection. (Further exemplary embodiments for securing the stretch-valve tube 2520 in the catheter 2400 are described below with regard to FIGS. 48 to 56.)

In such a configuration, therefore, any proximal movement of the catheter 2400 at or proximal of the proximal port 2450 will also move the stretch-valve tube 2520 proximally; in other words, the distal end of the stretch-valve tube 2520 can slide within the inflation lumen 2422 in a proximal direction.

Figure 40:
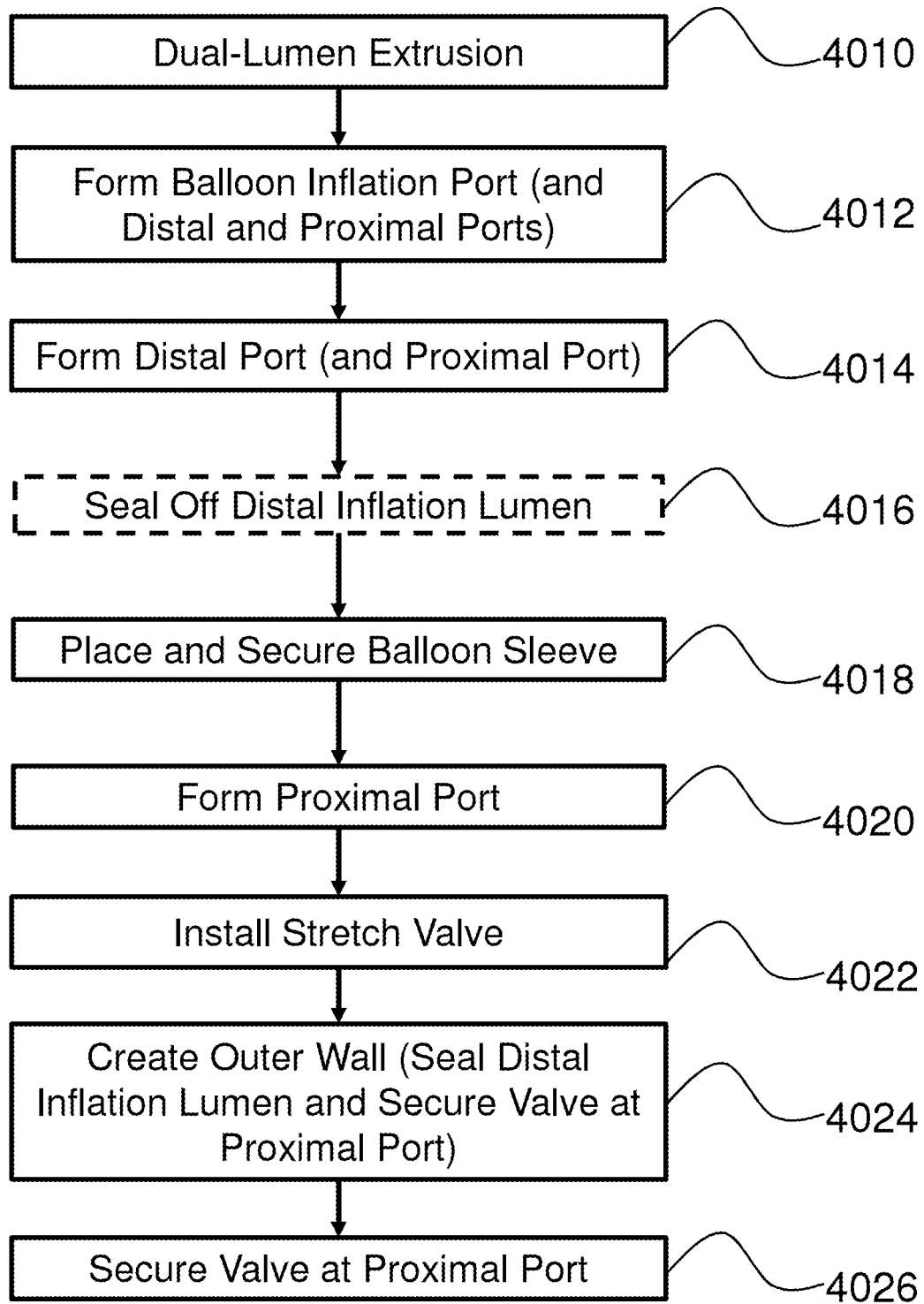
FIG. 40 is a flow chart of exemplary embodiments of other processes for making a catheter according to the invention.

Reference is made to the flow chart of FIG. 40 to explain one exemplary embodiment of a process for making a catheter according to the embodiment of FIGS. 27 to 29.

The catheter starts, in Step 4010 with a dual lumen extrusion of latex. This extrusion, therefore, defines the annular inner lumen wall 2710 with the drainage lumen 2712 and, at one or more circumferential longitudinal extents about the inner lumen wall 2710, an inflation lumen wall 2720 with the inflation lumen 2722. The dual lumen, therefore, already includes both the drainage lumen 2712 and the inflation lumen 2722. Both lumen 2712, 2722, however, are extruded without obstruction and without radial ports. Therefore, in order to have the inflation port 2724, a radial hole needs to be created between the outside surface of the extrusion and the inflation lumen.

In Step 4012, the balloon inflation port 2724 is made to fluidically connect the environment of the extrusion to the inflation lumen 2722.

Different from the other exemplary embodiments described, a distal port 2760 is created in Step 4014 before, after, or at the same time as the balloon inflation port 2724. The distal port 2760 connects the environment to the interior of the drain lumen 2712. In an exemplary embodiment, the distal port 2760 is proximal of the balloon inflation port 2724.

Sealing off of the distal end of the inflation lumen 2722 can be performed in Step 4016 by inserting or creating a plug 2726 therein or the sealing can occur simultaneously with the creation of the outer wall 2740 below.

In Step 4018, a balloon sleeve 2730 is placed about the inflation port 2724 and the distal port 2760 and is fixed to the exterior of the inflation lumen wall 2720 at both ends to define a fluid-tight balloon interior 2200 therebetween. As such, inflation of the balloon 2810 can occur through the inflation lumen 2722. For example, the tube 2730 making up the inner balloon wall is slid over the distal end of the dual-lumen extrusion to cover the inflation port 2724 and is fluid-tightly sealed to the inner multi-lumen extrusion at both ends of the tube but not in the intermediate portion. This tube can be made of latex as well and, therefore, can be secured to the latex multi-lumen extrusion in any known way to bond latex in a fluid-tight manner.

Installation of the stretch valve occurs by forming a proximal port 2750 through the inflation lumen wall 2020 in Step 4020. Then, in Step 4022, the stretch-valve tube 2820 is inserted through either one of the proximal or distal ports 2750, 2760 such that the proximal port 2750 overlaps at least a portion of the proximal end of the stretch-valve tube 2820 and the distal port 2760 overlaps at least a portion of the distal end of the stretch-valve tube 2820. In this manner, two portions of the outer surface of the proximal end of the stretch-valve tube 2820 at the proximal and distal ports 2750, 2760 are exposed to the environment but there is no fluid communication with the inflation lumen 2722 and the proximal or distal ports 2750, 2760. Alternatively, Steps 4022 can occur before 4018 to insert the stretch-valve tube 2820 before the balloon sleeve 2730 is placed and fixed. In such a case, the creation of the proximal port 2750 can occur before, after, or at the same time as creating the distal port 2760 and the balloon inflation port 2724, in which embodiment, all three ports 2724, 2750, 2760 can be created at the same time.

In Step 4024, the entire sub-assembly is covered with the outer wall 2740. For example, the entire sub-assembly is dipped into latex in its liquid form to create the outer wall 2740. In the alternative embodiment where a distal inflation lumen plug is not used, the latex can be allowed to enter at least a portion of the distal end of the inflation lumen 2722 but not so far as to block the inflation port 2724. When the latex cures, the balloon 2810 is fluid tight and can only be fluidically connected to the environment through the proximal-most opening of the inflation port, which is fluidically connected to the inflation lumen 2722. In this process, the inner wall 2710, the inflation lumen wall 2720, the plug 2726, the balloon wall 2730, and the outer wall 2740 are all made of the same latex material and, therefore, together form a very secure water-tight balloon 2810.

In previous embodiments, the proximal port 2750 pierced the outer wall 2740. In this exemplary embodiment, however, there is no need to do so. Here, the proximal port 2750 can be filled with material of the outer wall 2740 itself to fix the proximal end of the stretch-valve tube 2820 to at least one of the outer wall 2740 and the inflation lumen wall 2020. When the latex cures, the connection at the proximal port 2750 is fluid tight and no longer permits fluidic connection to the environment therethrough. In this process, therefore, the filled proximal port 2750, the inflation lumen wall 2720, and the outer wall 2740 are all made of the same latex material and, therefore, together, form a very secure water-tight connection. In an alternative exemplary embodiment, an adhesive can be used to bond the proximal end of the stretch-valve tube 2820 to the inflation lumen wall 2720.

(Further exemplary embodiments for securing the stretch-valve tube 2820 in the catheter 2700 are described below with regard to FIGS. 48 to 56.)

In such a configuration, therefore, any proximal movement of the catheter 2700 at or proximal of the proximal port 2750 will also move the stretch-valve tube 2820 proximally; in other words, the distal end of the stretch-valve tube 2820 can slide within the inflation lumen 2722 in a proximal direction.

Figure 41:
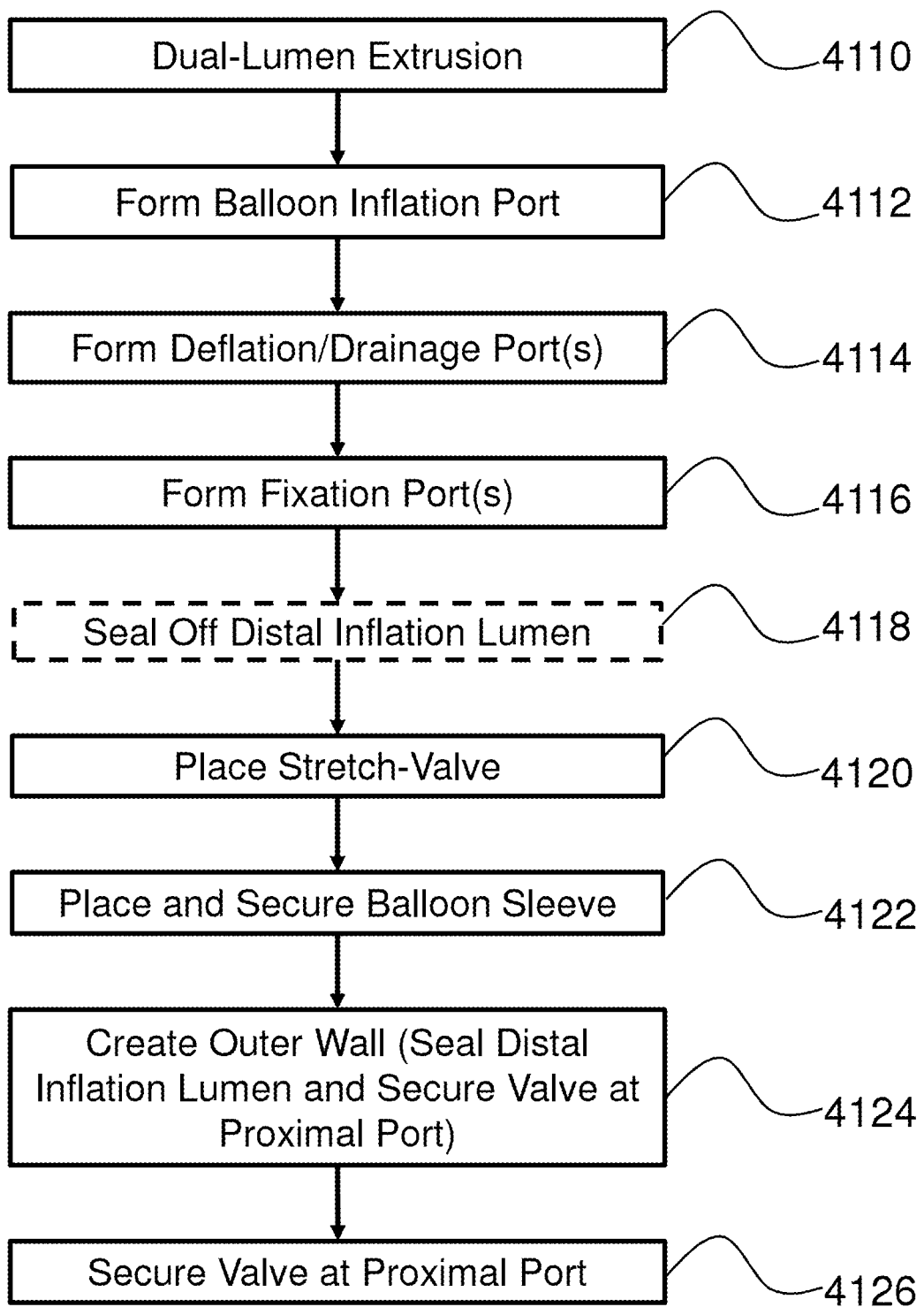
FIG. 41 is a flow chart of exemplary embodiments of further processes for making a catheter according to the invention.

Reference is made to the flow chart of FIG. 41 to explain one exemplary embodiment of a process for making a catheter according to the embodiment of FIGS. 37 and 38.

The catheter starts, in Step 4110 with a dual lumen extrusion of latex. This extrusion, therefore, defines the annular inner lumen wall 3710, 3810 with the drainage lumen 3712, 3812 and, at one or more circumferential longitudinal extents about the inner lumen wall 3710, 3810, an inflation lumen wall 3720, 3820 with the inflation lumen 3722, 3822. The dual lumen, therefore, already includes both the drainage lumen 2712, 2812 and the inflation lumen 2722, 2822. Both lumen 2712, 2722, 2812, 2822, however, are extruded without obstruction and without radial ports. Therefore, in order to have the inflation port 3724, 3824, a radial hole needs to be created between the outside surface of the extrusion and the inflation lumen.

In Step 4112, the balloon inflation port 3724, 3824 is made to fluidically connect the environment of the extrusion to the inflation lumen 3722, 3822.

Different from the other exemplary embodiments described, with regard to the embodiment of FIG. 37, the deflation port 3760 is created in Step 4114 before, after, or at the same time as the balloon inflation port 3724. The deflation port 3760 connects the interior of the balloon 3742 to the interior of the drain lumen 3712. In an exemplary embodiment, the deflation port 3760 is proximal of the balloon inflation port 3724 but can be at or distal thereof.

Different from the other exemplary embodiments described, with regard to the embodiment of FIG. 38, the drainage ports 3860 and 3862 are created in Step 4114 before, after, or at the same time as the balloon inflation port 3824. The drainage port 3860 connects the interior of the balloon 3842 to the interior of the drain lumen 2712 and the drainage port 3862 connects the interior of the inflation lumen 3822 to the interior of the drain lumen 2712. In an exemplary embodiment, the drainage ports 3860, 3862 are aligned with the balloon inflation port 3824 but they can be distal or proximal thereof. When aligned, a single through-hole can be made through the entire catheter, penetrating both the inflation and drainage channels 3712, 3722, 3812, 3822 and both walls 3710, 3720, 3810, 3820 of the dual lumen extrusion. Alternatively, the drainage ports 3860, 3862 can be spaced from one another with either one or neither aligned with the inflation port 3824.

In Step 4116, a fixation point 3732, 3832 is established at the outer wall 3710, 3810. At this fixation point 3732, 3832 are the measures for fixing the stretch-valve tube 3730, 3830 inside the drainage lumen 3712, 3812. The fixation point 3732, 3832 can be placed anywhere proximal of the drainage ports 3760, 3860, 3862. The fixation point 3732, 3832 is not aligned circumferentially with the inflation port 3724, 3824 as shown in FIGS. 37 and 38. In the exemplary embodiment shown, the fixation point 3732, 3832 is still within the proximal end of the balloon 3742, 3842 but it can equally be further proximal of the balloon 3742, 3842 to any point proximal within the drainage lumen 3712, 3812.

Sealing off of the distal end of the inflation lumen 3722, 3822 can be performed in Step 4118 by inserting or creating a plug 3736, 3836 therein or the sealing can occur before forming the fixation ports or just before or simultaneously with the creation of the outer wall 3740, 3840 below in Step 4124.

In Step 4120, the stretch-valve tube 3730, 3830 is inserted into the drainage lumen 3712, 3812 and aligned so that the stretch-valve tube 3730, 3830 covers all drainage ports 3760, 3860, 3862. The distal end of the stretch-valve tube 3730, 3830 is positioned at the distal distance S desired for operation of the stretch valve. For example, the distance can be up to 1 mm, up to 2 mm, up to 3 mm and up to even 1 or 2 cm. The distance S can also be dependent on the amount of stretch at the proximal end of the catheter as the displacement of the stretch-valve tube is proportional to the stretch of the catheter. For example, if the catheter is 500 mm long and is pulled 20%, then it will be 600 mm long (a 100 mm stretch). A 10 mm or longer stretch-valve tube made from a stiff material, such as metal (e.g., stainless steel, titanium, etc.) polycarbonate, polyimide, polyamide, polyurethane (Shore 55D-75D), and the like, located near the balloon of the catheter has its proximal end glued to the inside of the inflation or drainage lumen. When this catheter is stretched than 20%, then the distal tip of a 10 mm stretch valve will move 2 mm in the proximal direction. Accordingly, if the drainage port(s) is placed 2 mm proximal to the distal end of the stretch-valve tube (here, S=2 mm), it will remain sealed by the stretch-valve tube at a stretch of about 20%. But, when the catheter is pulled slightly more than 20% (or 2 mm), the drainage port will unseal and the inflation fluid within the balloon will discharge out the drainage port. As catheters vary among manufacturers, calibration of the percent stretch to the force required to stretch the catheter can be done for each different type of catheter. This force is defined in engineering terms as a modulus of the catheter and is a function of the modulus of the material and the effective wall thickness of the catheter. Low modulus materials and catheters will stretch more than high modulus materials and catheters when exposed to the same force. Exemplary catheters are those made from latex rubber or silicone rubber. Silicone rubber generally has a higher modulus than latex and, therefore, more force is required to stretch the catheter sufficiently to discharge the pressure within the balloon. Those of skill in the art, therefore, will understand that different stretch valves lengths can provided to dump the balloon pressure as a function of a tug-force on the different catheters made from the different materials and having different wall thicknesses. Accordingly, even though the stretch-valve tube distances are given, they are exemplary and can change for different catheters having different materials/thicknesses. As such, these exemplary distances for actuating the stretch-valve tube applies to all embodiments described herein but are not limited thereto.

If fixation through-holes 3732, 3832 exist and are within the inflation expanse of the balloon sleeve (not illustrated), then an adhesive can be used within the fixation through-holes 3732, 3832 to fix the proximal end of the stretch-valve tube 3730, 3830 thereat before attachment of the balloon sleeve. If the fixation through-holes 3732, 3832 are within the expanse of the balloon sleeve but only overlap at the fixed proximal end of the balloon sleeve (not illustrated), then the same adhesive that fixes the proximal end of the balloon sleeve can be used within the fixation through-holes 3732, 3832 to fix the proximal end of the stretch-valve tube 3730, 3830 thereat. Finally, if the fixation through-holes 3732, 3832 are outside the expanse of the balloon sleeve proximally (not illustrated), then an adhesive or the same material that creates the outer wall 3740, 3840 (see below)

can be used within the fixation through-holes 3732, 3832 to fix the proximal end of the stretch-valve tube 3730, 3830.

In Step 4122, the balloon sleeve is placed about the inflation port 3724, 3824 and, if present, fixation through-holes 3732, 3832 and the balloon sleeve is fixed to the exterior of the inner and inflation lumen walls 3710, 3720, 3810, 3820 at both ends to define a fluid-tight balloon interior therebetween. As such, inflation of the balloon 3742, 3842 can occur through the inflation lumen 3722, 3822. For example, the balloon sleeve making up the inner wall of the balloon 3742, 3842 is slid over the distal end of the dual-lumen extrusion to cover at least the inflation port 3724, 3824 and is fluid-tightly sealed to the inner multi-lumen extrusion at both ends of the balloon sleeve but not in the intermediate portion. The balloon sleeve can be made of latex as well and, therefore, can be secured to the latex multi-lumen extrusion in any known way to bond latex in a fluid-tight manner.

In Step 4124, the entire sub-assembly is covered with the outer wall 3740, 3840. For example, the entire sub-assembly is dipped into latex in its liquid form to create the outer wall 3740, 3840. In the alternative embodiment where a distal inflation lumen plug 3736, 3836 is not used, the latex can be allowed to enter at least a portion of the distal end of the inflation lumen 3722, 3822 but not so far as to block the inflation port 3724, 3824. When the latex cures, the balloon 3742, 3842 is fluid tight and can only be fluidically connected to the environment through the proximal-most opening of the inflation port, which is fluidically connected to the inflation lumen 3722, 3822. In this process, the inner wall 3710, 3810, the inflation lumen wall 3720, 3820, the plug 3736, 3836, the balloon wall, and the outer wall 3740, 3840 are all made of the same latex material and, therefore, together form a very secure water-tight balloon 3742, 3842. (Further exemplary embodiments for securing the stretch-valve tube 3730, 3830 in the catheter 3700, 3800 are described below with regard to FIGS. 48 to 56.)

In such configurations, therefore, any proximal movement of the catheter 3700, 3800 at or proximal of the proximal anchor 3732, 3832 will also move the stretch-valve tube 3730, 3830 proximally; in other words, the distal end of the stretch-valve tube 3730, 3830 can slide within the inflation lumen 3722, 3822 in a proximal direction.

The steps outlined above in the exemplary embodiments need not be done in the order described or illustrated. Any of these steps can occur in any order to create the catheter according to the various exemplary embodiments.

Figure 42:
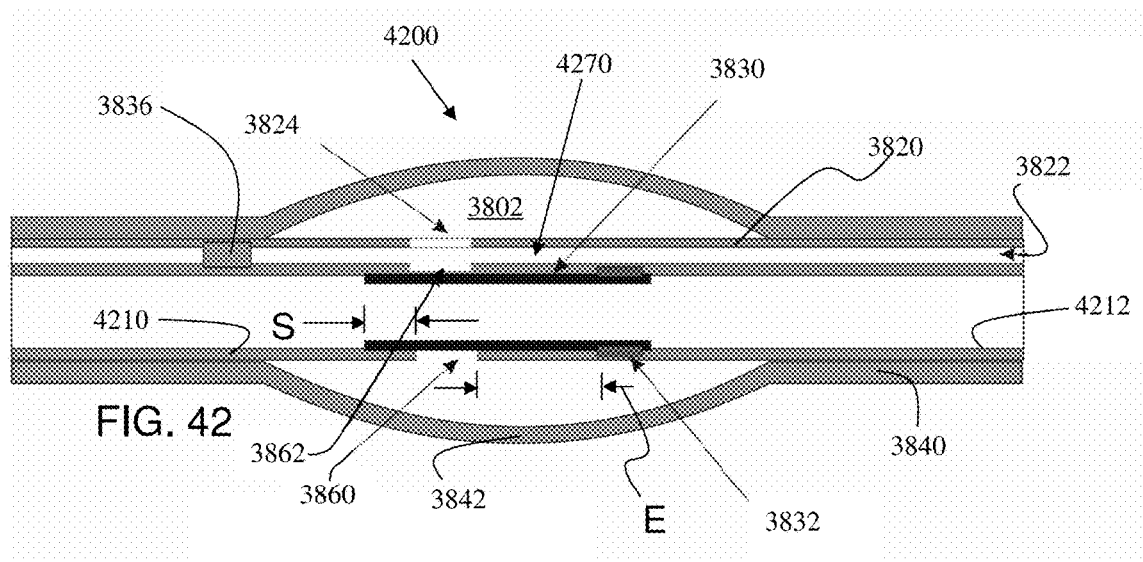
FIG. 42 is a fragmentary, enlarged, longitudinal cross-sectional view of a balloon portion of another exemplary embodiment of an automatically deflating, stretch valve urinary balloon catheter according to the invention with the balloon in a partially inflated state and the stretch valve in an unactuated state.
Figure 43:
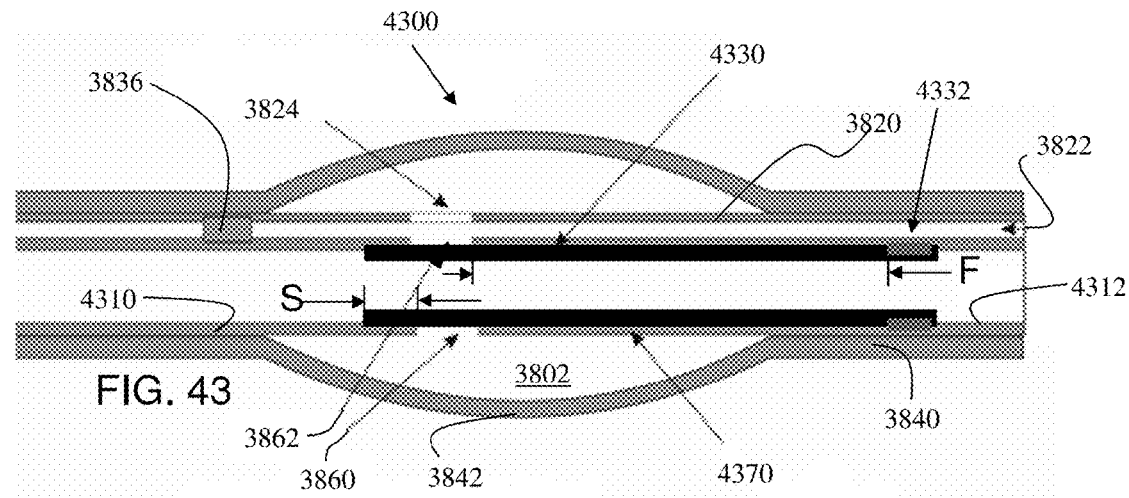
FIG. 43 is a fragmentary, enlarged, longitudinal cross-sectional view of a balloon portion of still another exemplary embodiment of an automatically deflating, stretch valve urinary balloon catheter according to the invention with the balloon in a partially inflated state and a longer stretch valve in an unactuated state.
Figure 48:
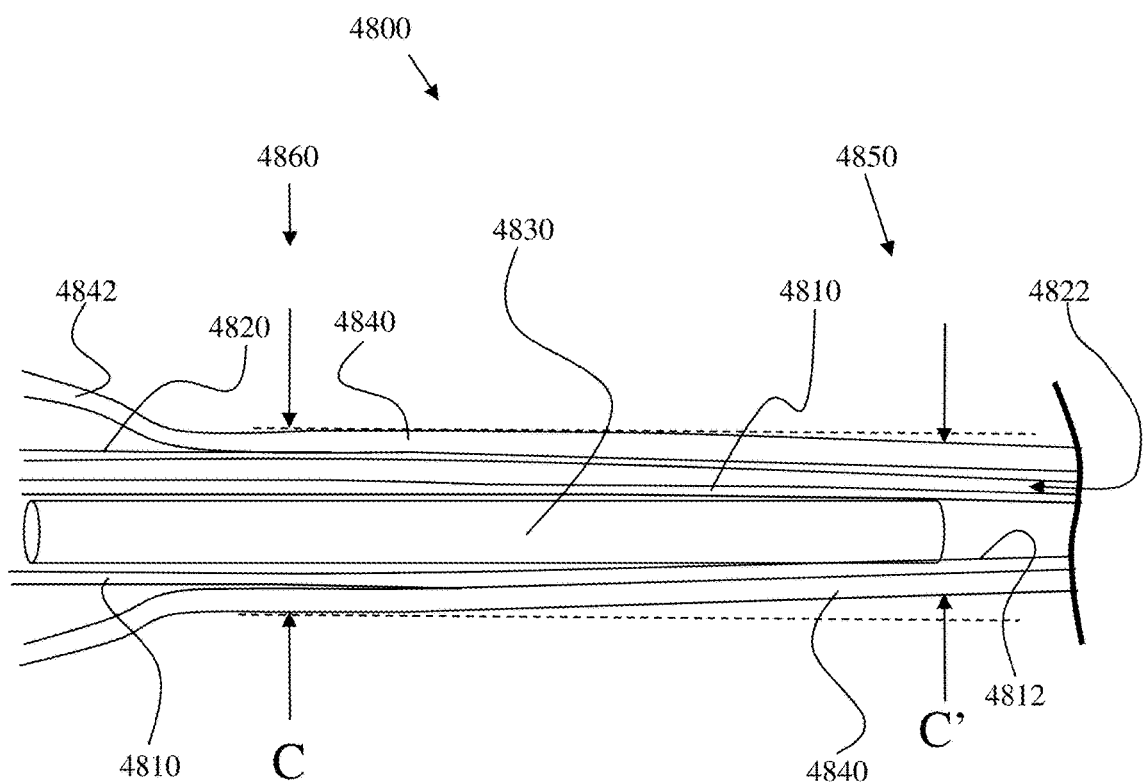
FIG. 48 is a fragmentary, enlarged, longitudinal cross-sectional view of a stretching portion of an automatically deflating, stretch valve balloon catheter with the proximal end of the stretch-valve tube gripped within a drainage lumen.

FIGS. 42 and 43 illustrate the balloon portion of other exemplary embodiments of the inventive catheter 4200, 4300, again with the balloon 3842 in a partially inflated state. In these exemplary embodiments, most of the features are the same as the catheter 3800 shown in FIG. 38, as well as in the other exemplary embodiments of the safety catheters described herein. What is different in FIGS. 42 and 43 is how the stretch valve operates and, therefore, the similar features use the same reference numerals as in FIG. 38. Different features, however, use new reference numerals. Thus, description of the similar features is not repeated below and is, instead, incorporated herein by reference from the above-mentioned exemplary embodiments.

In the catheters 4200, 4300, the annular inner lumen wall 4210, 4310 defines therein a drainage lumen 4212, 4312. In this exemplary embodiment, a hollow stretch-valve tube 3830 is disposed in the drainage lumen 4212, 4312 to not hinder drainage of the fluid to be drained (e.g., urine). While the diameter of the stretch-valve tube 3830 can be any size that accommodates substantially unhindered fluid flow through the drainage lumen 4212, 4312, one exemplary inner diameter of the stretch-valve tube 3830 is substantially equal to the diameter of the drainage lumen 4212, 4312 and the outer diameter of the stretch-valve tube 3830 is just slightly larger than the diameter of the drainage lumen 4212, 4312 (e.g., the wall thickness of the tube can be between 0.07 mm and 0.7 mm). (In any embodiment of the stretch-valve tube mentioned herein, the outer diameter can be equal to or less than the diameter of the drainage lumen.) Another exemplary embodiment of the stretch-valve tube 3830, 4330 has one or more of the proximal and distal ends thereof larger in outer diameter than an intermediate portion of the stretch-valve tube 3830, 4330. Thus, if one end is larger, the stretch-valve tube 3830, 4330 has a "club" shape and, if both ends are larger, the stretch-valve tube 3830, 4330 has a "dumbbell" shape. An exemplary configuration of a dumbbell shaped stretch-valve tube is described hereinbelow.

The proximal end of the stretch-valve tube 3830 in this exemplary embodiment is proximal of a proximal end of a deflation port 3860. The longitudinal length of the deflation port 3860 is not distal of the distal end of the balloon 3842 so that the balloon 3842 can be deflated; the distal end can be anywhere between the two ends of the balloon 3842 but is shown in an intermediate position in FIGS. 42 and 43. The distal end of the stretch-valve tube 3830 is at a distance S distal of the deflation port 3860 and selection of this distance S is dependent upon the amount of stretch required to actuate the stretch-valve of the inventive catheter 4200, 4300 as described herein.

In the exemplary embodiments of FIGS. 38, 42 and 43, the longitudinal length of the deflation port 3860 is shown as less than one half of the longitudinal length of the stretch-valve tube 3830. The drainage port 3860 is formed through the inner lumen wall 3810 and the stretch-valve tube 3830 is positioned to overlap at least the drainage port 3860. In this manner, a portion of the outer surface of the proximal end of the stretch-valve tube 3830 closes off the drainage port 3860 to prevent fluid communication from the balloon 3842 to the drainage lumen 4212, 4312 through the drainage port 3860. A second drainage port 3862 is provided in the inner lumen wall 3810 aligned with the drainage port 3860, and both drainage ports 3860, 3862 are aligned with the inflation port 3824. As such, when the stretch-valve tube 3830 moves proximally to uncover the drainage ports 3860, 3862, inflation fluid 3802 from inside the balloon 3842 exits from both the inflation port 3824 and the drainage port 3860.

To secure the stretch-valve tube 3830 in the catheter 4200, 4300, a proximal anchor 4232, 4332 is disposed in the drainage lumen 4212 away from the deflation ports 3860, 3862, here proximally at a distance E in FIG. 42 and at a longer distance F in FIG. 43. The distances shown are not the only sizes for the stretch-valve tube 3830 and can be shorter or longer, the latter extending well into the drainage lumen 4212, 4312 proximally even further than shown in FIG. 43. The proximal anchor 3832 can be any size or shape that accommodates substantially unhindered fluid flow through the drainage lumen 4212, 4312, one exemplary inner diameter of the hollow anchor 3832 being a tube or ring substantially equal to the diameter of the drainage lumen 4212 with an outer diameter just slightly larger than the diameter of the drainage lumen 4212 (e.g., the thickness of the tube can be between 0.07 mm and 0.7 mm). The proximal anchor 3832 can be a barb or other mechanical fixation device as well, whether integral or connected to the stretch-valve tube 3830. The longitudinal length of this anchor 3832 can be as long as desired but enough to longitudinally fixedly secure the proximal end of the stretch-valve tube 3830 within the drainage lumen 4212 when installed in place. The anchor 3832 in this exemplary embodiment is at the proximal end of the balloon 3842 as shown in FIG. 42 but it can be further inside the balloon 3842 (i.e., distal with regard to FIG. 42) or entirely proximal of the balloon 3842 as shown in FIG. 43. The further proximal that the anchor 3832 is connected within the drainage lumen 4212, 4312, the greater the distance of stretching material is disposed between the anchor 3832 and the drainage ports 3860, 3862, thereby enhancing the ability of the safety catheter to stretch and activate the stretch-valve. (Further exemplary embodiments for securing the stretch-valve tube 3830, 4330 in the catheter 4200, 4300 are described below with regard to FIGS. 48 to 56.)

In such configurations, therefore, any proximal movement of the catheter 4200, 4300 at or proximal to the drainage ports 3860, 3862 will also move the stretch-valve tube 3830 proximally; in other words, the distal end of the stretch-valve tube 3830 can slide within the drainage lumen 4212 in a proximal direction. When the proximal end of the catheter 4200, 4300 is pulled to a force that is no greater than just before injury would occur to the bladder-urethral junction or the urethra if the catheter 4200, 4300 was still inflated when the force was imparted, the force will cause the distal end of the stretch-valve tube 3830 to slide proximally and translate and open the drainage ports 3860, 3862 at a deflation point, e.g., with a pulling force in a range of 1 to 15 pounds. In another exemplary embodiment, the range of force required to meet the deflation point is between 1 and 5 pounds, in particular, between 1.5 and 2 pounds.

When the deflation point of the stretch-valve tube 3830 occurs, the interior of the balloon 3842 becomes fluidically connected directly into the drainage lumen 4212, 4312 (which is open to the interior of the bladder 2020 and to the non-illustrated, proximal drain bag) and, due to the fact that the bladder is relatively unpressurized as compared to the balloon 3842, all internal pressure is released from the balloon 3842 to eject the inflating fluid 3802 directly into the drainage lumen 4212, 4312, thereby causing the balloon 3842 to deflate rapidly.

There exists the possibility that the distal end of stretch-valve tube 3830 might not slide or will slide with friction when the proximal end of the catheter 4200, 4300 is pulled to a force that is enough to reach the desired deflation point (and no greater than just before injury would occur). To prevent such a situation from occurring, it is desirable to enhance the stretchability of the inner lumen wall 4210 distal of the anchor 3832 and, in particular, the extent E between the drainage ports 3860, 3862 and the anchor 3832. Because the material of the catheters described herein is naturally stretchable, there are various ways to make the extent E stretch more than other portions of the catheter, in particular, the portion proximal of the anchor 3832. One way to increase the stretchability is to score the outside or inside of the material comprising the extent E with small cuts, notches, scratches, or other intentionally formed defects. Another way to make the extent E more stretchable than at least the portion proximal of the anchor 3832 is to grind down the exterior or interior of the extent E. A further way to make the extent E more stretchable is to chemically treat the material comprising the extent E. Yet another way to make the extent E more stretchable is to treat the material comprising the extent E with a local change in temperature, such as heating the extent E.

An altogether different way is to use different materials in the catheter 4200, 4300. In one exemplary embodiment, at least a portion of the extent E is replaced with another elastomeric material different from the remainder of the catheter, the other elastomeric material being more elastic than at least the portion of the catheter proximal of the anchor 3832. In another exemplary embodiment, the portion proximal of the anchor 3832 is made of an elastomeric material that is less elastic than the extent E.

FIG. 43 shows the stretch-valve tube 4330 significantly longer than the other stretch-valve tubes and attached by the anchor 4332 to the inner lumen wall 4310 even further proximally than the other stretch-valve tubes. By making the stretch-valve tube 4330 longer, the extent E can be increased, thereby making stretch of the portion just distal of the anchor 3832 easier and insuring activation of the stretch valve. Any of the exemplary embodiments of the stretch-valve tube can have a different length than illustrated and/or described. Combining this increase or decrease in length of the stretch-valve tube with a decrease in the outer diameter of the stretch-valve tube can allow for tailoring the stretch-valve tube to various stretch release forces as described below with regard to FIG. 49.

Even though the exemplary embodiments 4200, 4300 are shown herein with reference to FIG. 38, they are not limited thereto and can be applied to each of the other exemplary embodiments described herein as well. Further, the stretch enhancement feature can be added to the outer wall instead of or in addition to the inner lumen wall. If the stretch enhancement 4270, 4370 is included in the production of any of the herein-mentioned catheters, then another manufacturing step will be needed. As such, a stretch-enhancement creation step will be added, for example, in the flow chart of FIG. 39 anywhere after step 3910, in the flow chart of FIG. 40 anywhere after step 4010, and in the flow chart of FIG. 41 anywhere after step 4110.

Alternative exemplary embodiments combine various features of the embodiments described herein. For example, FIGS. 44 to 47 illustrate other exemplary embodiments of the stretch-valve tubes mentioned above. Where some features are mentioned already, similar reference numerals are used and the descriptions thereof are not repeated.

With regard to FIGS. 44 and 45, in contrast to a solid tube, the stretch-valve tube 4430 of the inventive catheter 4500 has a proximal tubular section 4432, a distal tubular section 4434, and an intermediate connector 4436. As before, FIG. 45 illustrates a balloon portion of the inventive catheter 4500 with a balloon 3842 in a partially inflated state. An annular inner lumen wall 3810 defines therein a drainage lumen 3812. At one or more circumferential longitudinal extents about the inner lumen wall 3810, an inflation lumen wall 3820 defines an inflation lumen 3822 and a balloon inflation port 3824 fluidically connected to the inflation lumen 3822; in the inventive catheter 4500, there can be more than one inflation lumen 3822 and corresponding inflation port 3824 even though only one is shown herein. A lumen plug 3836 fluidically closes the inflation lumen 3822 distal of the inflation port 3824 so that all inflation fluid 3802 is directed into the balloon 3842. The lumen plug 3736 can plug any point or extent from the inflation port 3724 distally. An outer wall 3840 covers all of the interior walls 3810 and 3820 in a fluid-tight manner and forms the exterior of the balloon 3842 but does not cover the distal end of the drainage lumen 3812. The outer wall 3840 is formed in any way described herein and is not discussed in further detail here.

In this exemplary embodiment, the stretch-valve tube 4430 is disposed in the drainage lumen 3812 to not hinder drainage of the fluid to be drained (e.g., urine). While the diameter of the stretch-valve tube 4430 can be any size that accommodates substantially unhindered fluid flow through the drainage lumen 3812, one exemplary inner diameter of the stretch-valve tube 4430 is substantially equal to the diameter of the drainage lumen 3812 and the outer diameter of the stretch-valve tube 4430 is just slightly larger than the diameter of the drainage lumen 3812 (e.g., the wall thickness of the tube can be between 0.07 mm and 0.7 mm). The proximal tubular section 4432 of the stretch-valve tube 4430 in this exemplary embodiment is proximal of a proximal end of the deflation port 3860. The distal tubular section 4434 of the stretch-valve tube 4430 is not distal of the distal end of the balloon 3842 so that the balloon 3842 can be deflated; the distal end can be anywhere between the two ends of the balloon 3842 but is shown in an intermediate position in FIG. 45. The distal tubular section 4434 of the stretch-valve tube 4430 covers the deflation port 3860 longitudinally in the steady-state or unactuated state of the valve. The overlap distance S distal of the deflation port 3860 is dependent upon the amount of stretch required to actuate the stretch-valve of the inventive catheter 4500 as described below.

To secure the stretch-valve tube 4430 in the catheter 4500, a proximal anchor 3832 is disposed in the drainage lumen 3810 away from the deflation ports 3860, 3862, here proximally. The proximal anchor 3832 can be any size or shape that accommodates substantially unhindered fluid flow through the drainage lumen 3812, one exemplary inner diameter of the hollow anchor 3832 being a tube or ring substantially equal to the diameter of the drainage lumen 3812 with an outer diameter just slightly larger than the diameter of the drainage lumen 3812 (e.g., the thickness of the tube can be between 0.07 mm and 0.7 mm). The proximal anchor 3832 can be a barb or other mechanical fixation device as well, whether integral or connected to the stretch-valve tube 4430. The longitudinal length of this hollow anchor 3832 can be as long as desired but just enough to longitudinally fixedly secure the stretch-valve tube 4430 within the drainage lumen 3812 when installed in place. The anchor 3832 in this exemplary embodiment is at the proximal end of the balloon 3842 but can be further inside the balloon 3842 (distal) or entirely proximal of the balloon 3842 as shown. In an exemplary embodiment, the anchor 3832 has a stepped distal orifice that permits the proximal end of the stretch-valve tube 4430 to be, for example, press-fit therein for permanent connection. In another exemplary embodiment, the anchor 3832 is an adhesive or glue that fixes the proximal end of the stretch-valve tube 4430 longitudinally in place within the drainage lumen 3812. The adhesive can be the same material as any or all of the walls 3810, 3820, 3840 or it can be a different material. In an exemplary non-illustrated embodiment where a fixation port or set of fixation ports are formed through the inner wall 3810 proximal of the proximal-most end of the balloon 3842 and about the proximal end of the stretch-valve tube 4430, if the outer wall 3840 is formed by a dipping of the interior parts into a liquid bath of the same material as, for example, a dual lumen extrusion including the inner wall 3810 and the inflation lumen wall 3820, then, when set, the outer wall 3840 will be integral to both the inner wall 3810 and the inflation lumen wall 3820 and will be fixedly connected to the stretch-valve tube 3820 through the fixation port(s). (Further exemplary embodiments for securing the stretch-valve tube 4430 in the catheter 4500 are described below with regard to FIGS. 48 to 56.)

In such a configuration, therefore, any proximal movement of the catheter 4500 at or proximal to the deflation ports 3860, 3862 will also move the stretch-valve tube 4430 proximally; in other words, the distal end of the stretch-valve tube 4430 can slide within the drainage lumen 3812 in a proximal direction. When the proximal end of the catheter 4500 is pulled to a force that is no greater than just before injury would occur to the bladder-urethral junction or the urethra if the catheter 4500 was still inflated when the force was imparted, the force will cause the stretch-valve tube 4430 to slide proximally to place the distal end of the stretch-valve tube 4430 just proximal of the deflation ports 3860, 3862, e.g., with a pulling force in a range of 1 to 15 pounds. In another exemplary embodiment, the range of force required to meet the deflation point is between 1 and 5 pounds, in particular, between 1.5 and 2 pounds.

When the deflation point of the stretch-valve tube 4430 occurs, the interior of the balloon 3842 becomes fluidically connected directly into the drainage lumen 3812 (which is open to the interior of the bladder 2020 and to the non-illustrated, proximal drain bag) and, due to the fact that the bladder is relatively unpressurized as compared to the balloon 3842, all internal pressure is released from the balloon 3842 to eject the inflating fluid 3802 directly into the drainage lumen 3812, thereby causing the balloon 3842 to deflate rapidly. Because there is no intermediate structure between the balloon inflating fluid 3802 and the drainage lumen 3812, the rate at which the balloon 3842 deflates is fast. One way to speed up deflation can be to shape the deflation ports 3860, 3862 in the form of a funnel outwardly expanding in a direction from the outer wall 3840 towards the interior of the catheter 3800. Another way to speed up deflation can be to have two or more deflation ports 3860 about the circumference of the inner lumen wall 3810 and/or to enlarge the cross-sectional area of the deflation ports 3860, 3862.

The intermediate portion 4436 is not solid and is, instead, either a small tubular arc section (shown) or even multiple arc sections (not illustrated) or can be merely a line connecting the two tubular portions 4432, 4434 together (not illustrated). As such, the stretch-valve tube 4430 defines an intermediate flex gap. In such a configuration, if made from the same material as the other stretch-valve tubes described herein, the stretch-valve tube 4430 has increased flexibility due to the decrease in material used. If made of a material that has less flexibility, then the shortened proximal and distal portions 4432, 4434 combined with the narrow intermediate portion 4436 allows the stretch-valve tube 4430 to be sufficiently flexible to not hinder insertion of the catheter 4500. Further, insertion of the stretch-valve tube 4430 into the drainage lumen is similar.

With regard to FIGS. 46 and 47, also in contrast to a solid tube, the stretch-valve assembly 4730 of the inventive catheter 4700 has a proximal coil section 4632, a distal plug 4634, and a distal coil section 4436. As before, FIG. 47 illustrates a balloon portion of the inventive catheter 4700 with a balloon 3842 in a partially inflated state. An annular inner lumen wall 3810 defines therein a drainage lumen 3812. At one or more circumferential longitudinal extents about the inner lumen wall 3810, an inflation lumen wall 3820 defines an inflation lumen 3822 and a balloon inflation port 3824 fluidically connected to the inflation lumen 3822; in the inventive catheter 4700, there can be more than one inflation lumen 3822 and corresponding inflation port 3824 even though only one is shown herein. A lumen plug 3836 fluidically closes the inflation lumen 3822 distal of the inflation port 3824 so that an inflation fluid 3802 is directed into the balloon 3842. The lumen plug 3736 can plug any point or extent from the inflation port 3724 distally. An outer wall 3840 covers an of the interior walls 3810 and 3820 in a fluid-tight manner and forms the exterior of the balloon 3842 but does not cover the distal end of the drainage lumen

3812. The outer wall 3840 is formed in any way described herein and is not discussed in further detail here.

In this exemplary embodiment, the stretch-valve assembly 4630 is disposed in the drainage lumen 3812 to not hinder drainage of the fluid to be drained (e.g., urine). The proximal coil section 4632 has a larger diameter than the intermediate coil section 4636 because the proximal coil section 4632 acts as the device to secure the stretch-valve assembly 4630 inside the drainage lumen 3812 and the intermediate coil section 4636 acts as the measures by which the distal plug 4634 is moved out and away from the deflation port 3860, 3862. The intermediate coil section 4636 can have a pitch with looser coils to permit bending of the catheter body without kinking. While the diameter of the proximal coil section 4632 can be any size that accommodates substantially unhindered fluid flow through the drainage lumen 3812, one exemplary outer diameter of the rest- or steady-state of the proximal coil portion 4632 is just slightly larger than the diameter of the drainage lumen 3812 (e.g., the wall thickness of the tube can be between 0.07 mm and 0.7 mm). In comparison, one exemplary outer diameter of the rest- or steady-state of the intermediate coil section 4636 is just slightly smaller than the diameter of the drainage lumen 3812. In this manner, proximal movement of the secured proximal coil section 4632 pulls upon the intermediate coil section 4636 to cause the distal plug 4634 to slide out and proximally away from the deflation port 3860, 3862. One exemplary configuration of the distal plug 4634 is a heat shrunk polyolefin attached to the coil with cyanoacrylate.

The proximal coil section 4632 of the stretch-valve assembly 4630 in this exemplary embodiment is proximal of a proximal end of the deflation port 3860, 3862. The distal plug 4634 of the stretch-valve assembly 4630 is not distal of the distal end of the balloon 3842 so that the balloon 3842 can be deflated; the distal plug 4634 can be anywhere between the two ends of the balloon 3842 but is shown in an intermediate position in FIG. 47. The distal plug 4634 of the stretch-valve assembly 4630 covers the deflation ports 3860, 3862 longitudinally in the steady-state or unactuated state of the valve. An overlap distance distal of the deflation ports 3860, 3862 is dependent upon the amount of stretch required to actuate the stretch-valve of the inventive catheter 4700 as described below.

To secure the stretch-valve assembly 4630 in the catheter 4700, no proximal anchor is needed in addition to the stretch-valve assembly 4630. Here, the proximal anchor is the proximal coil section 4632, which, when allowed to expand to its native diameter, self-secures in the drainage lumen 3812 and accommodates substantially unhindered fluid flow through the drainage lumen 3812. The longitudinal length of the proximal coil section 4632 can be as long as desired but just enough to longitudinally fixedly secure the stretch-valve assembly 4630 within the drainage lumen 3812 when installed in place. The anchor 4632 in this exemplary embodiment is proximal of the proximal end of the balloon 3842 but can be further inside the balloon 3842 (distal) or even further proximal of the balloon 3842 than shown. In another exemplary embodiment, an adhesive or glue can fix the proximal coil section 4632 of the stretch-valve assembly 4630 longitudinally in place within the drainage lumen 3812. The adhesive can be the same material as any or an of the walls 3810, 3820, 3840 or it can be a different material. In an exemplary non-illustrated embodiment where a fixation port or set of fixation ports are formed through the inner wall 3810 proximal of the proximal-most end of the balloon 3842 and about the proximal coil section 4632 of the stretch-valve assembly 4630, if the outer wall 3840 is formed by a dipping of the interior parts into a liquid bath of the same material as, for example, a dual lumen extrusion including the inner wall 3810 and the inflation lumen wall 3820, then, when set, the outer wall 3840 will be integral to both the inner wall 3810 and the inflation lumen wall 3820 and will be fixedly connected to the proximal coil section 4632 through the fixation port(s).

In such a configuration, therefore, any proximal movement of the catheter 4700 at or proximal to the drainage ports 3860, 3862 will also move the stretch-valve assembly 4630 proximally; in other words, the distal plug 4634 of the stretch-valve assembly 4630 can slide within the drainage lumen 3812 in a proximal direction. When the proximal end of the catheter 4700 is pulled to a force that is no greater than just before injury would occur to the bladder-urethral junction or the urethra if the catheter 4700 was still inflated when the force was imparted, the force will cause the distal plug 4634 to slide proximally to open the drainage ports 3860, 3862, e.g., with a pulling force in a range of 1 to 15 pounds. In another exemplary embodiment, the range of force required to meet the deflation point is between 1 and 5 pounds, in particular, between 1.5 and 2 pounds.

One exemplary method for installing the stretch-valve assembly 4630 in the drainage lumen 3812 is to turn down the coil of the proximal coil section 4632 temporarily on a mandrel that has a diameter equal to or smaller than the inner diameter of the intermediate coil section 4636 and hold it in place. Then, the contracted proximal coil section 4632 is inserted into the drainage lumen 3812 to the implantation or securing point. The, contracted proximal coil section 4632 is allowed to expand, thereby securing proximal portion of the stretch-valve assembly 4630 in the drainage lumen 3812 with the intermediate coil section 4636 and distal plug 4634 movably disposed therein.

The proximal and intermediate coil sections 4632, 4636 can be made of a single coil that is wound with two different diameters and/or two different pitches.

As set forth above, many of the exemplary catheters described herein can connect the stretch-valve tube merely by the shape of the tube itself. This connection is described with reference to FIG. 48, which illustrates a configuration of a catheter 4800 having features that applicable to each of the exemplary catheters described herein. Thus, the "48" prefix will be used for illustration purposes. In each of the catheters, an annular inner lumen wall 4810 defines therein a drainage lumen 4812 and an inflation lumen wall 4820 defines an inflation lumen 4822 and a non-illustrated balloon inflation port fluidically connected to the inflation lumen 4822. An outer wall 4840 covers an of the interior walls 4810 and 4820 in a fluid-tight manner and forms the exterior of the balloon 4842. A hollow, stretch-valve tube 4830 is disposed in the drainage lumen 4812 to not hinder drainage of the fluid to be drained (e.g., urine). While the diameter of the stretch-valve tube 4830 can be any size that accommodates substantially unhindered fluid flow through the drainage lumen 4812, the exemplary outer diameters of the stretch-valve tube 4830 allow the distal end of the stretch-valve tube 4830 to slide within the drainage lumen 4812 when the valve is activated. One exemplary size of the stretch-valve tube 4830 has one or more of the proximal and distal ends thereof larger in outer diameter than an intermediate portion of the stretch-valve tube 4830. Thus, if one end is larger, the stretch-valve tube 2830 has a "club" shape and, if both ends are larger, the stretch-valve tube 4830 has a "dumbbell" shape. An exemplary configuration of a dumbbell shaped stretch-valve tube is described hereinbelow.

In the various embodiments of catheters described herein, one end of the stretch-valve tube is indicated as being "fixed" in the respective catheter, while the opposite end is slidably disposed therein. Some exemplary embodiments described for fixing this end include adhesives (such as cyanoacrylate) and structures, and some describe the fixation as being fixed solely from its shape alone. As used herein, therefore, the measures for "fixation" do not need to be a separate material or a separate device. Accordingly, some exemplary embodiments can provide fixation of the stretch-valve tube simply by inserting the stretch-valve tube within the respective lumen. More specifically, one consequence of stretching the flexible catheter (for example, when a urinary catheter is prematurely pulled out) is that the stretched portion collapses radially inwards towards the longitudinal axis as the catheter body lengthens. There are two common examples of explaining this behavior: the Poisson Effect and the Chinese finger trap.

The Poisson effect is a negative ratio of transverse to axial strain. When a sample object is stretched (or squeezed), to an extension (or contraction) in the direction of the applied load, it corresponds to a contraction (or extension) in a direction perpendicular to the applied load. More specific to the invention herein, when the catheter is pulled relative to its ends, the catheter contracts in diameter and circumference. Therefore if a more rigid tube (the stretch valve) is placed in the lumen of a less rigid tube (the catheter), the diameter of the catheter decreases as it is extended axially and hugs the stretch valve. If the distal balloon on the catheter is held in place by the bladder-urethral junction and the proximal end of the catheter is pulled axially, as the catheter diameter contracts, it hugs the stretch valve and pulls the stretch valve proximally to the extent that it releases fluid from the balloon into at least one of the lumens in the catheter. This hugging is more pronounced on the proximal end (the right end in FIG. 48 than on the distal end). As such, the proximal end of the stretch-valve tube is squeezed while the distal end of the stretch-valve tube moves proximally to open the safety valve.

Another way to explain this effect is with the Chinese finger trap, also known as a Chinese finger puzzle or Chinese handcuffs (a gag toy used to play a practical joke). The finger trap is a simple puzzle that snares the victim's fingers (often the index fingers) in both ends of a small, woven bamboo cylinder. The initial reaction of the victim is to pull the fingers outward (i.e., stretching the tube), but this only tightens the trap. The way to escape the trap is to push the ends toward the middle, which enlarges the circumference of the two end openings and frees the fingers. The tightening is simply a normal behavior of a cylindrical, helically wound braid, usually the common biaxial braid. Pulling the entire braid from its ends lengthens and narrows it. The length is gained by reducing the angle between the warp and weft threads at their crossing points, but this reduces the radial distance between opposing sides and hence the overall circumference.

The stretch-valve described herein takes advantage of the Poisson and Chinese Puzzle Effects by extending the stretch-valve tube 4830 sufficiently proximal so that the proximal end resides within the area of stretching. This distance need not be far towards the proximal end of the catheter and can even reside in the proximal end of the balloon 4842. However, it has been found that a short distance, such as a few millimeters to a few centimeters is all that is needed to position the proximal end in the area of stretching. As such, when the balloon 4842 is held stationary (e.g., in the bladder) and the proximal end of the catheter is pulled (e.g., by a patient), the reduction in circumference of the drainage lumen 4812 automatically increases the inward grasping force on the proximal end of the stretch-valve tube 4830 but does not place the same inward force against the distal end of the stretch-valve tube 4830 covering the drainage port (not illustrated in FIG. 48). This effect is illustrated in the enlarged FIG. 48 (which is not drawn to scale) where the distal portion of the stretch-valve tube 4830 shown (to the left) does not touch the interior wall of the drainage lumen 4812 but the proximal end of the stretch-valve tube 4830 (to the right) is squeezed by the interior wall of the drainage lumen 4812. Simply put, as the proximal end of the catheter 4800 is pulled away from the balloon 4842, the center portion 4850 of the catheter 4800 being stretched decreases in circumference C" and grips the proximal end of the stretch-valve tube 4830 while the unstretched or less-stretched portion 4860 substantially retains its circumference C, thereby allowing the distal end of the stretch-valve tube 4830 to slide and actuate the stretch valve of the present invention.

In this embodiment, therefore, all of the fixation through-holes 2150, 2450, 2750, 3732, 3832 describe above become unnecessary and lead to a very simple configuration for manufacturing. Not only the shape itself can provide the fixation as described, properties of the stretch-valve tube and the material comprising the lumen in which the stretch-valve tube resides can provide the fixation as well. For example, if the material of the stretch-valve tube 4830 is selected such that it slightly grips the interior of the drainage lumen 4812 (or vice versa), then the gripping of the proximal end of the stretch-valve tube 4830 can be increased.

Figure 49:
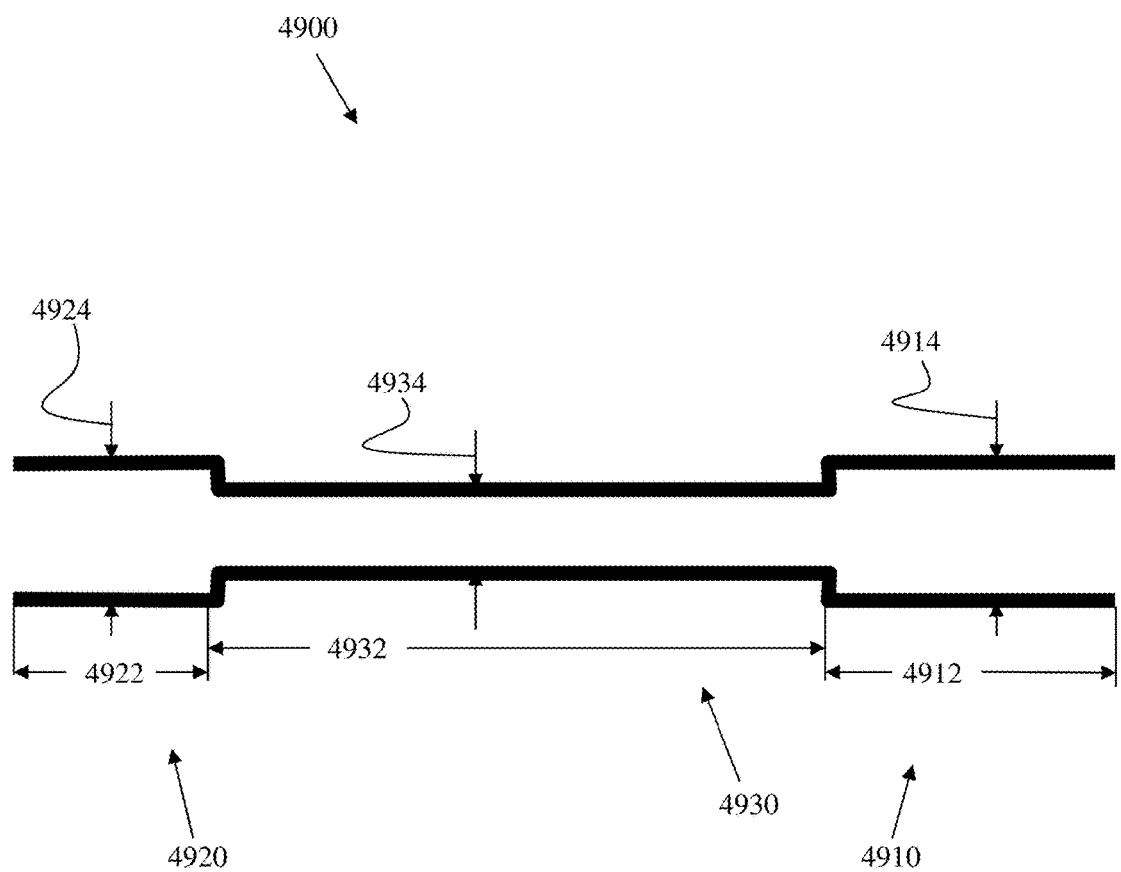
FIG. 49 is an enlarged, longitudinal cross-sectional view of an exemplary embodiment of a stretch-valve actuation device.

In some of the various embodiments of catheters described herein, the stretch-valve tubes have been shown as smooth cylinders. Alternative exemplary embodiments of these stretch-valve tubes do not require a constant outer diameter. The ability to tailor release of the stretch-valve can be enhanced when the stretch-valve tube 4900 has either or both of the proximal 4910 and distal 4920 ends of the stretch-valve tube 4900 larger in outer diameter than an intermediate portion 4930 of the stretch-valve tube 4900. In such a configuration, if one end is larger, the stretch-valve tube has a "club" shape (not illustrated) and, if both ends are larger (as shown in FIG. 49), the stretch-valve tube 4900 has a "dumbbell" shape.

The proximal 4910 and distal 4920 ends of the stretch-valve tube 4900 can be equal in outer diameter 4912, 4922 or they can have different outer diameters. In an exemplary embodiment, the outer surface of the distal end 4920 is smooth to seal against the deflation port(s). The outer surface of the proximal end 4910 can be smooth or rough or have fastening devices (such as barbs, extensions, adhesives). In an exemplary embodiment the outer diameter 4912 of the proximal end 4910 is slightly larger than the outer diameter 4922 of the distal end 4920. The overall length of the stretch-valve tube 4900 is between 1.5" and 3" or longer.

The following is an exemplary embodiment of a stretch valve tube 4900 where the inner diameter of the lumen in which the stretch-valve tube 4900 is to be placed (e.g., drain lumen of a Foley catheter) is 0.1" and the balloon of the catheter has a length of 1.0" with the balloon inflation hole and the drainage port located in the center of the balloon. For such a configuration, the approximate dimensions for the stretch valve made from a polyurethane tube of Shore 95A with a wall thickness of between approximately 0.004" and approximately 0.012", in particular, between approximately 0.006" and approximately 0.009", are as set forth in the following text.

The length of the proximal end 4912 is between approximately 0.1" and approximately 0.5", in particular, approximately 0.25". The outer diameter 4914 of the proximal end 4910 is between approximately 0.1" to 0.15", in particular, approximately 0.110". The length of the distal end 4922 is between approximately 0.1" and approximately 0.5", in particular, approximately 0.25". The outer diameter 4924 of the distal end 4920 is between approximately 0.1" to 0.15", in particular, approximately 0.108". The length 4932 of the intermediate portion 4930 is between approximately 0.5" and approximately 3" or longer, in particular, approximately 2". The outer diameter 4934 of the intermediate portion 4930 is between approximately 0.1" to 0.09", in particular, approximately 0.095".

It is noted that the length 4914 of the proximal end does not need to be the same as the length 4924 of the distal end and, in particular, it can be longer. Further, where the diameter measurement is normalized to 0.1" as above, the outer diameter 4914 of the proximal end 4910 is 10% larger and the outer diameter 4924 of the distal end 4920 is 8% larger. The inner diameter of the proximal 4920, intermediate 4930, and proximal 4910 portions can be the same or different (as shown. The wall thickness, too, can vary throughout if desired. For example, where the tube is an extrusion and the intermediate portion 4930 is made smaller by stretching, the wall will be reduced where it is stretched.

The drainage port of the balloon is located somewhere along the length 4922 of the distal end 4920, anywhere from the center of the length 4922 to 25% on either side thereof and, in particular, within the proximal 75% of the length 4922. If desired, the area opposing the drainage portion on the length 4922 can have raised boss to have a form-fit into the port.

If the stretch-valve tube is made by extrusion, it can be modified on a mold after it is extruded.

Figure 50:
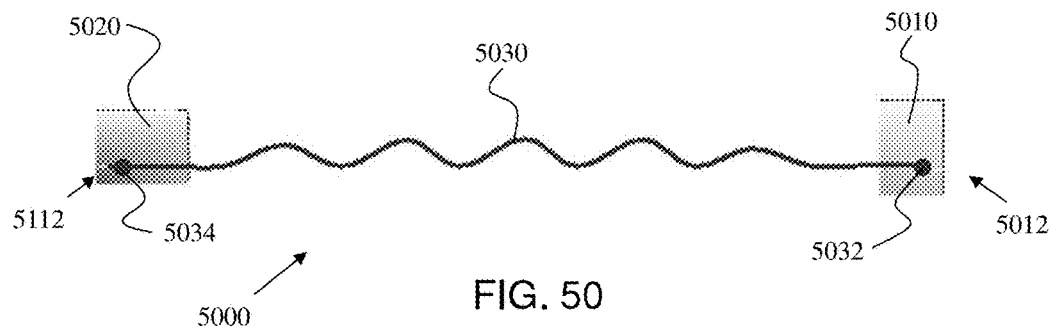
FIG. 50 is an enlarged, longitudinal cross-sectional view of an exemplary embodiment of a stretch-valve device.
Figure 51:
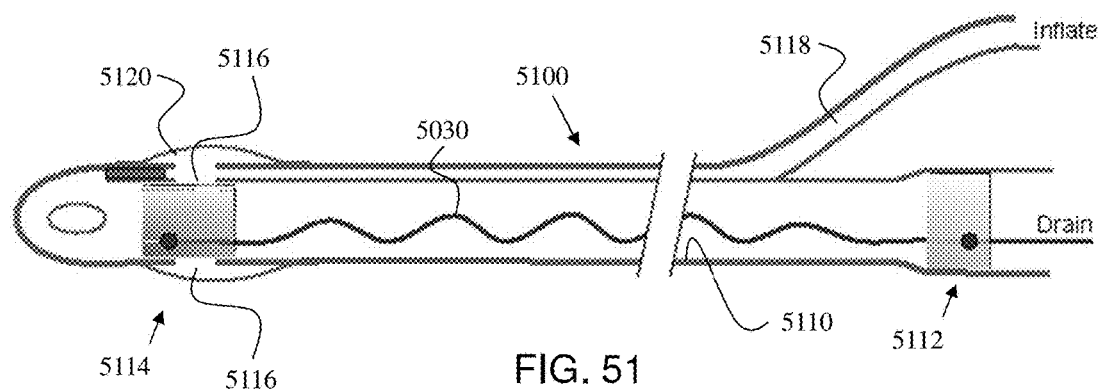
FIG. 51 is an enlarged, longitudinal cross-sectional view of the stretch-valve device of FIG. 50 installed within a catheter and in a valve-unactuated state.
Figure 52:
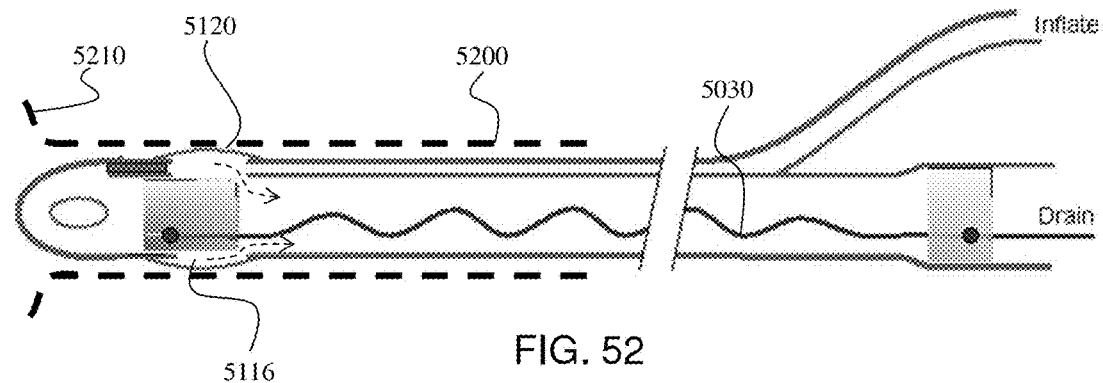
FIG. 52 is an enlarged, longitudinal cross-sectional view of the stretch-valve device of FIG. 50 installed within a catheter and in a valve-actuated state.

Other alternative exemplary embodiments of the stretch-valve tubes described herein do not require either a constant outer diameter or a connecting intermediate tube. Some of such exemplary embodiments have been described with regard to FIGS. 35, 36, and 44 to 47. The exemplary embodiment shown and described with regard to FIG. 36 has a string, rod, cord, or other linear, small diameter structure. Likewise, the exemplary embodiment shown and described with regard to FIG. 44 has a string, rod, cord, or other linear, small diameter structure connecting two tubular segments 4432, 4434. Still another exemplary embodiment of a stretch valve 5000 is shown in FIGS. 50 to 52. This stretch valve 5000 has a proximal cylindrical base 5010 and a distal cylindrical sliding plug 5020. Connecting the base 5000 and the plug 5020 is a connector 5030 that can be of any material with a higher modulus than the material comprising the catheter, for example, a monofilament or multi-stranded thread made of metal (stainless steel, titanium, Nitinol, cobalt chromium, and the like) or a polymer made from polyester terephthalate (PET), fluoropolymer (PTFE, polyvinylidene fluoride, etc.), polycarbonate, polyurethane, nylon, polyimide, polyamide, cellulose, polysulphone, or polyolefin (polyethylene, polypropylene, etc.). The material can also be a compound material, for example, a stretchable monofilament (e.g., Lycra® or spandex) braided or wound with a PET thread or the like, such as those stretchable filaments found on underwear or brassieres. One requirement is that, at some point when the catheter is stretched, the connector becomes taut and pulls the slidable plug from the drainage hole.

The base 5120 has a connection area 5012 that attaches the connector 5030 thereto. In this exemplary embodiment, the connection area 5012 is a slot projecting from a proximal edge of the base 5000 distally and the proximal end of the connector 5030 has an enlarged area 5032 that, when the connector 5030 is threaded into the slot 5012, the enlarged area 5032 rests on an outer surface of the base 5010 and, due to its size, it cannot pull through the slot. Furthermore, when the base 5010 is fixed in the proximal area 5112 of the drain lumen 5110, the enlarged area 5032 is trapped and thereby fixed in the drain lumen 5110 along with the base 5010. Likewise, the sliding plug 5020 has a connection area 5112 that connects the connector 5030 thereto. Here, the connection area 5112 is a slot projecting from a distal edge of the sliding plug 5000 proximally and the distal end of the connector 5030 has an enlarged area 5034 (such as a knot) that, when the connector 5030 is threaded into the slot 5112, the enlarged area 5034 rests on an outer surface of the sliding plug 5020. As such, when the sliding plug 5020 is slidably disposed in the area 5114 of the drain lumen 5110 within the balloon 5120 to plug the drainage ports 5116, the enlarged area 5034 is trapped and thereby sandwiched between the sliding plug 5020 and the surface of the drain lumen 5110 along with the sliding plug 5020. The connection areas 5012, 5112 being a slot and the enlarged area 5214 being, for example, a knot in the cord of the connector 5030 is merely one exemplary configuration of the structure for connecting the various respective parts to one another. Other examples include pin-holes where the connector is inserted through the pin hole and a knot is formed on the other side of the pin-hole to prevent the connector from pulling away from the pin-hole. Alternatively, instead of a knot, an adhesive can be used to fasten the connector to the plug or base.

FIG. 51 illustrates the stretch valve 5000 installed inside the drain lumen 5110 of the catheter 5100, for example, the drain lumen of a urinary catheter. In this illustration, the balloon 5120 is slightly inflated and the plug 5020 covers, i.e., plugs, the drainage ports 5116, which can be at the inflation lumen 5118 and opposite the inflation lumen 5118 as shown, or there can be additional ports around the circumference of the drain lumen 5110 within the interior extent of the balloon 5120. The connector 5030 is sized to be at least as long or longer than the longitudinal distance between the base 5010 fixed in the drain lumen 5112 and the plug 5020 when it plugs the drainage ports 5116. In such a configuration, the plug 5020 will remain in place to keep the balloon 5120 inflated until the catheter 5100 is stretched past the extent in which the connector 5030 becomes taut. With added stretching, therefore, the plug 5020 is pulled proximally (to the right in FIGS. 50 to 52) as the proximal end of the catheter 5100 (the right end of the catheter 5100 in FIGS. 50 to 52) is stretched further, as what occurs when a patient pulls the catheter 5100 in an attempt to remove it or when the drainage bag or line becomes tangled with the environment and the patient moves or falls. After the connector 5030 becomes taut and the plug 5020 starts to move proximally, the drainage ports 5116 are unplugged, thereby allowing the inflation fluid inside the balloon 5120 to drain into the drain lumen 5110 and prevent injury to a patient.

FIG. 52 illustrates a different situation than when the catheter 5100 is pulled by the patient or is tangled with the environment. In the situation of FIG. 52, the catheter 5100 is within a lumen 5200 of the patient, for example, a urethra, which is indicated with the dashed lines. The balloon 5120 is traversed within the urethra 5200 but not to the bladder 5210. In this situation, the balloon 5120 should not be inflated. Nonetheless, the person installing the catheter 5100 attempts to inflate the balloon 5120, which, if successful, would cause significant damage to the patient. As set forth above, the existence of the stretch valve provides the ability to control and eliminate inflation when the balloon 5120 is constricted. When the balloon 5120 is attempted to be inflated within the confines of a urethra, instead of stretching mostly in the radial direction, the small urethra causes the balloon to mostly stretch in the longitudinal direction—the same direction as the actuation axis of the stretch valve. Such a stretched state is shown in FIG. 52 and causes the stretch valve to open, by stretching open one or both of the deflation ports past one end of the plug 5020, prior to causing significant damage to the lumen and, thereby, directing the inflation fluid into the drain lumen 5110 instead of the balloon 5120 as indicated with the dashed arrows. In this situation, the balloon 5120 does not expand radially to cause any or as much damage as would be caused in a prior art urinary catheter.

In order to provide the above safety functionality, the plug 5020 has a longitudinal length that is between approximately 10% and approximately 100% greater on each side of the drainage ports 5116. In other words, in an example where the drainage port is 0.4 inches long, the plug 5020 has a length of between approximately 0.48" and 1.2" long. In particular, the plug 5020 has a longitudinal length that is between approximately 10% and approximately 40% greater on each side of the drainage ports 5116 or between approximately 15% and approximately 25% greater on each side of the drainage ports 5116.

Figure 53:
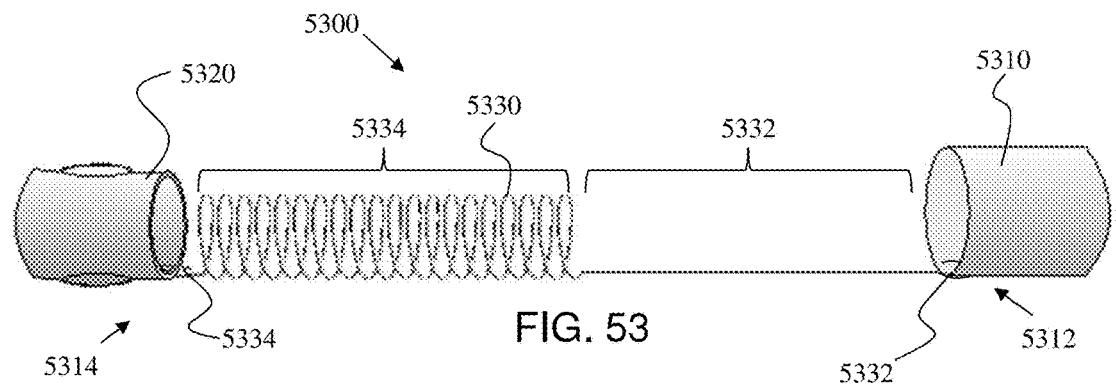
FIG. 53 is an enlarged, longitudinal cross-sectional view of an exemplary embodiment of a stretch-valve device.
Figure 54:
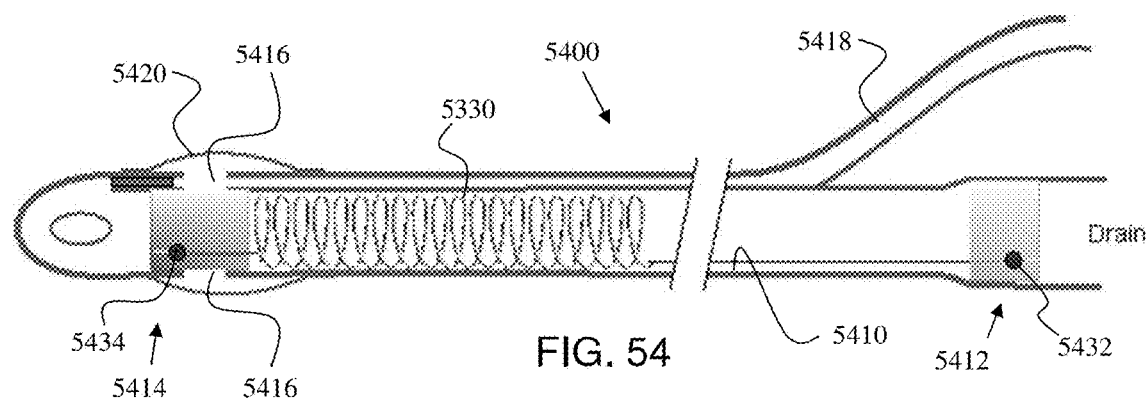
FIG. 54 is an enlarged, longitudinal cross-sectional view of the stretch-valve device installed within a catheter and in a valve-unactuated state.
Figure 55:
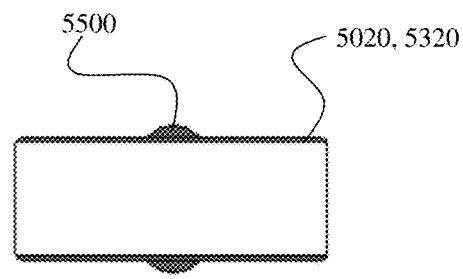
FIG. 55 is an enlarged, longitudinal cross-sectional view of an exemplary embodiment of a plug of the stretch-valve device of FIGS. 50 to 54.

Still another exemplary embodiment of a stretch valve 5300 is shown in FIGS. 53 to 55. This stretch valve 5300 has a proximal cylindrical base 5310 and a distal cylindrical sliding plug 5320. Connecting the base 5300 and the plug 5320 is an at least partially elastic connector 5330 that can be of any material, for example, a monofilament or multi-stranded thread made of metal (stainless steel, titanium, Nitinol, cobalt chromium, and the like) or a polymer made from polyester terephthalate (PET), fluoropolymer (PTFE, polyvinylidene fluoride, etc.), polycarbonate, polyurethane, nylon, polyimide, polyamide, cellulose, polysulphone, polyolefin (polyethylene, polypropylene, etc.). The material can also be a compound material, for example, a stretchable monofilament (e.g., Lycra® or spandex) braided or wound with a PET thread or the like, such as those stretchable filaments found on underwear or brassieres.

The connector 5330 can be inelastic at a first portion and elastic at a second portion or there can be a number of inelastic and elastic portions along the entire extent. In the exemplary embodiment shown in FIGS. 53 and 54, a proximal portion 5332 is inelastic and a distal portion 5335 is elastic and is in the form of a spring. The spring can be made of metal using spring-forming equipment well-known in the art. The spring can also be made from polymer that is heat-formed in a helical configuration.

The base 5300 has a connection area 5312 that attaches the connector 5330 thereto. In this exemplary embodiment, the connection area 5312 is a hole adjacent a proximal edge of the base 5300 and the proximal end of the connector 5330 has a hook 5332 that, when the connector 5030 is hooked into the hole 5312, the hook 5332 extends into the center of the base 5310. As such, when the base 5310 is fixed in the proximal area 5312 of the drain lumen 5410, the hook 5332 is trapped and thereby fixed in the drain lumen 5410 along with the base 5310. Likewise, the sliding plug 5320 has a connection area 5312 that connects the connector 5330 thereto. Here, the connection area 5312 is a hole adjacent a distal edge of the plug 5320 and the distal end of the connector 5330 has a hook 5334 that, when the connector 5330 is hooked into the hole 5312, the hook 5334 ends within the center of the sliding plug 5320. As such, when the sliding plug 5320 is slidably disposed in the area 5314 of the drain lumen 5410 within the balloon 5420 to plug the drainage ports 5416, the hook 5334 is trapped and thereby sandwiched between the sliding plug 5320 and the surface of the drain lumen 5410 along with the sliding plug 5320.

FIG. 54 illustrates the stretch valve 5300 installed inside the drain lumen 5410 of the catheter 5400, for example, the drain lumen of a urinary catheter. In this illustration, the balloon 5420 is slightly inflated and the plug 5320 covers, i.e., plugs, the drainage ports 5416, which can be at the inflation lumen 5418 and opposite the inflation lumen 5418 as shown, or there can be additional ports around the circumference of the drain lumen 5410 within the interior extent of the balloon 5420. The connector 5330 is sized to be substantially equal to the longitudinal distance between the base 5310 fixed in the drain lumen 5512 and the plug 5320 when it plugs the drainage ports 5416 without any substantial elastic stretching of the elastic portion 5334. In such a configuration, the plug 5320 will remain in place to keep the balloon 5420 inflated until the catheter 5400 is stretched to, thereby stretch the elastic portion past the extent in which the plug 5320 starts to slide. With this sliding, the plug 5320 moves proximally (to the right in FIGS. 53 and 54) as the proximal end of the catheter 5400 (the right end of the catheter 5400 in FIGS. 53 and 54) is stretched further, as what occurs when a patient pulls the catheter 5400 in an attempt to remove it or when the drainage bag or line becomes tangled with the environment and the patient moves or falls. After the elastic portion 5334 stretches and the plug 5320 starts to move proximally, the drainage ports 5416 become unplugged, thereby allowing the inflation fluid inside the balloon 5420 to drain into the drain lumen 5410 and prevent injury to a patient.

FIG. 54 shows an alternative exemplary embodiment of the connection areas and connection parts of the connector 5300. In this embodiment, the connection area 5412 is a slot projecting from a proximal edge of the base 5300 distally and the proximal end of the connector 5330 has an enlarged area 5432 (such as a knot) that, when the connector 5330 is threaded into the slot 5412, the enlarged area 5432 rests on an outer surface of the base 5310. As such, when the base 5310 is fixed in the proximal area 5412 of the drain lumen 5410, the enlarged area 5432 is trapped and thereby fixed in the drain lumen 5410 along with the base 5010. Likewise, the sliding plug 5320 has a connection area 5414 that connects the connector 5330 thereto. Here, the connection area 5414 is a slot projecting from a distal edge of the sliding plug 5320 proximally and the distal end of the connector 5330 has an enlarged area 5434 that, when the connector 5330 is threaded into the slot 5414, the enlarged area 5434 rests on an outer surface of the sliding plug 5320. As such, when the sliding plug 5320 is slidably disposed in the area of the drain lumen 5410 within the balloon 5420 to plug the drainage ports 5416, the enlarged area 5434 is trapped and thereby sandwiched between the sliding plug 5320 and the surface of the drain lumen 5410 along with the sliding plug 5320. The connection areas 5312, 5412, 5314, 5414 being a hole/hook or a slot/enlarged area are merely example of a structure for connecting the various respective parts to one another.

FIG. 54 illustrates an unactuated state of the stretch valve in the catheter 5400 such that, when the catheter 5400 is pulled by the patient or is tangled with the environment, the plug 5320 will move proximally away from the drainage ports 5416 and unplug them to allow the balloon inflation fluid to immediately drain into the drain lumen 5410.

FIGS. 53 and 55 show an alternative embodiment of the plug 5020, 5320 in which the plug 5020, 5320 is provided with a detent, a boss, or another extending structure that extends away from the outer surface of the sliding plug 5020, 5320 to resist movement out from the drainage ports 5116, 5416 as well as to help seal the drainage hole. Here, the plug 5020, 5320 is provided with two spherical portions or nubs 5500 on opposing sides to align with the two opposing drainage ports 5116, 5416 (as before, two in number is merely exemplary). These portions 5500 provide increased resistance to sliding of the plug 5020, 5320 and increase alignment of the stretch valve 5000, 5300 with respect to the catheter 5100, 5400 and increased sealing of the drainage hole. Although FIG. 55 shows a plug with two holes, the same can be accomplished with only one hole providing that there is only one transverse drainage hole to be sealed.

In the exemplary embodiments of FIGS. 50 to 55, the connector 5030, 5330 is shown as extending through the drain lumen 5110, 5410. The connector 5030, 5330 can also extend through the inflation lumen 5118, 5418 as well. One advantage of placing the stretch valve in the inflation lumen is that only inflation fluid (e.g., saline) is typically within the inflation lumen, which is not exposed to contamination from the bladder or urine. Another advantage of placing the stretch valve in the inflation lumen is that there is no narrowing of the drainage lumen. When urinary catheters are inserted, some patients develop small clots from the balloon rubbing against the bladder lining. Such clots can sometimes occlude the drain lumen even without a stretch valve. There also exists the possibility of calcium encrustation from the urine. A further advantage of placing the stretch valve in the inflation lumen is that such encrustation will not occur. One disadvantage of placing the stretch valve in the inflation is that it is smaller and, therefore, more difficult to function in a smaller diameter. However, the inflation lumen can be made larger to facilitate placement of the stretch-valve.

Figure 56:
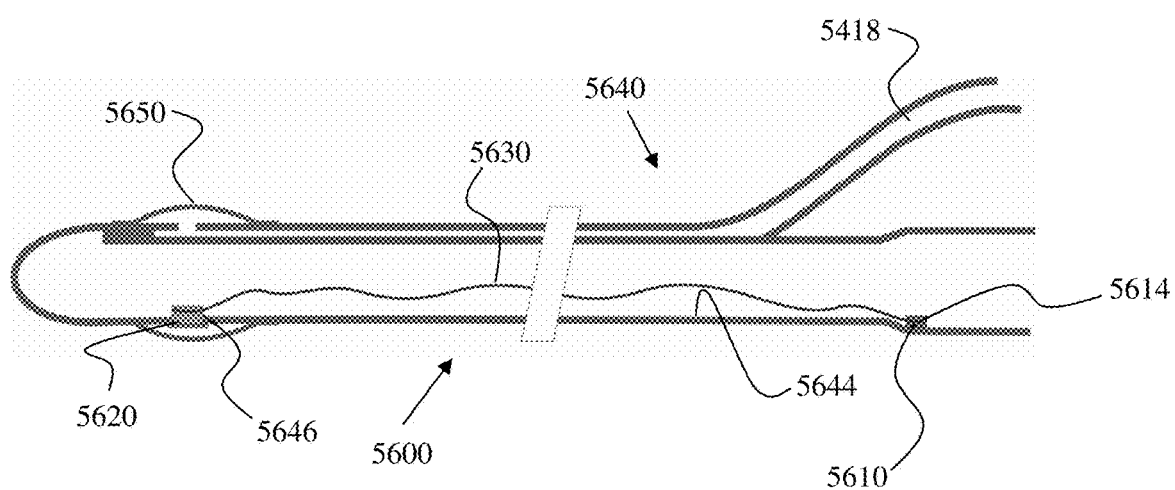
FIG. 56 is an enlarged, longitudinal cross-sectional view of an exemplary embodiment of a stretch-valve device installed within a catheter and in a valve-unactuated state.

In an alternate exemplary embodiment shown in FIG. 56, the plug 5620 can be a simple cork-like structure connected to the connector 5630. In this embodiment, the catheter 5640 has only one drainage port 5642. The base 5610 is fixed to the connector 5630 and is fixed to the interior wall of the drain lumen 5644. The plug 5620 also is fixed to the connector 5630 and is shaped to plug up the drainage port 5646. As such, when the plug 5620 is installed within the balloon 5650, it plugs the drainage port 5646.

FIG. 56 illustrates the stretch valve 5600 installed inside the drain lumen 5644 of the catheter 5640, for example, the drain lumen of a urinary catheter. In this illustration, the balloon 5650 is slightly inflated and the plug 5620 plugs the drainage port 5646, which can be anywhere about the drain lumen 5644 and even at the inflation lumen 5418. There can be additional drainage ports 5646 around the circumference of the drain lumen 5644 within the interior extent of the balloon 5650 each closed by another plug 5620 connected to the connector 5630. The connector 5630 is sized to be at least as long or longer than the longitudinal distance between the base 5010 fixed in the drain lumen 5644 and the plug 5620 when it plugs the drainage port 5646. In such a configuration, the plug 5620 will remain in place to keep the balloon 5650 inflated until the catheter 5640 is stretched past the extent in which the connector 5630 becomes taut. With added stretching, therefore, the plug 5620 is pulled proximally (to the right in FIG. 56) as the proximal end of the catheter 5640 (the right end) is stretched further, as what occurs when a patient pulls the catheter 5640 in an attempt to remove it or when the drainage bag or line becomes tangled with the environment and the patient moves or falls. After the connector 5630 becomes taut and the plug 5620 starts to move proximally, the drainage port 5646 is unplugged, thereby allowing the inflation fluid inside the balloon 5650 to drain into the drain lumen 5644 and prevent injury to a patient.

One exemplary embodiment of a plug 5020, 5320 has a longitudinal length of 0.25", an inner diameter of 0.09", and an outer diameter of 0.1". The nubs 5500 can be 0.005" high and have a base diameter 0.06" and can be produced, for example, by injection molding of the plug in a mold, wherein the nubs are formed in the mold with a ball mill.

In the exemplary embodiments of FIG. 56, the connector 5630 is shown as extending through the drain lumen 5644. The connector 5630 can also extend through the inflation lumen 5418 as well. In such a configuration, the plug 5620, when pulled proximally, will exit the drainage port 5646 and be pulled into the inflation lumen 5418. As the plug 5620 is much larger in size than the cross-section of the inflation lumen 5418, and due to the fact that the walls of the inflation lumen 5418 are flexible, the plug 5620 will become stuck within the inflation lumen 5418 and prevent re-inflation of the balloon 5650.

Each of the stretch-valve embodiments of FIGS. 21 to 38 and 42 to 56 also affords another significant benefit. The presence of the stretch-valve provides a way to self-regulate the balloon so that it is able to deflate automatically when over-inflated, a characteristic that is not present in the prior art. More specifically, when the balloon is overinflated, the stretch valve actuates to release the excessive pressure into the drain lumen. When the balloon is inflated to its intended size with the pre-defined amount of inflation fluid, the balloon expands without stretching any portion of the multi-lumen interior or the catheter material proximal of or distal to the balloon. However, when the balloon is over-inflated, this excessive inflation forces the ends of the balloon (i.e., the distal and proximal poles of the circular balloon) attached to the catheter to move away from each other. As this movement occurs, the drainage hole elongates to a point where it is longer than the stretch valve or becomes mis-aligned with the stretch valve, which actuates release of fluid from the balloon into the drainage lumen of the catheter. If the balloon is over-inflated sufficiently to actuate the stretch valve, the resulting movement automatically deflates the balloon until the proximal and distal ends of the balloon no longer stretch the catheter portions surrounding the balloon. When the ends of the balloon are no longer stretched, the stretch valve closes, thereby stopping deflation mid-stream and retaining the balloon in its intended inflation size.

In an exemplary embodiment of the safety urinary catheter, the stretch valve has the stretched state when the length between the proximal end of the catheter and the proximal balloon end is elongated between approximately 5 percent and approximately 200 percent, in particular, between approximately 5 percent and approximately 75 percent. Alternatively, or additionally, the stretch valve has the stretched state when the length between the ends of the balloon is elongated between approximately 5 percent and approximately 200 percent, in particular, between approximately 5 percent and approximately 75 percent.

The existence of the stretch valve also provides a further benefit—the ability to control and eliminate inflation when the balloon is constricted. It is known that inflation of a balloon in a lumen that is much smaller than the intended destination is a common occurrence (e.g., when the balloon of a catheter is attempted to be inflated within the confines of a urethra instead of the bladder) and leads to serious and debilitating patient injuries. Prior art catheters are unable to prevent inflation when constricted in a small lumen. In contrast, the stretch valve configurations described herein are able to prevent inflation when constricted in a small lumen. As described above, in addition to stretching in the radial direction, the balloon also stretches in the longitudinal direction—the same direction as the actuation axis of the stretch valve. When constricted in a lumen, the balloon is not permitted to stretch radially but is permitted to stretch longitudinally. This stretching causes the stretch valve to open prior to causing significant damage to the lumen in which the balloon is being inflated (e.g., the urethra), thereby directing the inflation fluid into the drain lumen instead of the balloon. In the particular embodiment of a urinary drainage catheter, the stretch valve opens before injury is caused to the lumen of the urethra.

In each of the embodiments where a stretch valve exists, actuation of the stretch valve within the patient can be indicated visually to a user or a health professional—a situation that is not able to be provided by prior art balloon catheters. As described above, a technician/physician/user inserting a balloon catheter does not know where the balloon is placed within the body after the balloon is inserted therein unless some type of costly radiographic or sonographic equipment is used. With the inventive safety catheters described herein, however, the inflation fluid has the opportunity to exit the balloon and, when it does, it provides a unique and automatic way of informing the user or healthcare professional that a dangerous condition has just been prevented and additional attention is desirable. More specifically, if the inflation fluid contains an inert colorant that is different from any color of fluid that typically is drained by the balloon catheter, the herein-described safety catheters will show, visually and immediately, either that an attempt has been made to inflate the balloon within a constricted lumen (such as the urethra) or that the catheter has been stretched enough to cause the stretch-valve of the inserted balloon to act and prevent possible pull-out injury. Almost immediately after triggering, the colored inflation fluid enters the fluid drainage bag. When anyone sees this colored fluid, he/she knows that the balloon is not correctly placed and corrective action needs to be taken immediately before injury or further injury occurs. Although the above describes a colored inflation fluid, the catheter can be provided with a powder dye dispersed in the deflated lumen of the device. When inflation media contacts and solubilizes the dye, the inflation media turns the color of the dye which, if released from the stretch valve as the balloon inflates, alerts the inserter of improper placement or inflation of the balloon. Placing the powder dye in the lumen allows the inserter to use conventional inflation media such as sterile saline.

In most of the embodiments described herein, reference is made to a urinary drainage catheter. As set forth herein, this is merely one good exemplary embodiment for describing the inventive safety features outlined herein. Specifically, the inventive features are not limited to a urinary drainage catheter; they can be applied to various and numerous catheter devices that probe various other areas of the anatomy and are used in other clinical situations.

In a first alternative exemplary embodiment, the self-regulating and self-deflating balloon can be used with coronary sinus catheter insertion. A coronary sinus catheter is a flexible device with a balloon at its end to be placed in the coronary sinus vein in the back of heart. It is used to deliver retrograde cardioplegia solution to arrest the heart for open heart surgery. In the prior art, if the balloon is overly distended, the vessel (CS) may rupture or bleed excessively, causing great harm to the patient or death. The stretch valve can be included in the coronary sinus catheter to limit the amount of inflation of that balloon, thereby preventing distension of the coronary sinus.

In a second alternative exemplary embodiment, the self-regulating and self-deflating balloon can be used with airway breathing tubes (such as endotracheal tubes and tracheostomy tubes). These devices are used commonly in medical care to provide assistance with breathing. After the trachea has been intubated, a balloon cuff of these devices is typically inflated just above the far end of the tube to help secure it in place, to prevent leakage of respiratory gases, and to protect the tracheobronchial tree from receiving undesirable material such as stomach acid. The tube is then secured to the face or neck and connected to a T-piece, anesthesia breathing circuit, bag valve mask device, or a mechanical ventilator. Over-distention of the balloon cuff can cause trauma and damage to the lining of the airway over time. This is so critical that medical personnel attempt to check the pressure of the balloon cuff at the time of first inflation and often thereafter. But gases may diffuse into or out from the balloons over time or too much air can be placed in the balloon inadvertently. The stretch valve can be included in these airway breathing tubes to limit the amount of inflation of that balloon, thereby preventing distension of the trachea.

In a third alternative exemplary embodiment, the self-regulating and self-deflating balloon can be used with thrombus removal devices, for example, Fogarty-type, atherectomy balloon catheters. These catheters are used to pull thrombi out of arteries. Accordingly, if the balloon of such catheters is over-inflated or over-pressurized (i.e., when the balloon is inflated in a compressed state such as in a lumen that is smaller than the balloon diameter), it can cause damage to the arterial wall, resulting in stenosis. The stretch valve can be included in these thrombus removal devices to limit the amount of inflation of that balloon, thereby preventing damage to arterial walls. Other Fogarty-type balloons are used to dilate strictures such as arterial venous fistula used for dialysis. These fistulas commonly stricture. In use, the Fogarty-type balloon is advanced proximal to the stricture and the balloon is inflated. The inflated balloon then is rapidly withdrawn across the stricture, which then opens the stricture by fracturing the fibrous bands. However it is not uncommon for the balloon to rupture and leave a foreign body in the lumen, which then would require an emergency operation. A balloon that self-deflates when experiencing such high pressures such as one including the stretch valve would prevent this from happening. Balloons are used to dilate strictures in almost any vessel in the body. Examples include, but are not limited to, strictures in the common bile duct, pancreatic duct, intestinal strictures often at anastomotic sites, lacrimal ducts, and parotid ducts. These vessels are often very delicate and can be damaged with over inflation. Strictures also occur in the urethtra, in the ureter, in the esophagus, and in the gastrointestinal tract. In each case, over-inflation of the balloon can cause a burst that may injury the structure in which it is being used. Combining the stretch valve described herein with such balloons would prevent this complication from happening.

In a fourth alternative exemplary embodiment, the self-regulating and self-deflating balloon can be used with balloon isolation catheters, which are used to block the flow of blood, for example, while drugs are injected on either side of the blockage. Over-distension of the balloon can cause damage to the vessel in which the isolation catheter is inflated. The stretch valve can be included in these balloon isolation catheters to limit the amount of inflation of that balloon, thereby preventing damage to lumen walls.

In a fifth alternative exemplary embodiment, the self-regulating and self-deflating balloon can be used with angioplasty balloon catheters, in particular, those comprised of flexible balloons including Nylon 12. Over-inflation of the balloon in such catheters can lead to rupture of the artery, which can be catastrophic to the patient. The stretch valve can be included in these angioplasty balloon catheters to limit the amount of inflation of that balloon, thereby preventing damage to lumen walls.

In a sixth alternative exemplary embodiment, the self-regulating and self-deflating balloon can be used with valvuloplasty catheters. Such catheters are used to break calcium deposits in heart valves. Over-distention can damage cells in the annulus of the valve, which can lead to inflammation and scar tissue formation. The stretch valve can be included in these valvuloplasty catheters to limit the amount of inflation of that balloon, thereby preventing damage to the annulus.

In a seventh alternative exemplary embodiment, the self-regulating and self-deflating balloon can be used with vertebroplasty balloons. If balloons for vertebroplasty are over-distended, they can cause rupturing of the vertebra. A release mechanism will render this procedure safer. The stretch valve is such a release mechanism for inclusion in a vertebroplasty device.

In an eighth alternative exemplary embodiment, the self-regulating and self-deflating balloon can be used with tamponade procedures. One example is during bronchoscopy when a biopsy is taken. After such a procedure, bleeding may occur. A balloon is passed over the bleed and inflated to compress the bleeding vessel. However, over-inflation in this delicate organ can easily cause ischemic damage. The stretch valve disclosed herein can be used with the tamponade balloon to prevent any injury from happening.

The various catheters 200, 300, 1000, 1600, 2100, 2400, 2700, 3300, 3400, 3500, 3600, 3700, 3800, 4200, 4300, 4500, 4700, 4800, 4900, 5100, 5400, 5640 described herein mention the catheter stretching from its proximal end when pulled. This movement can be described equally and correspondingly as a longitudinal movement of one of the ends of the balloon relative to the other of the ends of the balloon or, likewise, can be described as a longitudinal movement of one of the ends of the balloon away from the other of the ends of the balloon.

The catheters 200, 300, 1000, 1600, 2100, 2400, 2700, 3300, 3400, 3500, 3600, 3700, 3800, 4200, 4300, 4500, 4700, 4800, 4900, 5100, 5400, 5640 according to the invention can be used in vascular applications. It is known that every vessel has a tearing pressure. Balloons are used in coronary arteries, for example. If a coronary artery balloon were to burst, there would be less damage if the burst was controlled according to the invention. The same is true for a renal or iliac blood vessel. In such situations, the breakaway catheter improves upon existing catheters by making them safer. From the urinary standpoint, the breakaway balloon will not only prevent injury, but will also be a signal to the technician that he/she needs to obtain the assistance of a physician or urologist with respect to inserting the catheter.

The invention claimed is:
1. A safety balloon catheter, comprising:
a flexible, multi-lumen balloon catheter having:
a proximal catheter end;
a balloon defining a balloon interior to be inflated with an inflation fluid;
a hollow inflation lumen extending through the catheter to the balloon interior and shaped to convey the inflation fluid to and from the balloon interior;
a hollow second lumen parallel to the inflation lumen; and
a balloon drainage port fluidically connecting the balloon interior to the second lumen;
a stretch valve having:
a hollow base fixed in the second lumen adjacent the proximal catheter end and shaped to permit a fluid to pass therethrough; and
a hollow plug shaped to permit a fluid to pass therethrough and slidably positioned in the second lumen at a given distance from the base to:
in a steady state, prevent the inflation fluid from passing through the drainage port; and
in an actuated state, slide within the second lumen to permit the inflation fluid to pass through the drainage port and into the second lumen; and
a connector connected to the base and to the plug and having a length equal to or greater than the given distance.

2. The safety catheter according to claim 1, wherein the connector is inelastic.

3. The safety catheter according to claim 1, wherein the connector is partially elastic and partially inelastic.

4. The safety catheter according to claim 3, wherein the partially elastic portion of the connector is a spring.

5. The safety catheter according to claim 1, wherein the inflation lumen is fluidically connected to the balloon interior through at least one inflation port.

6. The safety catheter according to claim 5, wherein the balloon drainage port is a plurality of balloon drainage ports each fluidically connecting the balloon interior to the second lumen.

7. The safety catheter according to claim 6, wherein:
the plurality of balloon drainage ports each fluidically connect at least one of the balloon interior and the inflation lumen to the second lumen; and
the stretch valve:
in the steady state, positions the plug in the second lumen to prevent fluid from passing through the plurality of balloon drainage ports; and
in the actuated state, the plug slides within the second lumen to permit the inflation fluid to pass through the plurality of balloon drainage ports.

8. The safety catheter according to claim 1, wherein:
the balloon has a balloon proximal end;
the balloon catheter further comprises a stretch portion between the proximal catheter end and the balloon proximal end; and
the actuated state of the stretch valve is a stretched state of the stretch portion at a pull force of between approximately 1 pound and approximately 15 pounds applied to the proximal shaft portion.

9. The safety catheter according to claim 8, wherein, when the balloon portion is inflated with a fluid and a pull force of greater than approximately 15 pounds is applied to the stretch portion, the stretch valve meets the stretched state and thereby deflates the inflated hollow balloon portion.

10. The safety catheter according to claim 8, wherein, when the balloon portion is inflated with a fluid and a pull force of greater than approximately 5 pounds is applied to the stretch portion, the stretch valve meets the stretched state and thereby deflates the inflated hollow balloon portion.

11. The safety catheter according to claim 8, wherein, when the balloon portion is inflated with a fluid and a pull force of greater than approximately 2 pounds is applied to the stretch portion, the stretch valve meets the stretched state and thereby deflates the inflated hollow balloon portion.

12. The safety catheter according to claim 1, wherein:
the balloon has a balloon proximal end;
the balloon catheter further comprises a stretch portion between the proximal catheter end and the balloon proximal end; and
the actuated state of the stretch valve is a stretched state of the stretch portion at a pull force of between approximately 1 pound and approximately 5 pounds applied to the proximal shaft portion.

13. The safety catheter according to claim 1, wherein:
the balloon has a balloon proximal end;
the balloon catheter further comprises a stretch portion between the proximal catheter end and the balloon proximal end; and
the actuated state of the stretch valve is a stretched state of the stretch portion at a pull force of between approximately 1.5 pounds and approximately 2 pounds applied to the proximal shaft portion.

14. A safety urinary catheter, comprising:
a flexible, multi-lumen balloon catheter having:
  a proximal catheter end;
  a balloon having a proximal balloon end and defining a balloon interior to be inflated with an inflation fluid;
  a hollow inflation lumen extending through the catheter to the balloon interior and shaped to convey the inflation fluid to and from the balloon interior;
  a hollow drain lumen parallel to the inflation lumen; and
  a balloon drainage port fluidically connecting the balloon interior to the drain lumen;
a stretch valve having:
  a hollow base fixed in the drain lumen adjacent the proximal catheter end and shaped to permit a fluid to pass therethrough; and
  a hollow plug shaped to permit a fluid to pass therethrough and slidably positioned in the drain lumen at a given distance from the base to:
    in a steady state, prevent the inflation fluid from passing through the drainage port; and
    in a stretched state when a length between the proximal catheter end and the proximal balloon end is elongated between approximately 5 percent and approximately 200 percent,
    the plug slides within the drain lumen to permit the inflation fluid to pass through the drainage port and into the drain lumen; and
  a connector connected to the base and to the plug and having a length greater than the given distance.

15. The safety catheter according to claim 14, wherein the connector is inelastic.

16. The safety catheter according to claim 14, wherein the connector is partially elastic and partially inelastic.

17. A safety urinary catheter, comprising:
a flexible, multi-lumen balloon catheter having:
  a proximal catheter end;
  a balloon having proximal and distal balloon ends and defining a balloon interior to be inflated with an inflation fluid;
  a hollow inflation lumen extending through the catheter to the balloon interior and shaped to convey the inflation fluid to and from the balloon interior;
  a hollow drain lumen parallel to the inflation lumen; and
  a balloon drainage port fluidically connecting the balloon interior to the drain lumen;
a stretch valve having:
  a base fixed in one of the inflation lumen and the drain lumen adjacent the proximal catheter end at a given distance from the balloon drainage port and shaped to permit a fluid to pass thereby;
  a plug shaped to block the balloon drainage port when installed therewithin and prevent fluid from passing through the balloon drainage port; and
  a connector connected to the base and to the plug and having a length greater than the given distance, wherein:
    when the plug is installed in the balloon drainage port, the plug prevents the inflation fluid from passing through the balloon drainage port; and
    in a stretched state when a length between the proximal catheter end and the proximal balloon end is elongated between approximately 5 percent and approximately 200 percent, the plug exits the balloon drainage port to permit the inflation fluid to pass therethrough into the drain lumen.

18. The safety catheter according to claim 17, wherein:
the base is fixed in the inflation lumen adjacent the proximal catheter end;
when the plug is installed in the balloon drainage port, the plug prevents the inflation fluid from passing through the balloon drainage port; and
in a stretched state when a length between the proximal catheter end and the proximal balloon end is elongated between approximately 5 percent and approximately 200 percent, the plug exits the balloon drainage port into the inflation lumen to permit the inflation fluid to pass through the balloon drainage port into the drain lumen.

19. The safety catheter according to claim 17, wherein:
the base is fixed in the drain lumen adjacent the proximal catheter end;
when the plug is installed in the balloon drainage port, the plug prevents the inflation fluid from passing through the balloon drainage port; and
in a stretched state when a length between the proximal catheter end and the proximal balloon end is elongated between approximately 5 percent and approximately 200 percent, the plug exits the balloon drainage port into the drain lumen to permit the inflation fluid to pass through the balloon drainage port into the drain lumen.

20. The safety catheter according to claim 19, wherein the connector is one of:
inelastic; and
partially elastic and partially inelastic.

* * * * *